(12) United States Patent
Rodriguez

(10) Patent No.: US 6,489,480 B2
(45) Date of Patent: Dec. 3, 2002

(54) GROUP-15 CATIONIC COMPOUNDS FOR OLEFIN POLYMERIZATION CATALYSTS

(75) Inventor: George Rodriguez, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 11 days.

(21) Appl. No.: 09/734,443

(22) Filed: Dec. 11, 2000

(65) Prior Publication Data

US 2002/0111265 A1 Aug. 15, 2002

Related U.S. Application Data

(60) Provisional application No. 60/169,876, filed on Dec. 9, 1999.

(51) Int. Cl.⁷ ............... C07D 209/08; C07D 207/325; C07D 295/073; C07C 211/63; C07F 9/54
(52) U.S. Cl. ............... 546/192; 548/469; 548/490; 548/563; 548/577; 548/950; 564/289; 568/9
(58) Field of Search ............... 546/192; 548/469, 548/490, 563, 577, 950; 564/289; 568/9

(56) References Cited

U.S. PATENT DOCUMENTS

| | | | |
|---|---|---|---|
| 4,463,135 A | 7/1984 | Maly | 525/123 |
| 4,543,399 A | 9/1985 | Jenkins, III et al. | 526/70 |
| 4,588,790 A | 5/1986 | Jenkins, III et al. | 526/70 |
| 4,871,705 A | 10/1989 | Hoel | 502/117 |
| 4,892,851 A | 1/1990 | Ewen et al. | 502/104 |
| 4,937,299 A | 6/1990 | Ewen et al. | 526/119 |
| 5,001,205 A | 3/1991 | Hoel | 526/128 |
| 5,017,714 A | 5/1991 | Welborn, Jr. | 556/12 |
| 5,028,670 A | 7/1991 | Chinh et al. | 526/73 |
| 5,153,157 A | 10/1992 | Hlatky et la. | 502/117 |
| 5,198,401 A * | 3/1993 | Turner et al. | 502/155 |
| 5,241,025 A | 8/1993 | Hlatky et al. | 526/129 |
| 5,278,119 A | 1/1994 | Turner et al. | 502/155 |
| 5,278,264 A | 1/1994 | Spaleck et al. | 526/127 |
| 5,288,677 A | 2/1994 | Chung et al. | 502/152 |
| 5,296,433 A | 3/1994 | Siedle et al. | 502/117 |
| 5,296,434 A | 3/1994 | Karl et al. | 502/117 |
| 5,304,614 A | 4/1994 | Winter et al. | 526/127 |
| 5,308,816 A | 5/1994 | Tsutsui et al. | 502/108 |
| 5,312,881 A | 5/1994 | Marks et al. | 526/126 |
| 5,318,935 A | 6/1994 | Canich et al. | 502/117 |
| 5,324,800 A | 6/1994 | Welborn Jr. et al. | 526/160 |
| 5,352,749 A | 10/1994 | DeChellis et al. | 526/68 |
| 5,382,638 A | 1/1995 | Bontemps et al. | 526/67 |
| 5,405,922 A | 4/1995 | DeChellis et al. | 526/68 |
| 5,408,017 A | 4/1995 | Turner et al. | 526/134 |
| 5,427,991 A | 6/1995 | Turner | 502/103 |
| 5,436,304 A | 7/1995 | Griffin et al. | 526/68 |
| 5,447,892 A | 9/1995 | Marks et al. | 502/117 |
| 5,453,471 A | 9/1995 | Bernier et al. | 526/68 |
| 5,462,999 A | 10/1995 | Griffin et al. | 526/68 |
| 5,502,124 A | 3/1996 | Crowther et al. | 526/127 |
| 5,504,049 A | 4/1996 | Crowther et al. | 502/117 |
| 5,610,115 A | 3/1997 | Sega et al. | 502/152 |
| 5,635,573 A | 6/1997 | Harrington et al. | 526/170 |
| 5,668,234 A | 9/1997 | Rhodes et al. | 526/329.7 |
| 5,688,634 A | 11/1997 | Mixon et al. | 430/296 |
| 5,763,556 A | 6/1998 | Shaffer et al. | 526/348.4 |
| 5,767,208 A | 6/1998 | Turner et al. | 526/160 |
| 5,851,945 A | 12/1998 | Turner et al. | 502/103 |
| 5,895,771 A | 4/1999 | Epstein et al. | 502/103 |
| 5,919,983 A * | 7/1999 | Rosen et al. | 568/3 |
| 5,939,347 A | 8/1999 | Ward et al. | 502/104 |
| 6,346,636 B1 * | 2/2002 | Rodriguez | 556/173 |

FOREIGN PATENT DOCUMENTS

| | | |
|---|---|---|
| EP | 0 277 004 A | 8/1988 |
| EP | 0 129 368 B | 7/1989 |
| EP | 0543022 | 5/1993 |
| EP | 05430223 | 5/1993 |
| EP | 0 577 581 A | 1/1994 |
| EP | 0 578 838 A | 1/1994 |
| EP | 0 426 627 B | 4/1995 |
| EP | 0 570 982 B | 1/1997 |
| EP | 0 418 044 B | 9/1997 |
| EP | 0 591 756 B | 11/1998 |
| WO | WO 91/09882 | 7/1991 |
| WO | WO 92/00333 | 1/1992 |
| WO | WO 92/10066 | 6/1992 |
| WO | WO 93/02099 | 2/1993 |
| WO | WO 93/11172 | 6/1993 |
| WO | WO 93/14132 | 7/1993 |
| WO | WO 93/19103 | 9/1993 |

(List continued on next page.)

OTHER PUBLICATIONS

Abstract—Database Chemabs Online, Chemical Abstracts Service, Columbus, Ohio for Matsuura, Mitsunobu et al., "Image Formation of Silver Halide Color Photographic Material Containing Color Developer and Image Information Recording", JP 11 316434 A (Konica Co., Japan) Nov. 16, 1999.

(List continued on next page.)

*Primary Examiner*—Fiona T. Powers
(74) *Attorney, Agent, or Firm*—Charles E. Runyan

(57) ABSTRACT

This description addresses fluorinated amine compounds meeting the general formula $R'_i ArF-ER_2$, where ArF is a fluoroaryl group, E is nitrogen or phosphorous, each R is independently a $C_1-C_{20}$ hydrocarbyl group; or the two Rs may connect to form an unsubstituted or substituted $C_2-C_{20}$ cycloaliphatic group, R' is a $C_1-C_{20}$ hydrocarbyl or halogenated hydrocarbyl, and i is 0, 1 or 2. These compounds may be protonated with strong Bronsted acids to form protonated amine compounds that are useful for the preparation of organometallic catalyst-cocatalyst compounds comprising noncoordinating or weakly coordinating anions. The resulting organometallic catalyst-cocatalyst complexes can be effectively used as olefin polymerization catalysts. High number-average molecular weight polymers at high rates of productivity were observed from the use of metallocene catalyst complexes prepared with [N-pentafluorophenyl pyrrolidinium][tetrakis (pentafluorophenyl)borate] of [N-pentafluorophenyl pyrrolidinium][chloride].

18 Claims, No Drawings

FOREIGN PATENT DOCUMENTS

| WO | WO 94/01471 | 1/1994 |
|---|---|---|
| WO | WO 94/03506 | 2/1994 |
| WO | WO 95/07941 | 3/1995 |
| WO | WO 95/07942 | 3/1995 |
| WO | WO 96/23010 | 8/1996 |
| WO | WO 96/33227 | 10/1996 |
| WO | WO 96/35726 | 11/1996 |
| WO | WO 96/40296 A | 12/1996 |
| WO | WO 96/40796 A | 12/1996 |
| WO | WO 96/40805 | 12/1996 |
| WO | WO 97/22635 | 6/1997 |
| WO | WO 97/22639 | 6/1997 |
| WO | WO 97/29845 | 8/1997 |
| WO | WO 97/35893 | 10/1997 |
| WO | WO 97/48735 | 12/1997 |
| WO | WO 98/03558 | 1/1998 |
| WO | WO 98/37109 | 8/1998 |
| WO | WO 98/55518 | 12/1998 |
| WO | WO 99/09306 | 2/1999 |
| WO | WO 99/42467 | 8/1999 |
| WO | WO 99/43717 | 9/1999 |
| WO | WO 99/45042 | 9/1999 |
| WO | WO 99/50311 | 10/1999 |

OTHER PUBLICATIONS

Sammes, Michael P. et al: "Synthetic Applications of N–N linked heterocycles, Part 15. A facile synthesis of 4–pyridyl(aryl)amines via the reaction between 4–chloro–1–pyridiniopyridinium salts and aryl amines", *J. Chem. Soc., Perkin Trans.* 1 (1983), (5), pp. 973–8.

*J. Am. Chem. Soc.,*(1994), v. 116–pp. 6435–6436, Quyoum, et al., "A Carbocationic Olefin Polymerization Initiator Masquerading as a Ziegler–Natta Catalyst".

*J. of Organometallic Chem.,* (1989), v. 369–pp. 359–370 –Weisenfeldt, et al., *ansa–Metallocene Derivatives XVII.*

*Organometallics,*(1994), v. 13–pp. 954–963 –Spaleck, et al., *The Influence of Aromatic Subtituents on the Polymerization Behavior of Bridged Zirconocene Catalysts.*

*Organometallics,* (1994), v. 13–pp. 964–970–Stehling, et al., "*ansa–Zirconocene Polymerization Catalysts wiht Annelated Ring Ligands. . .*"

*Chem. Commun.,*(1998) pp. 849–850 –Gibson, et al., "*Novel Olefin Polymerization Catalysts Based on Iron and Cobalt*".

*Organometallics,*(1995), v. 14, pp. 5478–5480 –"Sterically Demanding Diamide Ligands: Synthesis and Structure of $d^0$Zirconium Alkyl Derivatives".

*Macromolecules,* (1996), v. 29, pp. 5241–5243 –Scollard, et al., "Polymerization of α–Olefins by chelating Diamide complexes of Titanium".

*Angew, Chem. Int. Ed.,* (1999) v. 37 –pp. 428–447 –Gibson, et al., "*the Search for New–Generation Olefin Polymerization Catalysts: Life Beyond Metallocenes*".

ABSTRACT –Database CHEMABS Online, Chemical Abstracts Service. Columbus, Ohio for Matsuura, Mitsunobu et al., "Image Formation of Silver Halide color Photographic Material containing Color Developer and Image Information Recording", JP 11 316434 A (Konica Co., Japan) Nov. 16, 1999.

Sammes, Michael P. et al., "Synthetic Applications of N–N linked heterocycles, Part 15. A facile synthesis of 4 –pyridyl(aryl)amines via the reaction between 4–chloro–1–pyridiniopyridinium salts and aryl amines", *J. Chem. Soc., Perkin Trans.*(1983), (5), pp. 973–8.

* cited by examiner

GROUP-15 CATIONIC COMPOUNDS FOR OLEFIN POLYMERIZATION CATALYSTS

This application claims the benefit of U.S. Provisional Application No. 60/169,876, filed Dec. 9, 1999.

TECHNICAL FIELD

This invention relates to ionic catalyst systems, especially to polymerization processes using ionic catalyst systems; to precursors for ionic catalyst systems comprising Group-15-containing cations and noncoordinating anions; and to methods of use of Group-15-element-containing cations.

BACKGROUND

The term "noncoordinating anion" (NCA) is now accepted terminology in the field of olefin and vinyl monomer polymerization, both by coordination or insertion polymerization and carbocationic polymerization. See, for example, EP 0 277 004, U.S. Pat. No. 5,198,401, Baird, Michael C., et al., J. Am. Chem. Soc. 1994, 116, 6435–6436, U.S. Pat. No. 5,312,881, U.S. Pat. No. 5,668,234, and WO 98/03558. The noncoordinating anions are described to function as electronic stabilizing counterions for essentially cationic metallocene complexes that are active for polymerization. The term noncoordinating anion as used here applies both to truly noncoordinating anions and anions that at most, coordinate so weakly that they are labile enough to allow for olefinic or acetylenic monomer insertion. These noncoordinating anions can be effectively introduced into a polymerization medium, separate from the organometallic catalyst compound or premixed with the catalyst prior to adding it to the polymerization medium, as Bronsted acid salts containing charge-balancing countercations.

Both U.S. Pat. No. 5,198,401 and WO 97/35893 specifically address nitrogen-containing Bronsted acid cations that are capable of abstracting a leaving (labile) group on neutral, organometallic transition-metal catalyst precursor compounds by donating a proton to such labile groups, thus rendering the catalyst precursor compounds cationic and providing a compatible, counterbalancing noncoordinating anion. U.S. Pat. No. 5,198,401 describes catalyst activator compounds represented by the formula $[(L'—H)^+]_d[(M')^{m+}Q_1Q_2 \ldots Q_n]^{d-}$ where L' is a neutral base, H is a hydrogen atom and $[(M')^{m+}Q_1Q_2 \ldots Q_n]$ is a metal or metalloid atom connected to a variety of ligands, preferably where M is boron and two or more of $Q_n$ are aromatic radicals, such as phenyl, napthyl and anthracenyl, each preferably fluorinated. L' is illustrated with various trialkyl-substituted ammonium complexes and N,N-dialkylanilinium complexes. WO 97/35893 describes cocatalyst activator compounds represented by the formula $[L*—H]^+[BQ'_4]^-$ where L* includes nitrogen-containing neutral Lewis bases, B is +3 boron, and Q' is a fluorinated $C_{1-20}$ hydrocarbyl group, preferably a fluorinated aryl group. The cocatalyst compounds are said to be rendered soluble in aliphatic solvents by incorporation of aliphatic groups, such as long chain alkyl or substituted-alkyl groups, into the Bronsted acid $[L*—H]^+$. Bis(hydrogenated-tallow-alkyl)methylammonium and di(dicosyl)methyl-ammonium salts are exemplified.

In view of the above there is a continuing need for cocatalyst activation compounds both to improve industrial economics and to provide alternative synthesis and preparation methods of these cocatalyst compounds. In particular, the catalyst activation reaction by the above nitrogen-containing cocatalyst compounds can result in neutral amine compounds, L, by loss of the hydronium atom, $H^+$, in the activating protonation reaction. These L compounds are Lewis bases that may interact with the strong Lewis acid, organometallic catalyst cations, and may in some cases adversely interfere with overall polymerization kinetics. See in particular, EP 0 426 637, where the use of carbenium, oxonium, and sulphonium cations are taught for replacement of Lewis base amines with the suggestion that catalyst poisons and undesirable residual amines can thus be avoided.

BRIEF SUMMARY

Embodiments of this invention address a process for preparing polyolefins from one or more olefinic monomers in which the olefins are combined with the reaction product of i) an organometallic catalyst compound and ii) a cocatalyst complex comprising a fluoroaryl-ligand-substituted secondary amine or phosphine and a Group-13-based noncoordinating or weakly coordinating anion. The invention cocatalysts provide residual amine or phosphine compounds with reduced basicity relative to those of the prior art, as well as noncoordinating or weakly coordinating anions for organometallic catalyst complexes that exhibit surprisingly high polymerization activities.

The term noncoordinating anion as used here applies both to truly noncoordinating anions and coordinating anions that are less coordinating than olefinic or acetylenic monomers. These noncoordinating anions can be effectively added to a polymerization medium or premixed with an organometallic catalyst compound before adding it to the polymerization medium, as Bronsted acid salts containing the invention charge-balancing countercations.

DETAILED DESCRIPTION

The invention provides a process for olefin polymerization in which Group-13 cocatalyst complexes and transition metal organometallic catalyst precursor compounds can be combined to form active olefin polymerization catalysts. After activation or essentially concurrent with activation, the catalyst is exposed to suitable monomer that has accessible olefinic, vinylic or acetylenic unsaturation.

Using the general formula $[L—H]^+ [A]^-$, where $[A]^-$ is any anion suitable for olefin polymerization, the Lewis base compounds, L, of the invention are typically based on fluorinated amine compounds meeting the general formula $R'_iArF—ER_2$ where ArF is a fluoroaryl ligand, E is nitrogen or phosphorous, and each R is independently a $C_1-C_{20}$ linear or branched hydrocarbyl or hydrocarbylsilyl substituent. Additionally, the two R's may connect to form a substituted or unsubstituted, halogenated or non-halogenated, $C_2-C_{20}$ cycloaliphatic, $C_2-C_{10}$ hyrodcarbyl or $C_2-C_{10}$ hydrocarbylsilyl. R' is a $C_1-C_{20}$ hydrocarbyl or halogenated hydrocarbyl. Suitable fluoroaryl substituents on the nitrogen atom can be substituted or unsubstituted phenyl, or biphenyl. The substitutions can be on ring carbon atoms, or the ring carbon atom itself can be substituted, yielding a hetero-aromatic ring. Some embodiments use a perfluorinated aromatic ring. The R' substituent may be a linear or branched, fluorinated or unfluorinated alkyl or alkenyl substituent. Some embodiments are based on the following fluoroaryl-ligand-substituted amines, ArF—$NR_2$, where the fluoroaryl ligand, ArF, may be a fluoro- or perfluoro-substituted aryl. R represents substituted or unsubstituted, alkyl or cycloalkyl groups as defined above, which may be selected independently. Some embodiments employ the following cyclic secondary amines: N-pentafluorophenylpyrrolidine, N-paranonafluorobiphenylpyrolidine,
N-tridecafluoroterphenylpyrolidine,
N-pentafluorophenylpyrrole,
N-paranonafluorobiphenylpyrrole,
N-tridecafluoroterphenylpyrrole,
N-pentafluorophenylpiperidine,
N-paranonafluorobiphenylpiperidine,
N-tridecafluoroterphenylpiperidine,
N-pentafluorophenylindoline,
N-paranonafluorobiphenylindoline,
N-tridecafluoroterphenylindoline,
N-pentafluorophenylindole,
N-paranonafluorobiphenylindole,
N-tridecafluoroterphenylindole,
N-pentafluorophenyazetidine,
N-paranonafluorobiphenylazetidine,
N-tridecafluoroterphenylazetidine,
N-pentafluorophenyaziridine,
N-paranonafluorobiphenylaziridine, and
N-tridecafluoroterphenylaziridine.

Effective, invention Group-13 cocatalyst complexes are, in some embodiments, derived from an ionic salt comprising a 4-coordinate, Group-13 anionic complex, represented as:

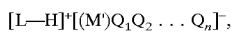

where [L—H]$^+$ is defined above, M is one or more Group-13 metal or metalloid, including boron or aluminum. Each Q is a ligand effective for providing electronic or steric effects rendering [(M')Q$_1$Q$_2$ ... Q$_n$]$^-$ suitable as a noncoordinating or weakly coordinating anion (as that is understood in the art). If an anion is noncoordinating or weakly coordinating, it is referred to in this disclosure as substantially noncoordinating, which means that it coordinates so weakly that it is labile enough to allow for olefinic or acetylenic monomer insertion during a polymerization reaction. Alternatively, a sufficient number of Q can be chosen so that [(M')Q$_1$Q$_2$ ... Q$_n$]$^-$ as a whole is effective as an NCA. Exemplary Q substituents have from 4 to 20 carbon atoms in their fused or unfused ring systems, especially from 6 to 20. Q may be substituted. These substitutions specifically include fluorinated aryl groups, perfluorinated aryl groups, and may include substituents other than fluorine substituents, such as fluorinated hydrocarbyl groups. Preferred fluorinated aryl groups include C$_6$–C$_{18}$ aryl or alkylaryl groups such as phenyl, biphenyl, napthyl and alkylated derivatives thereof. The disclosures of U.S. Pat. Nos. 5,198, 401, 5,296,433, 5,278,119, 5,447,895, 5,688,634, 5,895,771, WO 93/02099, WO 97/29845, WO 99/43717, WO 99/42467 and copending U.S. application Ser. No. 09/261,627, filed Mar. 3, 1999, and its equivalent W099/45052 are particularly instructive as to suitable Q substituents and are incorporated by reference for purposes of U.S. patent practice.

The cocatalyst complex comprising a fluoroaryl-ligand-substituted secondary amine or phosphine and a Group-13-based noncoordinating or weakly coordinating anion can generally be prepared by reacting a fluoroaryl-ligand-substituted amine compound as defined above with a strong Bronsted acid to form a protonated, fluoroaryl-ligand-substituted ammonium cation counterbalanced with the anionic conjugate base of the acid. The resulting salt, [R'$_i$ArF—ER$_2$—H]$^+$[X]$^-$, is then reacted with a Group-1 or -2 salt comprising a suitable NCA as described above, and the salt that now comprises the Bronsted acid's conjugate base and the Group-1 or –2 metal is removed. For example, lithium tetrakis(pentafluorophenyl)borate can be combined with a protonated, arylammonium chloride to yield a protonated arylammonium tetrakis(pentafluorophenyl)borate compound and LiCl, as a byproduct.

One Q group or ligand may also be connected to a functional-group-containing metal oxide, metalloid oxide, or polymeric support. See, for example, U.S. Pat. Nos. 5,427,991 and 5,939,347, each incorporated by reference for purposes of U.S. patent practice. Suitable metal or metalloid supports include all metal or metalloid oxides. Some embodiments use supports that have surface hydroxyl groups exhibiting a pKa equal to or less than that observed for amorphous silica, i.e., pKa less than or equal to about 11. Accordingly, any of the conventionally known silica support materials that retain hydroxyl groups after dehydration will function with the invention. Some embodiments employ supports such as metal-oxide, silica, silica-alumina, alumina, clay, talc, etc. Silica particles, gels and glass beads are most typical.

Polymeric supports typically contain hydroxyl functional groups. Additionally, other functional groups may be employed including any of the primary alkyl amines, secondary alkyl amines, and others, where the groups are structurally incorporated in a polymeric chain and capable of protonating and replacing one of the Group-13 anion's ligands. See, for example, the functional-group-containing polymers of U.S. Pat. No. 5,288,677, the functionalized polymers of U.S. Pat. No. 5,427,991 and the description in U.S. application Ser. No. 09/277,339, filed Mar. 26, 1999, and its equivalent WO99/50311. See also WO98/55518 where protonated ammonium salts are interspersed in polymeric beads for preparing supported olefin polymerization catalysts. All are incorporated by reference for purposes of U.S. patent practice.

Other known methods for supporting catalyst systems that have a NCA cocatalyst will also be suitable for supporting this invention's catalyst complexes. Thus, the invention catalyst complexes may also be physically deposited on or affixed to appropriate support materials. See, for example, the teachings of WO 91/09882, WO 93/11172, WO 96/35726 and U.S. Pat. Nos. 4,463,135, and 5,610,115.

Transition metal olefin polymerization catalysts that are useful with this invention include those compounds useful in traditional Ziegler-Natta polymerization and metallocene compounds similarly known to be useful in polymerization, when the invention activators can activate the catalyst precursors. These typically include Group-3–11 transition metal compounds in which at least one metal ligand can be protonated by the activators. Typically, those ligands include hydride, alkyl and silyl, and their lower-alkyl-substituted (C$_1$–C$_{10}$) derivatives. Ligands capable of being abstracted and transition metal compounds comprising them include those described in the background art, see for example U.S. Pat. No. 5,198,401 and WO 92/00333. Syntheses of these compounds are well known from the published literature. Additionally, where the metal ligands include halide, amido, or alkoxy moieties (for example, biscyclopentadienyl zirconium dichloride) that are unabstractable using invention cocatalysts, the ligands can be converted into abstractable ones through known alkylation reactions with compounds such as lithium or aluminum, hydrides or alkyls, alkylalumoxanes, or Grignard reagents, etc. See also EP-A1-0 570 982 for the reaction of organoaluminum compounds with dihalo-substituted metallocene compounds before adding activating anions. All documents are incorporated by reference for purposes of U.S. patent practice.

The patent literature contains additional descriptions for metallocene compounds that comprise, or can be alkylated to comprise, at least one ligand capable of being abstracted to form a catalytically active cation, e.g., EP-A-0 129 368, U.S. Pat. Nos. 4,871,705, 4,937,299, 5,324,800 EP-A-0 418

044, EP-A-0 591 756, WO-A-92/00333, WO-A-94/01471 and WO 97/22635. Such metallocene compounds can be described for this invention as mono- or biscyclopentadienyl-substituted, Group-3, -4, -5, or -6 compounds in which the ligands may themselves be substituted with one or more groups and may be bridged to each other, or may be bridged to the transition metal through a heteroatom. The size and constituency of the ligands and bridging elements is not critical to preparing invention catalyst systems, but should be selected in the literature-described manner to enhance polymerization activity and yield the desired polymer characteristics. When bridged to each other, the cyclopentadienyl rings (including substituted cyclopentadienyl-based fused-ring systems, such as indenyl, fluorenyl, azulenyl, or their substituted analogs) will, preferably, be lower-alkyl-substituted ($C_1$–$C_6$) in the 2 position (with or without a similar 4-position substituent in the fused-ring systems) and may additionally comprise alkyl, cycloalkyl, aryl, alkylaryl, or arylalkyl substituents: the latter as linear, branched, or cyclic structures including multi-ring structures, for example, those of U.S. Pat. Nos. 5,278,264 and 5,304,614. Those substituents should have hydrocarbyl characteristics and will typically contain up to 30 carbon atoms, but may be heteroatom-containing with 1–5 non-hydrogen/carbon atoms, e.g., N, S, O, P, Ge, B and Si. All documents are incorporated by reference for purposes of U.S. patent practice.

Metallocene compounds suitable for preparing linear polyethylene or ethylene-containing copolymers (where copolymer means formed from at least two different monomers) are essentially any of those known in the art, see again WO-A-92/00333 and U.S. Pat. Nos. 5,001,205, 5,198, 401, 5,324,800, 5,304,614 and 5,308,816, for specific listings. Selecting metallocene catalysts for making isotactic or syndiotactic polypropylene, and corresponding catalyst syntheses, are well-known in the art, both the patent and academic literature, see for example *Journal of Organometallic Chemistry* 369, 359–370 (1989). Typically, those catalysts are stereorigid, asymmetric, chiral, or bridged-chiral metallocenes. See, for example, U.S. Pat. Nos. 4,892,851, 5,017,714, 5,296,434, 5,278,264, WO-A-(PCT/US92/ 10066) WO-A-93/19103, EP-A2-0 577 581, EP-A1-0 578 838, and academic literature "The Influence of Aromatic Substituents on the Polymerization Behavior of Bridged Zirconocene Catalysts", Spaleck, W., et al., *Organometallics* 1994, 13, 954–963, and "ansa-Zirconocene Polymerization Catalysts with Annelated Ring Ligands-Effects on Catalytic Activity and Polymer Chain Lengths", Brinzinger, H., et al., *Organometallics* 1994, 13, 964–970, and documents referred to therein. Though many references listed above are directed to catalyst systems with alumoxane activators, the invention activators can activate analogous metallocenes provided that the halide-, amide-, or alkoxy-containing metal ligands (where occurring) are replaced with an abstractable ligand, for example, through alkylation reactions as described above, and another ligand is a group into which the ethylene group —C=C— may insert, for example, hydride, alkyl, or silyl. All documents are incorporated by reference for purposes of U.S. patent practice.

In some embodiments, exemplary metallocene compounds have the formula:

$$L^A L^B L^C_i MDE$$

where, $L^A$ is a substituted cyclopentadienyl or heterocyclopentadienyl ligand connected to M; $L^B$ is a member of the class of ligands defined for $L^A$, or is heteroatom ligand connected to M, $L^A$ and $L^B$ may be bridged together through a Group-14 linking group; $L^C_i$ is an optional neutral, non-oxidizing ligand connected to M (i equals 0 to 3); M is a Group-4 or -5 metal; and D and E are, independently, labile monoanionic ligands, each connected to M, and optionally bridged to each other, $L^A$, or $L^B$. D-M or E-M can be broken by abstraction. Likewise, a monomer or polymerizable macromer can insert into D-M or E-M. Labile ligands may be present in reduced number or even absent. It is believed that the reduced-valence-state compounds will react to form a catalytically active cation that is in fact substantially functionally equivalent to one made from a structurally saturated compound.

Non-limiting representative metallocene compounds include mono-cyclopentadienyl compounds such as pentamethylcyclopentadienyltitanium isopropoxide, pentamethylcyclopentadienyltribenzyl titanium, dimethylsilyltetramethylcyclopentadienyl-tert-butylamido titanium dichloride, pentamethylcyclopentadienyl titanium trimethyl, dimethylsilyltetramethylcyclopentadienyltert-butylamido zirconium dimethyl, dimethylsilyltetramethylcyclopentadienyldodecylamido hafnium dihydride, dimethylsilyltetramethylcyclopentadienyldodecylamido hafnium dimethyl; unbridged biscyclopentadienyl compounds such as bis(1,3-butyl,methylcyclopentadienyl)zirconium dimethyl, pentamethylcyclopentadienyl-cyclopentadienyl zirconium dimethyl, (tetramethylcyclopentadienyl)(n-propylcyclopetadienyl)zirconium dimethyl; bridged biscyclopentadienyl compounds such as dimethylsilylbis (tetrahydroindenyl)zirconium dichloride and silacyclobutyl (tetramethylcyclopentadienyl)(n-propylcyclopentadienyl) zirconium dimethyl; bridged bis-indenyl compounds such as dimethylsily-bisindenyl zirconium dichloride, dimethylsily-bisindenyl hafnium dimethyl, dimethylsilylbis(2-methylbenzindenyl)zirconium dichloride, dimethylsilylbis (2-methylbenzindenyl)zirconium dimethyl; and fluorenyl ligand-containing compounds, e.g., diphenylmethyl (fluorenyl)(cyclopentadienyl)zirconium dimethyl; and the additional mono- and biscyclopentadienyl compounds such as those listed and described in U.S. Pat. Nos. 5,017,714, 5,324,800 and EP-A-0 591 756. All documents are incorporated by reference for purposes of U.S. patent practice.

Representative traditional Ziegler-Natta transition metal compounds include tetrabenzyl zirconium, tetra(bis (trimethylsilyl)methyl)zirconium, oxotris (trimethylsilylmethyl)vanadium, tetrabenzyl hafnium, tetrabenzyl titanium, bis(hexamethyl-disilazido)dimethyl titanium, tris(trimethylsilylmethyl)niobium dichloride, tris (trimethylsilylmethyl)tantalum dichloride. The important polymerization features for these compositions are the abstractable ligand and the ligand into which the ethylene (olefinic) group can insert. These features enable ligand abstraction from the metal compound and the concomitant invention catalyst formation.

Additional organometallic compounds suitable as olefin polymerization catalysts in accordance with the invention will be any of those Group-3–11 that can be converted by ligand abstraction into a catalytically active cation and stabilized in that active electronic state by a noncoordinating or weakly coordinating anion that is displaceable by an olefinically unsaturated monomer such as ethylene.

Exemplary compounds include those described -in the patent literature. International patent publications WO 96/23010, WO 97/48735 and Gibson, et al., *Chem. Comm., pp.* 849–850 (1998), disclose diimine-based ligands for Group-8–10 compounds shown to be suitable for activation and olefin polymerization. See also WO 97/48735. Polymerization catalyst systems from Group-5–10 metals in which the active metal center is highly oxidized and stabilized by low coordination number, polyanionic ligand systems are described in U.S. Pat. No. 5,502,124 and its divisional U.S. Pat. No. 5,504,049. See also the Group-5 organometallic catalysts of U.S. Pat. No. 5,851,945 and the tridentate-ligand-containing Group4–9 organometallic catalysts of copending U.S. application Ser. No. 09/302243, filed Apr. 29, 1999, and its equivalent PCT/US99/09306. Group-11 catalyst precursor compounds, activable with ionizing cocatalysts, and useful for polymerization of olefins and vinyl-group-containing polar monomers are described and exemplified in WO 99/30822 and its priority document, including U.S. patent application Ser. No. 08/991,160, filed Dec. 16, 1997. Each of these documents is incorporated by reference for the purposes of U.S. patent practice.

U.S. Pat. No. 5,318,935 describes bridged and unbridged, bisamido catalyst compounds of Group-4 metals capable of polymerizing X-olefins. Bridged bis(arylamido) Group-4 compounds for olefin polymerization are described by D. H. McConville, et al., in *Organometallics* 1995, 14, 5478–5480. Synthesis methods and compound characterization are presented. Further work described bridged bis (arylamido) Group-4 compounds that are active, 1-hexene catalysts. See D. H. McConville, et al., *Macromolecules* 1996, 29, 5241–5243; see also WO98/37109. Additional compounds suitable in accordance with the invention include those described in WO 96/40805. Cationic Group-3 or Lanthanide metal complexes for olefin polymerization are disclosed in copending U.S. application Ser. No. 09/408050, filed Sep. 29, 1999, and its equivalent PCT/US99/22690. The precursor metal compounds are stabilized by a monoanionic bidentate ligand and two monoanionic ligands and are activable with invention cocatalysts. Each of these documents is incorporated by reference for the purposes of U.S. patent practice.

Additional description of suitable organometallic catalyst precursor compounds may be found in the literature, any of such will be suitable where comprising, or where capable of alkylation to comprise, ligands abstractable from organometallic compounds. See, for instance, V. C. Gibson, et al., "The Search for New-Generation Olefin Polymerization Catalysts: Life Beyond Metallocenes", *Angew. Chem. Int. Ed*, 38, 428–447 (1999), incorporated by reference for the purposes of U.S. patent practice.

When using invention catalysts, particularly when immobilized on a support, the total catalyst system may additionally comprise one or more scavenging compounds. The term "scavenging compounds" as used in this disclosure includes those compounds that effectively remove polar impurities from the reaction. All polymerization reactants can carry impurities into the reaction, particularly the solvent, monomer and catalyst feeds. These impurities degrade catalyst activity and stability. Their presence can decrease or eliminate catalytic activity, particularly with ionizing-anion-precursor-activated catalyst systems. These impurities, or poisons, include water, oxygen, metal impurities, etc. Typically, impurities are removed from the reactants before the reactants are added to the reaction vessel, but some scavenging compound will normally be used during polymerization.

The scavenging compounds will be known organometallic compounds such as the Group-13 compounds of U.S. Pat. Nos. 5,153,157, 5,241,025, 5,767,587 and WO-A-91/09882, WO-A-94/03506, WO-A-93/14132, and that of WO 95/07941. Exemplary compounds include triethyl aluminum, triethyl borane, triisobutyl aluminum, methylalumoxane, isobutyl alumoxane, and tri-n-octyl aluminum. Those scavenging compounds having bulky or $C_6$–$C_{20}$ linear hydrocarbyl substituents connected to the metal or metalloid center interact minimally with the active catalyst. Examples include triethylaluminum and bulky compounds such as triisobutylaluminum, triisoprenylaluminum, and long-chain linear-alkyl-substituted aluminum compounds, such as tri-n-hexylaluminum, tri-n-octylaluminum, or tri-n-dodecylaluminum. The scavenger that is used with invention catalysts is minimized to an activity-enhancing amount and avoided altogether if the feeds and polymerization medium are pure enough.

Invention catalyst complexes are. useful for polymerizing monomers known to be coordination polymerizable using metallocenes. Such conditions are well known and include solution, slurry, gas-phase, and high-pressure polymerization. If invention catalysts are supported, they will be particularly useful in the known operating modes employing fixed-bed, moving-bed, fluid-bed, slurry, or solution processes conducted in single, series, or parallel reactors. Additionally, pre-polymerization of supported invention catalysts can control polymer-particle morphology in usual slurry or gas phase reactions.

Liquid phase (solution, slurry, suspension, bulk phase or combinations), in high-pressure liquid phase, in supercritical fluid phase, or gas-phase processes employ different invention catalyst system embodiments. Each of these processes can also function in singular, parallel, or series reactors. The liquid processes comprise contacting the described catalyst systems with olefin monomers in suitable diluents or solvents long enough to produce invention polymers. Both aliphatic and aromatic hydrocarbyl solvents can be used with the invention processes. Hexane, cyclopentane, cyclohexane, and their alkylated derivatives are particularly useful. Other exemplary solvents include linear or cyclic aliphatic hydrocarbons having from 4 to 20 carbon atoms, preferably from 5 to 10 carbon atoms. Exemplary solvents also include 6-to-12-carbon-atom aromatic hydrocarbons. In bulk and slurry processes, the catalysts typically contact liquid monomer slurries. When that is the case, the catalyst system is usually supported. Gas-phase processes typically use a supported catalyst and are conducted in any manner known to be suitable for ethylene polymerization. Illustrative examples may be found in U.S. Pat. Nos. 4,543,399, 4,588,790, 5,028,670, 5,382,638, 5352,749, 5,408,017, 5,436,304, 5,453,471, and 5,463,999, 5,767,208 and WO 95/07942. Each is incorporated by reference for purposes of U.S. patent practice.

In some embodiments, the monomers used with the catalyst compositions described in this disclosure include 2–20-carbon-atom olefins. In other embodiment, olefin polymers prepared with invention catalysts contain at least 50 mol % of either ethylene or propylene. Thus, various ethylene or propylene polymers can be made.

Representative reaction temperatures -and pressure for different embodiments are shown in Table 1.

TABLE 1

| Reaction Temperature and Reaction Pressure | |
|---|---|
| Embodiment | Reaction Temperature in ° C. |
| A | $\leq 220$ |
| B | $\geq 40$ |
| C | $\leq 250$ |
| D | $\geq 60$ |

TABLE 1-continued

Reaction Temperature and Reaction Pressure

| Embodiment | Reaction Pressure in bar |
|---|---|
| E | ≦2500 |
| F | ≧0.1 |
| G | ≦500 |
| H | ≦1600 |
| I | ≧1.0 |
| J | ≧0.001 |

Linear polyethylene, including high- and ultra-high molecular weight polyethylenes, including both homo- and copolymers with other α-olefin monomers or α-olefinic or non-conjugated diolefins are produced by adding ethylene, and optionally one or more other monomers, to a reaction vessel under low pressure (typically <50 bar), at a typical temperature of 40–250° C. with invention catalyst that has been slurried with a solvent, such as hexane or toluene. Other α-olefins such as $C_3$–$C_{20}$ olefins, diolefins, vinyl aromatics (such as styrene) or cyclic olefins function as monomers with some of this invention's embodiments. Polymerization heat is typically removed by cooling. Gas-phase polymerization can be conducted, for example, in continuous fluid-bed, gas-phase reactors operated at 2000–3000 kPa and 60–160° C., using hydrogen as a reaction modifier (100–200 PPM), $C_4$–$C_8$ comonomer feedstream (0.5–1.2 mol %), and $C_2$ feedstream (25–35 mol %). See, U.S. Pat. Nos. 4,543,399, 4,588,790, 5,028,670 and 5,405,922 and 5,462,999, which are incorporated by reference for purposes of U.S. patent practice.

High-molecular-weight, low-crystallinity ethylene-α-olefin elastomers (including ethylene-cyclic olefin and ethylene-α-olefin-diolefin) can be prepared using invention catalysts under traditional solution polymerization processes or by introducing ethylene gas into a slurry using α-olefin or cyclic olefin or their mixtures with other compounds or monomers as diluents, which suspend invention catalysts. Typical ethylene pressures will be between 10 and 1000 psig (69–6895 kPa), and the diluent temperature will typically be between 40 and 160° C. The process can be carried out in a stirred-tank reactor, or more than one reactor operated in series or parallel. See the general disclosure of U.S. Pat. No. 5,001,205 for general process conditions. See also, international application WO 96/33227 and WO 97/22639. All documents are incorporated by reference for description of polymerization processes, metallocene selection and useful scavenging compounds.

Other olefinically unsaturated monomers besides those specifically described above may be polymerized using invention catalysts. For example, styrene, alkyl-substituted styrenes, isobutylene and other geminally disubstituted olefins, ethylidene norbornene, norbornadiene, dicyclopentadiene, and other olefinically unsaturated monomers, including other cyclic olefins, such as cyclopentene, norbornene, and alkyl-substituted norbornenes can all be polymerized with invention catalysts. See, for example, U.S. Pat. Nos. 5,635,573, and 5,763,556. Additionally, α-olefinic marchers of up to more than 1000 mer units may also be polymerized yielding branch-containing olefin polymers.

Invention catalyst compositions can be used as described above for polymerization individually or can be mixed to prepare polymer blends with other olefin polymerization catalysts. Catalyst blend and monomer selection allows blend preparation under conditions analogous to those using individual catalysts. Polymers having increased MWD for improved processing and other traditional benefits available from polymers made with mixed catalyst systems can thus be achieved.

Polyethylene homo- or copolymer may advantageously have a density of from 0.87 to 0.95. A density of at least 0.88, preferably at least 0.90 and especially at least 0.915 may be used. The density may be less than 0.94 and preferably less than 0.925. The MI may vary from 0.1 to 10 and especially 0.5 to 8 to perform film formation in cast and blown film processes. The propylene homo- and copolymers may be made with metallocenes that permit the formation of isotactic, syndiotactic or atactic sequences and may have an MFR of from 0.1 to 800 and a comonomer content of from 0 to 15 mol % with melting points of from 170 to 90° C., where the polypropylene co-monomers may be selected from one or more of ethylene, $C_4$–$C_{12}$ α-olefins, and $C_5$–$C_{12}$ non-conjugated diolefins.

The blended polymer formation can be achieved ex situ through mechanical blending or in situ with a mixed catalyst system. It is generally believed that in situ blending provides a more homogeneous product and allows the blend to be produced in one step. In in situ blending, more than one catalyst is combined in the same reactor to simultaneously produce different polymer products. This method requires additional catalyst synthesis. It also requires that the various catalyst components be matched for their activities, the polymer products they generate at specific conditions, and their response to changes in polymerization conditions.

Compounds Useful in the Practice of this Invention
Exemplary Fluoroaryl-ligand-substituted Amines and Phosphines (1-fluorobiphenyl)(3-ethylheptyl)(ethyl)amine; (1-fluorobiphenyl)(butyl)(fluoromethyl)amine; (1-fluorobiphenyl)(difluoromethyl)amine; (1-fluorobiphenyl)(methyl)(perfluoroethyl)amine; (1-fluorobiphenyl)(propyl)(hexyl)amine; (1-fluorobiphenyl)(methyl)(hexafluorononyl)amine; (1-fluorophenyl)(2-methylpentyl)(perfluoroethyl)amine; (1-fluorophenyl)(hexyl)(perfluoromethyl)amine; (1-fluorophenyl)(nonyl)(perfluoroethyl)amine; (1-fluorophenyl)(methyl)(fluoromethyl)amine; (1-fluorophenyl)(fluoromethyl)(butyl)amine; (1-fluorophenyl)(perfluoroethyl)(methyl)amine; (1-fluorophenyl)(methyl)(perfluorobutyl)amine; (1-fluorophenyl)(hexyl)(perfluorobutyl)amine; (1-fluorophenyl)(methyl)(propyl)amine; (2,3-difluorophenyl)(ethyl)(fluoromethyl)amine; (2,3-difluorophenyl)(perfluorobutyl)(fluoromethyl)amine; (2,3-difluorophenyl)(perfluoromethyl)(methyl)amine; (2,3-difluorophenyl)(nonyl)(perfluoroethyl)amine; (2,3-difluorophenyl)(nonyl)(propyl)amine; (2,3-difluorophenyl)(ethyl)(perfluorobutyl)amine; (2,3-difluorophenyl)(nonyl)(propyl)amine; (2,3-difluorophenyl)(perfluoroethyl)(2-methyl-5-propyl-heptyl)amine; (2,3-difluorophenyl)(2-methylpentyl)(perfluoroethyl)amine; (2,3-difluorophenyl)(methyl)(2-methylpentyl)amine; (2,3-difluorophenyl)(propyl)(hexyl)amine; (2,4-difluorophenyl)(perfluoromethyl)(2-methyl-5-propyl-heptyl)amine; (2,4-difluorophenyl)(3-ethyiheptyl)(perfluoroethyl)amine; (2,4-difluorophenyl)(perfluoroethyl)(fluoromethyl)amine; (2,4-difluorophenyl)(nonyl)(perfluorobutyl)amine; (2,4-difluorophenyl)(hexyl)(fluoromethyl)amine; (2,4-difluorophenyl)(ethyl)(butyl)amine; (2,4-difluorophenyl)(pefluoroethyl)(butyl)amine; (2,4-difluorophenyl)(dimethyl)amine; (2,4-difluorophenyl)(ethyl)(propyl)amine; (2,4-difluorophenyl)(2-methyl-5-propyl-heptyl)(ethyl)amine; (2,4-difluorophenyl)(methyl)(ethyl)amine; (2,4- difluorophenyl)(3-ethylheptyl)(hexyl)amine; (2,4-difluorophenyl)(hexyl)(perfluoroethyl)amine; (2,5-difluorophenyl)(difluoromethyl)amine; (2,5-difluorophenyl)(perfluoroethyl)(fluorobutyl)amine; (2,5-difluorophenyl)(propyl)(nonyl)amine; (2,5-difluorophenyl)(2-methylpentyl)(ethyl)amine; (2,5-difluorophenyl) bis(2,2,2-trifluoroethyl)amine; (2,5-difluorophenyl)(propyl)(2-methyl-5-propyl-heptyl)amine; (2,5-difluorophenyl)(butyl)(2-methyl-5-propyl-heptyl)amine; (2,5-difluorophenyl)(propyl)(fluoromethyl)amine; (2,5-difluorophenyl)(perfluoroethyl)(ethyl)amine; (2-methyl-6-perfluoromethyl-perfluorobiphenyl)(fluoromethyl)(fluorobutyl)amine; (2-methyl-6-perfluoromethyl-perfluorobiphenyl)(fluoromethyl)(methyl)amine; (2-methyl-6-perfluoromethyl-perfluorobiphenyl)(hexyl)(methyl)amine; (2-methyl-6-perfluoromethyl-perfluorobiphenyl)(methyl)(perfluoroethyl)amine; (2-methyl-6-perfluoromethyl-perfluorobiphenyl)(perfluoroethyl)(butyl)amine; (2-methyl-6-perfluoromethyl-perfluorobiphenyl)(butyl)(perfluoromethyl)amine; (2-methyl-6-perfluoromethyl-perfluorobiphenyl)(3-ethylheptyl)(perfluoroethyl)amine; (2-methyl-6-perfluoromethyl-perfluorobiphenyl)(perfluoromethyl)(hexyl)amine; (2-methyl-6-perfluoromethyl-perfluorobiphenyl)(fluoromethyl)(nonyl)amine; (2-methyl-6-perfluoromethyl-perfluorobiphenyl)(methyl)(hexyl)amine; (2-methyl-6-perfluoromethyl-perfluorobiphenyl)(hexyl)(butyl)amine; (2-methyl-6-perfluoromethyl-perfluorobiphenyl)(difluorobutyl)amine; (2-methyl-6-perfluoromethyl-perfluorobiphenyl)(butyl)(perfluorobutyl)amine; (2-methyl-6-perfluoromethyl-perfluorobiphenyl)(dihexyl)amine; (2-methyl-6-perfluoromethyl-perfluorobiphenyl)(butyl)(propyl)amine; (2-methyl-6-perfluoromethyl-perfluorobiphenyl)(fluoromethyl)(ethyl)amine; (2-perfluoromethyl-6-perfluoroethyl-perfluorobiphenyl)(hexafluorononyl)(fluoromethyl)amine; (2-perfluoromethyl-6-perfluoroethyl-perfluorobiphenyl)(difluorobutyl)amine; (2-perfluoromethyl-6-perfluoroethyl-perfluorobiphenyl)(methyl)(ethyl)amine; (2-perfluoromethyl-6-perfluoroethyl-perfluorobiphenyl)(3-ethylheptyl)(methyl)amine; (2-perfluoromethyl-6-perfluoroethyl-perfluorobiphenyl)(perfluoroethyl)(fluoromethyl)amine; (2-perfluoromethyl-6-perfluoroethyl-perfluorobiphenyl)(dihexyl)amine; (2-perfluoromethyl-6-perfluoroethyl-perfluorobiphenyl)(perfluorobutyl)(butyl)amine; (2-perfluoromethyl-6-perfluoroethyl-perfluorobiphenyl)(perfluorobutyl)(butyl)amine; (2-perfluoromethyl-6-perfluoroethyl-perfluorobiphenyl)(perfluorobutyl)(ethyl)amine; (2-perfluoromethyl-6-perfluoroethyl-perfluorobiphenyl)(butyl)(methyl)amine; (2-perfluoromethyl-6-perfluoroethyl-perfluorobiphenyl)(dipropyl)amine; (3-methyl-perfluorophenyl)(hexyl)(perfluoroethyl)amine; (3-methyl-perfluorophenyl)(hexafluorononyl)(fluoromethyl)amine; (3-methyl-perfluorophenyl)(ethyl)(2-methylpentyl)amine; (3-methyl-perfluorophenyl)(ethyl)(propyl)amine; (3-methyl-perfluorophenyl)(fluoromethyl)(fluoroethyl)amine; (3-methyl-perfluorophenyl)(propyl)(fluoromethyl)amine; (3-methyl-perfluorophenyl)(hexyl)(perfluoromethyl)amine; (3-methyl-perfluorophenyl)(butyl)(ethyl)amine; (3-methyl-perfluorophenyl)(propyl)(fluoromethyl)amine; (3-methyl-perfluorophenyl)(hexyl)(propyl)amine; (3-perfluoroethyl-trifluorophenyl)(propyl)(fluoromethyl)amine; (3-perfluoroethyl-trifluorophenyl)(hexyl)(perfluoroethyl)amine; (3-perfluoroethyl-trifluorophenyl)(perfluoroethyl)(fluoromethyl)amine; (3-perfluoroethyl-trifluorophenyl)(perfluorobutyl)(hexyl)amine; (3-perfluoroethyl-trifluorophenyl)(ethyl)(perfluorobutyl)amine; (3-perfluoroethyl-trifluorophenyl)(dipropyl)amine; (3-perfluoroethyl-trifluorophenyl)(methyl)(hexafluorononyl)amine; (3-perfluoroethyl-trifluorophenyl)(perfluoroethyl)(propyl)amine; (3-perfluoroethyl-trifluorophenyl)(fluoromethyl)(butyl)amine; (3-perfluoroethyl-trifluorophenyl)(perfluorobutyl)(2-methylpentyl)amine; (3-perfluoroethyl-trifluorophenyl)(perfluoromethyl)(ethyl)amine; (3-perfluoroethyl-trifluorophenyl)(perfluorobutyl)(propyl)amine; (3-perfluoroethyl-trifluorophenyl)(propyl)(butyl)amine; (3-perfluoroethyl-trifluorophenyl)(hexafluorononyl)(hexyl)amine; (3-perfluoromethyl-trifluorophenyl)(hexafluorononyl)(butyl)amine; (3-perfluoromethyl-trifluorophenyl)(fluoromethyl)(propyl)amine; (3-perfluoromethyl-trifluorophenyl)(ethyl)(2-methylpentyl)amine; (3-perfluoromethyl-trifluorophenyl)(perfluorobutyl)(propyl)amine; (3-perfluoromethyl-trifluorophenyl)(ethyl)(fluoromethyl)amine; (3-perfluoromethyl-trifluorophenyl)(fluoromethyl)(methyl)amine; (3-perfluoromethyl-trifluorophenyl)(propyl)(ethyl)amine; (3-perfluoromethyl-trifluorophenyl)(butyl)(perfluoroethyl)amine; (3-perfluoromethyl-trifluorophenyl)(hexyl)(fluoromethyl)amine; (biphenyl)(nonyl)(perfluoroethyl)amine; (biphenyl)(2-methyl-5-propyl-heptyl)(perfluoroethyl)amine; (biphenyl)(propyl)(ethyl)amine; (biphenyl)(ethyl)(propyl)amine; (biphenyl)(ethyl)(fluoromethyl)amine; (biphenyl)(butyl)(ethyl)amine; (biphenyl)(ethyl)(butyl)amine; (biphenyl)(fluoromethyl)(methyl)amine; (biphenyl)(perfluoroethyl)(hexyl)amine; (biphenyl)(butyl)(ethyl)amine; (biphenyl)(methyl)(nonyl)amine; (biphenyl)(2-methylpentyl)(perfluorobutyl)amine; (biphenyl)(propyl)(fluoromethyl)amine; (biphenyl)(perfluoroethyl)(propyl)amine; (biphenyl)(perfluoromethyl)(ethyl)amine; (biphenyl)(perfluoromethyl)(propyl)amine; (biphenyl)(dimethyl)amine; (biphenyl)(methyl)(perfluorobutyl)amine; (biphenyl)(fluoromethyl)(3-ethylheptyl)amine; (biphenyl)(methyl)(ethyl)amine; (biphenyl)(2-methylpentyl)(perfluorobutyl)amine; (biphenyl)(propyl)(methyl)amine; (biphenyl)(ethyl)(perfluoroethyl)amine; (biphenyl)(2-methyl-5-propyl-heptyl)(perfluorobutyl)amine; (biphenyl)(fluoromethyl)(2-methyl-5-propyl-heptyl)amine; (biphenyl)(dimethyl)amine; (biphenyl)(perfluoroethyl)(2-methylpropyl-heptyl)amine; (biphenyl)(propyl)(perfluoroethyl)amine; (biphenyl)(perfluorobutyl)(3-ethylheptyl)amine; (biphenyl)(butyl)(3-ethylheptyl)amine; (biphenyl)(difluoromethyl)amine; (biphenyl)(propyl)(methyl)amine; (biphenyl)(perfluoroethyl)(hexyl)amine; (biphenyl)(propyl)(3-ethylheptyl)amine; (hexafluorobiphenyl)(butyl)(fluoromethyl)amine; (hexafluorobiphenyl)(perfluoroethyl)(nonyl)amine; (hexafluorobiphenyl)(ethyl)(hexyl)amine; (hexafluorobiphenyl)(hexyl)(2-methyl-5-propyl-heptyl)amine; (octafluorobiphenyl)(ethyl)(perfluorobutyl)amine; (octafluorobiphenyl)(propyl)(perfluoromethyl)amine; (octafluorobiphenyl)(2-methylpentyl)(perfluoromethyl)amine; (octafluorobiphenyl)(butyl)(perfluoroethyl)amine; (octafluorobiphenyl)(dipropyl)amine; (octafluorobiphenyl)(2-methyl-5-propyl-heptyl)(ethyl)amine; (octafluorobiphenyl)(ethyl)(propyl)amine; (octafluorobiphenyl)(hexafluorononyl)(2-methyl-5-propyl-heptyl)amine; (octafluorobiphenyl)(perfluoromethyl)(fluorobutyl)amine; (perfluorobiphenyl)(perfluoromethyl)(butyl)amine; (perfluorobiphenyl)(butyl)(hexafluorononyl)amine; (perfluorobiphenyl)(ethyl)(2-methylpentyl)amine; (perfluorobiphenyl)(ethyl)(hexyl)amine; (perfluorobiphenyl)(ethyl)(perfluoromethyl)amine; (perfluorobiphenyl)(propyl)(perfluoroethyl)amine; (perfluorobiphenyl)(hexyl)(methyl)amine;

(perfluorobiphenyl)(2-methylpentyl)(perfluoromethyl) amine; (perfluorobiphenyl)(methyl)(fluoromethyl)amine; (perfluorobiphenyl)(dimethyl)amine; (perfluorobiphenyl) (fluoromethyl)amine; (perfluorobiphenyl)(nonyl)(ethyl) amine; (perfluorobiphenyl)(nonyl)(fluoromethyl)amine; (perfluorobiphenyl)(perfluorobutyl)(fluoroethyl)amine; (perfluorobiphenyl)(dibutyl)amine; (perfluorobiphenyl) (perfluoroethyl)(propyl)amine; (perfluorobiphenyl)(ethyl) (butyl)amine; (perfluorobiphenyl)(fluoromethyl)(propyl) amine; (perfluorobiphenyl)(diethyl)amine; (perfluorobiphenyl)(perfluoroethyl)(hexyl)amine; (perfluorobiphenyl)(nonyl)(perfluoromethyl)amine; (perfluorobiphenyl)(hexyl)(butyl)amine; (perfluorobiphenyl)(nonyl)(fluoromethyl)amine; (perfluorobiphenyl)(perfluorobutyl)(methyl)amine; (perfluorobiphenyl)(3-ethylheptyl)(methyl)amine; (perfluorobiphenyl)(nonyl)(propyl)amine; (perfluorobiphenyl)(hexyl)(propyl)amine; (perfluorobiphenyl)(perfluorobutyl)(fluoromethyl)amine; (perfluorobiphenyl)(propyl)(perfluoromethyl)amine; (perfluorobiphenyl)(butyl)(perfluoromethyl)amine; (perfluorobiphenyl)(dibutyl)amine; (perfluorobiphenyl) (ethyl)(propyl)amine; (perfluorobiphenyl)(butyl)(methyl) amine; (perfluorobiphenyl)(propyl)(hexyl)amine; (perfluorobiphenyl)(fluoromethyl)(fluoromethyl)amine; (perfluorobiphenyl)(nonyl)(propyl)amine; (perfluorobiphenyl)(fluoromethyl)(methyl)amine; (perfluorobiphenyl)(fluoromethyl)(2-methylpentyl)amine; (perfluorobiphenyl)(butyl)(fluoromethyl)amine; (perfluorobiphenyl)(perfluoromethyl)(propyl)amine; (perfluorobiphenyl)(3-ethylheptyl)(perfluorobutyl)amine; (perfluorobiphenyl)(perfluoromethyl)(fluoroethyl)amine; (perfluorobiphenyl)(hexyl)(propyl)amine; (perfluorobiphenyl)(propyl)(butyl)amine; (perfluorobiphenyl)(butyl)(perfluoromethyl)amine; (perfluorobiphenyl)(perfluoroethyl)(fluoromethyl)amine; (perfluorobiphenyl)(hexafluorononyl)(methyl)amine; (perfluorobiphenyl)(fluoromethyl)(ethyl)amine; (perfluorobiphenyl)(perfluoroethyl)(2-methyl-5-propyl-heptyl)amine; (perfluorobiphenyl)(perfluorobutyl) (fluoromethyl)amine; (perfluorobiphenyl)(perfluorobutyl) (fluoromethyl)amine; (perfluorobiphenyl)(perfluorobutyl) (fluoromethyl)amine; (perfluorobiphenyl)(hexyl)(butyl) amine; (perfluorobiphenyl)(propyl)(butyl)amine; (perfluorobiphenyl)(hexafluorononyl)(propyl)amine; (perfluorobiphenyl)(perfluoroethyl)(methyl)amine; (perfluorobiphenyl)(hexyl)(perfluoromethyl)amine; (perfluorobiphenyl)(ethyl)(perfluorobutyl)amine; (perfluorobiphenyl)(methyl)(3-ethylheptyl)amine; (perfluorobiphenyl)(propyl)(ethyl)amine; (perfluorobiphenyl)(nonyl)(methyl)amine; (perfluorobiphenyl)(perfluoroethyl)(fluorobutyl)amine; (perfluorobiphenyl)(perfluoroethyl)(methyl)amine; (perfluorobiphenyl)(difluoromethyl)amine; (perfluorobiphenyl)(fluoromethyl)(fluoromethyl)amine; (perfluorobiphenyl)(perfluoromethyl)(hexyl)amine; (perfluorobiphenyl)(propyl)(perfluoromethyl)amine; (perfluorobiphenyl)(fluoromethyl)amine; (perfluorobiphenyl)(dibutyl)amine; (perfluorobiphenyl) (hexafluorononyl)(fluorobutyl)amine; (perfluorobiphenyl) (perfluorobutyl)(hexyl)amine; (perfluorophenyl) (fluoromethyl)(hexyl)amine; (perfluorophenyl)(ethyl) (hexyl)amine; (perfluorophenyl)(ethyl)(hexyl)amine; (perfluorophenyl)(fluoromethyl)(methyl)amine; (perfluorophenyl)(butyl)(perfluoroethyl)amine; (perfluorophenyl)(ethyl)(perfluorobutyl)amine; (perfluorophenyl)(dipropyl)amine; (perfluorophenyl) (propyl)(ethyl)amine; (perfluorophenyl)(dimethyl)amine; (perfluorophenyl)(perfluoromethyl)(methyl)amine; (perfluorophenyl)(butyl)(hexafluorononyl)amine; (perfluorophenyl)(2-methyl-5-propyl-heptyl)(hexyl)amine; (perfluorophenyl)(butyl)(methyl)amine; (perfluorophenyl) (butyl)(fluoromethyl)amine; (perfluorophenyl)(hexyl) (nonyl)amine; (perfluorophenyl)(perfluorobutyl)(propyl) amine; (perfluorophenyl)(hexyl)(perfluoromethyl)amine; (perfluorophenyl)(fluoromethyl)(methyl)amine; (perfluorophenyl)(2-methylpentyl)(ethyl)amine; (perfluorophenyl)(propyl)(methyl)amine; (perfluorophenyl) (propyl)(2-methylpentyl)amine; (perfluorophenyl) (perfluoroethyl)(ethyl)amine; (perfluorophenyl) (perfluorobutyl)(propyl)amine; (perfluorophenyl)(methyl) (perfluoroethyl)amine; (perfluorophenyl)(methyl)(ethyl) amine;(perfluorophenyl)(methyl)(ethyl)amine; (perfluorophenyl)(perfluoroethyl)(fluorobutyl)amine; (perfluorophenyl)(3-ethylheptyl)(butyl)amine; (perfluorophenyl)(perfluorobutyl)(fluoroethyl)amine; (perfluorophenyl)(propyl)(3-ethylheptyl)amine; (perfluorophenyl)(perfluoromethyl)(3-ethylheptyl)amine; (perfluorophenyl)(3-ethylheptyl)(hexyl)amine; (perfluorophenyl)(methyl)(2-methyl-5-propyl-heptyl) amine; (perfluorophenyl)(perfluoroethyl)(nonyl)amine; (perfluorophenyl)(propyl)(methyl)amine; (perfluorophenyl) (perfluoroethyl)(hexyl)amine; (perfluorophenyl) (perfluorobutyl)(fluoromethyl)amine; (perfluorophenyl) (perfluorobutyl)(fluoromethyl)amine; (perfluorophenyl) (propyl)(nonyl)amine; (perfluorophenyl)(perfluoromethyl) (fluoromethyl)amine, (perfluorophenyl)(hexyl) (perfluoroethyl)amine; (perfluorophenyl)(perfluoromethyl) (methyl)amine; (perfluorophenyl)(fluoromethyl) (fluoroethyl)amine; (perfluorophenyl)(methyl) (perfluoromethyl)amine; (perfluorophenyl)(propyl)(hexyl) amine; (perfluorophenyl)(methyl)(butyl)amine; (perfluorophenyl)(butyl)(methyl)amine; (perfluorophenyl) (perfluoromethyl)(hexyl)amine; (perfluorophenyl)(butyl) (methyl)amine; (perfluorophenyl)(2-methyl-5-propyl-heptyl)(perfluoromethyl)amine; (perfluorophenyl)(2-methyl-5-propyl-heptyl)(methyl)amine; (perfluorophenyl) (fluoromethyl)(fluorobutyl)amine; (perfluorophenyl)(butyl) (3-ethylheptyl)amine; (perfluorophenyl)(nonyl) (perfluoromethyl)amine; (perfluorophenyl)(perfluorobutyl) (hexyl)amine; (perfluorophenyl)(dimethyl)amine; (perfluorophenyl)(fluoromethyl)(fluoroethyl)amine; (perfluorophenyl)(methyl)(perfluoromethyl)amine; (perfluorophenyl)(perfluoromethyl)(hexyl)amine; (perfluorophenyl)(ethyl)(fluoromethyl)amine; (perfluorophenyl)(propyl)(3-ethylheptyl)amine; (perfluorophenyl)(ethyl)(fluoromethyl)amine; (perfluorophenyl)(difluoromethyl)amine; (perfluorophenyl) (perfluorobutyl)(hexyl)amine; (perfluorophenyl) (fluoromethyl)(fluoromethyl)amine; (perfluorophenyl) (perfluoromethyl)(fluorobutyl)amine; (perfluorophenyl) (fluoromethyl)(methyl)amine; (perfluorophenyl)(hexyl) (perfluoroethyl)amine; (perfluorophenyl)(propyl) (perfluorobutyl)amine; (perfluorophenyl)(fluoromethyl) (fluoroethyl)amine; (perfluorophenyl)(methyl)(butyl)amine; (perfluorophenyl)(hexyl)(perfluorobutyl)amine; (perfluorophenyl)(hexyl)(fluoromethyl)amine; (perfluorophenyl)(methyl)(hexyl)amine; (perfluorophenyl) (difluoromethyl)amine; (phenyl)(fluoromethyl) (perfluorobutyl)amine; (phenyl)(3-ethylheptyl)(nonyl) amine; (phenyl)(perfluorobutyl)(methyl)amine; (phenyl) (dipropyl)amine; (phenyl)(propyl)(hexyl)amine; (phenyl) (perfluoromethyl)(nonyl)amine; (phenyl)(ethyl)(2-methylpentyl)amine; (phenyl)(fluoromethyl)(hexyl)amine;

(phenyl)(butyl)(perfluorobutyl)amine; (phenyl)(dipropyl)amine; (phenyl)(fluoromethyl)(methyl)amine; (phenyl)(fluoromethyl)(methyl)amine; (phenyl)(perfluorobutyl)(propyl)amine; (phenyl)(methyl)(2-methylpentyl)amine; (phenyl)(butyl)(hexyl)amine; (phenyl)(hexyl)(fluoromethyl)amine; (phenyl)(perfluorobutyl)(ethyl)amine; (phenyl)(perfluoromethyl)(propyl)amine; (phenyl)(fluoromethyl)(perfluoroethyl)amine; (phenyl)(ethyl)(butyl)amine; (phenyl)(perfluoroethyl)(hexyl)amine; (phenyl)(2-methylpentyl)(methyl)amine; (phenyl)(propyl)(perfluorobutyl)amine; (phenyl)(ethyl)(methyl)amine; (phenyl)(perfluorobutyl)(methyl)amine; (phenyl)(fluoromethyl)(2-methyl-5-propyl-heptyl)amine; (phenyl)(butyl)(perfluoroethyl)amine; (phenyl)(perfluoroethyl)(hexyl)amine; (phenyl)(fluoromethyl)(perfluorobutyl)amine; (phenyl)(fluoromethyl)(2-methyl-5-propyl-heptyl)amine; (phenyl)(perfluorobutyl)(ethyl)amine; (phenyl)(ethyl)(perfluoroethyl)amine; (phenyl)(ethyl)(methyl)amine; (tetrafluorophenyl)(dipropyl)amine; (tetrafluorophenyl)(butyl)(methyl)amine; (tetrafluorophenyl)(propyl)(fluoromethyl)amine; (tetrafluorophenyl)(fluoromethyl)(ethyl)amine; (tetrafluorophenyl)(butyl)(perfluoroethyl)amine; (tetrafluorophenyl)(ethyl)(propyl)amine; (tetrafluorophenyl)(ethyl)(fluoromethyl)amine; (1-fluorobiphenyl)(ethyl)(perfluorobutyl)phosphine; (1-fluorobiphenyl)(di3-ethylheptyl)phosphine; (1-fluorobiphenyl)(perfluoroethyl)(propyl)phosphine; (1-fluorobiphenyl)(dibutyl)phosphine; (1-fluorobiphenyl)(ethyl)(hexyl)phosphine; (1-fluorobiphenyl)(methyl)(perfluoromethyl)phosphine; (1-fluorobiphenyl)(3-ethylheptyl)(hexyl)phosphine; (1-fluorobiphenyl)(fluoromethyl)(butyl)phosphine; (1-fluorobiphenyl)(3-ethylheptyl)(butyl)phosphine; (1-fluorophenyl)(propyl)(perfluoroethyl)phosphine; (1-fluorophenyl)(propyl)(butyl)phosphine; (1-fluorophenyl)(perfluoroethyl)(methyl)phosphine; (1-fluorophenyl)(hexyl)(2-methyl-5-propyl-heptyl)phosphine; (2,3-difluorophenyl)(propyl)(ethyl)phosphine; (2,3-difluorophenyl)(methyl)(perfluoroethyl)phosphine; (2,3-difluorophenyl)(butyl)(propyl)phosphine; (2,3-difluorophenyl)(difluoromethyl)phosphine; (2,3-difluorophenyl)(perfluorobutyl)(ethyl)phosphine; (2,4-difluorophenyl)(butyl)(hexyl)phosphine; (2,4-difluorophenyl)(hexyl)(perfluoromethyl)phosphine; (2,4-difluorophenyl)(propyl)(butyl)phosphine; (2,4-difluorophenyl)(hexyl)(propyl)phosphine; (2,4-difluorophenyl)(2-methyl-5-propyl-heptyl)(ethyl)phosphine; (2,4-difluorophenyl)(dimethyl)phosphine; (2,5-difluorophenyl)(2-methylpentyl)(ethyl)phosphine; (2,5-difluorophenyl)(butyl)(fluoromethyl)phosphine; (2-methyl-6-perfluoromethyl-perfluorobiphenyl)(propyl)(methyl)phosphine; (2-methyl-6-perfluoromethyl-perfluorobiphenyl)(2-methyl-5-propyl-heptyl)(hexyl)phosphine; (2-methyl-6-perfluoromethyl-perfluorobiphenyl)(2-methylpentyl)(methyl)phosphine; (2-perfluoromethyl-6-perfluoromethyl-perfluorobiphenyl)(propyl)(fluoromethyl)phosphine; (2-perfluoromethyl-6-perfluoroethyl-perfluorobiphenyl)(butyl)(ethyl)phosphine; (2-perfluoromethyl-6-perfluoromethyl-perfluorobiphenyl)(perfluoroethyl)(fluoromethyl)phosphine; (2-perfluoromethyl-6-perfluoromethyl-perfluorobiphenyl)(propyl)(methyl)phosphine; (2-perfluoromethyl-6-perfluoroethyl-perfluorobiphenyl)(hexyl)(2-methylpentyl)phosphine; (3-methyl-perfluorophenyl)(2-methyl-5-propyl-heptyl)(fluoromethyl)phosphine; (3-methyl-perfluorophenyl)(methyl)(propyl)phosphine; (3-methyl-perfluorophenyl)(methyl)(fluoromethyl)phosphine; (3-methyl-perfluorophenyl)(fluoromethyl)(butyl)phosphine; (3-methyl-perfluorophenyl)(3-ethylheptyl)(hexafluorononyl)phosphine; (3-methyl-perfluorophenyl)(perfluoroethyl)(fluoromethyl)phosphine; (3-perfluoroethyl-trifluorophenyl)(hexyl)(ethyl)phosphine; (3-perfluoroethyl-trifluorophenyl)(perfluoroethyl)(propyl)phosphine; (3-perfluoroethyl-trifluorophenyl) bis(2,2,2-trifluoroethyl)phosphine; (3-perfluoroethyl-trifluorophenyl)(methyl)(hexyl)phosphine; (3-perfluoroethyl-trifluorophenyl)(diethyl)phosphine; (3-perfluoroethyl-trifluorophenyl)(hexafluorononyl)(fluoroethyl)phosphine; (3-perfluoroethyl-trifluorophenyl)(hexafluorononyl)(butyl)phosphine; (3-perfluoromethyl-trifluorophenyl)(ethyl)(fluoromethyl)phosphine; (3-perfluoromethyl-trifluorophenyl)(perfluoroethyl)(hexafluorononyl)phosphine; (3-perfluoromethyl-trifluorophenyl)(hexyl)(ethyl)phosphine; (3-perfluoromethyl-trifluorophenyl)(hexyl)(hexafluorononyl)phosphine; (3-perfluoromethyl-trifluorophenyl)(perfluoroethyl)(butyl)phosphine; (3-perfluoromethyltrifluorophenyl)(peflurobutyl)(fluoromethyl)phosphine; (3-perfluoromethyl-trifluorophenyl)(fluoromethyl)(butyl)phosphine; (biphenyl)(perfluorobutyl)(fluoroethyl)phosphine; (biphenyl)(hexafluorononyl)(butyl)phosphine; (biphenyl)(methyl)(fluoromethyl)phosphine; (biphenyl)(perfluoroethyl)(perfluoromethyl)phosphine; (biphenyl)(butyl)(fluoromethyl)phosphine; (biphenyl)(hexafluorononyl)(hexyl)phosphine; (biphenyl)(methyl)(hexafluorononyl)phosphine; (biphenyl)(perfluorobutyl)(fluoromethyl)phosphine; (hexafluorobiphenyl)(propyl)(ethyl)phosphine; (hexafluorobiphenyl)(methyl)(propyl)phosphine; (hexafluorobiphenyl)(fluoromethyl)(fluoroethyl)phosphine; (perfluorobiphenyl)(butyl)(propyl)phosphine; (perfluorobiphenyl)(difluorobutyl)phosphine; (perfluorobiphenyl)(ethyl)(nonyl)phosphine; (perfluorobiphenyl)(fluoromethyl)(butyl)phosphine; (perfluorobiphenyl)(butyl)(perfluoromethyl)phosphine; (perfluorobiphenyl)(fluoromethyl)(fluoromethyl)phosphine; (perfluorobiphenyl)(propyl)(perfluoromethyl)phosphine; (perfluorobiphenyl)(methyl)(fluoromethyl)phosphine; (perfluorobiphenyl)(propyl)(perfluoroethyl)phosphine; (perfluorobiphenyl)(propyl)(perfluorobutyl)phosphine; (perfluorobiphenyl)(perfluorobutyl)(fluoromethyl)phosphine; (perfluorobiphenyl)(methyl)(fluoromethyl)phosphine; (perfluorobiphenyl)(butyl)(perfluorobutyl)phosphine; (perfluorobiphenyl)(difluoromethyl)phosphine; (perfluorobiphenyl)(ethyl)(butyl)phosphine; (perfluorobiphenyl)(hexyl)(perfluoroethyl)phosphine; (perfluorobiphenyl)(perfluoromethyl)(propyl)phosphine; (perfluorobiphenyl)(perfluoromethyl)(2-methylpentyl)phosphine; (perfluorobiphenyl)(nonyl)(ethyl)phosphine; (perfluorobiphenyl)bis(2,2,2-trifluoroethyl)phosphine; (perfluorobiphenyl)(methyl)(ethyl)phosphine; (perfluorobiphenyl)(butyl)(ethyl)phosphine; (perfluorobiphenyl)(2-methyl-5-propyl-heptyl)(methyl)phosphine; (perfluorobiphenyl)(fluoromethyl)(propyl)phosphine; (perfluorobiphenyl)(2-methylpentyl)(methyl)phosphine; (perfluorobiphenyl)(fluoromethyl)(hexyl)phosphine; (perfluorobiphenyl)(ethyl)(hexyl)phosphine; (perfluorobiphenyl)(dimethyl)phosphine; (perfluorophenyl)(butyl)(methyl)phosphine; (perfluorophenyl)(ethyl)(perfluorobutyl)phosphine; (perfluorophenyl)(2-methyl-5-propyl-heptyl)(ethyl)phosphine; (perfluorophenyl)(perfluoromethyl)(hexyl)phosphine; (perfluorophenyl)(hexyl)(propyl)phosphine; (perfluorophenyl)(propyl)(fluoromethyl)phosphine; (perfluorophenyl)(ethyl)(butyl)phosphine; (perfluorophenyl)(perfluoroethyl)(hexyl)

phosphine; (perfluorophenyl)(hexyl)(hexafluorononyl) phosphine; (perfluorophenyl)(fluoromethyl)phosphine; (perfluorophenyl)(perfluorobutyl)(ethyl)phosphine; (perfluorophenyl)(methyl)(propyl)phosphine; (perfluorophenyl)(perfluoroethyl)(butyl)phosphine; (perfluorophenyl)(fluoromethyl)(methyl)phosphine; (perfluorophenyl)(perfluoromethyl)(propyl)phosphine; (perfluorophenyl)(butyl)(hexafluorononyl)phosphine; (perfluorophenyl)(butyl)(2-methyl-5-propyl-heptyl) phosphine; (perfluorophenyl)(butyl)(perfluoroethyl) phosphine; (perfluorophenyl)(propyl)(3-ethylheptyl) phosphine; (perfluorophenyl)(dimethyl)phosphine; (perfluorophenyl)(ethyl)(perfluoroethyl)phosphine; (perfluorophenyl)(methyl)(butyl)phosphine; (perfluorophenyl)(butyl)(propyl)phosphine; (perfluorophenyl)(hexyl)(perfluoroethyl)phosphine; (perfluorophenyl)(fluoromethyl)(ethyl)phosphine; (perfluorophenyl)(methyl)(3-ethylheptyl)phosphine; (perfluorophenyl)(propyl)(ethyl)phosphine; (perfluorophenyl)(propyl)(hexafluorononyl)phosphine; (perfluorophenyl)(3-ethylheptyl)(propyl)phosphine; (perfluorophenyl)(hexyl)(methyl)phosphine; (perfluorophenyl)(propyl)(nonyl)phosphine; (perfluorophenyl)(perfluorobutyl)(3-ethylheptyl)phosphine; (perfluorophenyl)(butyl)(perfluoroethyl)phosphine; (perfluorophenyl)(perfluorobutyl)(fluoromethyl)phosphine; (perfluorophenyl)(fluoromethyl)(ethyl)phosphine; (perfluorophenyl)(fluoromethyl)(methyl)phosphine; (perfluorophenyl)(dinonyl)phosphine; (perfluorophenyl) (butyl)(propyl)phosphine; (perfluorophenyl) (perfluoroethyl)(fluoromethyl)phosphine; (perfluorophenyl) (perfluoroethyl)(hexyl)phosphine; (perfluorophenyl) (perfluorobutyl)(propyl)phosphine; (perfluorophenyl) (hexyl)(ethyl)phosphine; (phenyl)(perfluoromethyl) (perfluoroethyl)phosphine; (phenyl)(butyl)(fluoromethyl) phosphine; (phenyl)(propyl)(perfluoroethyl)phosphine; (phenyl)(fluoromethyl)phosphine; (phenyl)(fluoromethyl) (perfluorobutyl)phosphine; (phenyl)(ethyl) (perfluoromethyl)phosphine; (phenyl)(butyl)(hexyl) phosphine; (phenyl)(perfluoromethyl)(perfluoroethyl) phosphine; (phenyl)(propyl)(2-methyl-5-propyl-heptyl) phosphine; (phenyl)(hexyl)(fluoromethyl)phosphine; (phenyl)(ethyl)(perfluorobutyl)phosphine; (phenyl)(2-methyl-5-propyl-heptyl)(hexyl)phosphine; (phenyl) (perfluoromethyl)(fluoromethyl)phosphine; (phenyl)(3-ethylheptyl)(hexyl)phosphine; (phenyl)(2-methyl-5-propyl-heptyl)(fluoromethyl)phosphine; (phenyl)(ethyl) (perfluorobutyl)phosphine; (phenyl)(butyl)(methyl) phosphine; (tetrafluorophenyl)(hexyl)(propyl)phosphine; (tetrafluorophenyl)(butyl)(perfluoroethyl)phosphine; (tetrafluorophenyl)(hexafluorononyl)(propyl)phosphine; (tetrafluorophenyl)(butyl)(hexyl)phosphine; (tetrafluorophenyl)(butyl)(methyl)phosphine; (tetrafluorophenyl)(hexyl)(methyl)phosphine; (tetrafluorophenyl)(hexyl)(fluoromethyl)phosphine Exemplary Fluoroaryl-ligand-substituted Cyclic Amines and Phosphines N-(1-fluorobiphenyl)indole; N-(1-fluorophenyl)indole; N-(2,3difluorophenyl)indole; N-(2,4-difluorophenyl)indole; N-(2,5-difluorophenyl)indole; N-(2-methyl-6-perfluoromethyl-perfluorobiphenyl)indole; N-(2-perfluoromethyl-6-perfluoroethyl-perfluorobiphenyl)indole; N-(3-methyl-perfluorophenyl)indole; N-(3-perfluoroethyl-trifluorophenyl)indole; N-(3-perfluoromethyl-trifluorophenyl)indole; N-(biphenyl)indole; N-(hexafluorobiphenyl)indole; N-(octafluorobiphenyl) indole; N-(perfluorobiphenyl)indole; N-(perfluorophenyl) indole; N-(phenyl)indole; N-(tetrafluorophenyl)indole; N-(1-fluorobiphenyl)indoline; N-(1-fluorophenyl)indoline; N-(2,3-difluorophenyl)indoline; N-(2,4-difluorophenyl) indoline; N-(2,5-difluorophenyl)indoline; N-(2-methyl-6-perfluoromethyl-perfluorobiphenyl)indoline; N-(2-perfluoromethyl-6-perfluoroethyl-perfluorobiphenyl) indoline; N-(3-methyl-perfluorophenyl)indoline; N-(3-perfluoroethyl-trifluorophenyl)indoline; N-(3-perfluoromethyl-trifluorophenyl)indoline; N-(biphenyl) indoline; N-(hexafluorobiphenyl)indoline; N-(octafluorobiphenyl)indoline; N-(perfluorobiphenyl) indoline; N-(perfluorophenyl)indoline; N-(phenyl) indoline; N-(tetrafluorophenyl)indoline; N-(1-fluorobiphenyl)isoindoline; N-(1-fluorophenyl)isoindoline; N-(2,3-difluorophenyl)isoindoline; N-(2,4-difluorophenyl) isoindoline; N-(2,5-difluorophenyl)isoindoline; N-(2-methyl-6-perfluoromethyl-perfluorobiphenyl)isoindoline; N-(2-perfluoromethyl-6-perfluoroethyl-perfluorobiphenyl) isoindoline; N-(3-methyl-perfluorophenyl)isoindoline; N-(3-perfluoroethyl-trifluorophenyl)isoindoline; N-(3-perfluoromethyl-trifluorophenyl)isoindoline; N-(biphenyl) isoindoline; N-(hexafluorobiphenyl)isoindoline; N-(octafluorobiphenyl)isoindoline; N-perfluorobiphenyl) isoindoline; N-(perfluorophenyl)isoindoline; N-(phenyl) isoindoline; N-(tetrafluorophenyl)isoindoline; N-(1-fluorobiphenyl)phosphapyrrolidine; N-(1-fluorophenyl) phosphapyrrolidine; N-(2,3-difluorophenyl) phosphapyrrolidine; N-(2,4-difluorophenyl) phosphapyrrolidine; N-(2,5-difluorophenyl) phosphapyrrolidine; N-(2-methyl-6-perfluoromethyl-perfluorobiphenyl)phosphapyrrolidine; N-(2-perfluoromethyl-6-perfluoroethyl-perfluorobiphenyl) phosphapyrrolidine; N-(3-methyl-perfluorophenyl) phosphapyrrolidine; N-(3-perfluoroethyl-trifluorophenyl) phosphapyrrolidine; N-(3-perfluoromethyl-trifluorophenyl) phosphapyrrolidine; N-biphenyl)phosphapyrrolidine; N-(hexafluorobiphenyl)phosphapyrrolidine; N-(octafluorobiphenyl)phosphapyrrolidine; N-(perfluorobiphenyl)phosphapyrrolidine; N-(perfluorophenyl)phosphapyrrolidine; N-(phenyl) phosphapyrrolidine; N-(tetrafluorophenyl) phosphapyrrolidine; N-(1-fluorobiphenyl)phosphindole; N-(1-fluorophenyl)phosphindole; N-(2,3-difluorophenyl) phosphindole; N-(2,4-difluorophenyl)phosphindole; N-(2,5-difluorophenyl)phosphindole; N-(2-methyl-6-perfluoromethyl-perfluorobiphenyl)phosphindole; N-(2-perfluoromethyl-6-perfluoroethyl-perfluorobiphenyl) phosphindole; N-(3-methyl-perfluorophenyl)phosphindole; N-(3-perfluoroethyl-trifluorophenyl)phosphindole; N-(3-perfluoromethyl-trifluorophenyl)phosphindole; N-(biphenyl)phosphindole; N-(hexafluorobiphenyl) phosphindole; N-(octafluorobiphenyl)phosphindole; N-(perfluorobiphenyl)phosphindole; N-(perfluorophenyl) phosphindole; N-(-phenyl)phosphindole; N-(tetrafluorophenyl)phosphindole; N-(1-fluorobiphenyl) phosphindoline; N-(1-fluorophenyl)phosphindoline; N-(2,3-difluorophenyl)phosphindoline; N-(2,4-difluorophenyl) phosphindoline; N-(2,5-difluorophenyl)phosphindoline; N-(2-methyl-6-perfluoromethyl-perfluorobiphenyl) phosphindoline; N-(2-perfluoromethyl-6-perfluoroethyl-perfluorobiphenyl)phosphindoline; N-(3-methyl-perfluorophenyl)phosphindoline; N-(3-perfluoroethyl-trifluorophenyl)phosphindoline; N-(3-perfluoromethyl-trifluorophenyl)phosphindoline; N-(biphenyl) phosphindoline; N-(hexafluorobiphenyl)phosphindoline; N-(octafluorobiphenyl)phosphindoline; N-(perfluorobiphenyl)phosphindoline; N-(perfluorophenyl)

phosphindoline; N-phenyl)phosphindoline; N-(tetrafluorophenyl)phosphindoline; N-(1-fluorobiphenyl)piperidine; N-(1-fluorophenyl)piperidine; N-(2,3-difluorophenyl)piperidine; N-(2,4-difluorophenyl)piperidine; N-(2,5-difluorophenyl)piperidine; N-(2-methyl-6-perfluoromethyl-perfluorobiphenyl)piperldine; N-(2-perfluoromethyl-6-perfluoroethyl-perfluorobiphenyl)piperidine; N-(3-methyl-perfluorophenyl)piperidine; N-(3-perfluoroethyl-trifluorophenyl)piperidine; N-(3-perfluoromethyl-trifluorophenyl)piperidine; N-(biphenyl)piperidine; N-(hexafluorobiphenyl)piperidine; N-(octafluorobiphenyl)piperidine; N-(perfluorobiphenyl)piperidine; N-(perfluorophenyl)piperidine; N-phenyl)piperidine; N-(tetrafluorophenyl)piperidine; N-(1-fluorobiphenyl)pyrrole; N-(1-fluorophenyl)pyrrole; N-(2,3-difluorophenyl)pyrrole; N-(2,4-difluorophenyl)pyrrole; N-(2,5-difluorophenyl)pyrrole; N-(2-methyl-6-perfluoromethyl-perfluorobiphenyl)pyrrole; N-(2-perfluoromethyl-6-perfluoroethyl-perfluorobiphenyl)pyrrole; N-(3-methyl-perfluorophenyl)pyrrole; N-(3-perfluoroethyl-trifluorophenyl)pyrrole; N-(3-perfluoromethyl-trifluorophenyl)pyrrole; N-(biphenyl)pyrrole; N-(hexafluorobiphenyl)pyrrole; N-(octafluorobiphenyl)pyrrole; N-(perfluorobiphenyl)pyrrole; N-(perfluorophenyl)pyrrole; N-(phenyl)pyrrole; N-(tetrafluorophenyl)pyrrole; N-(1-fluorobiphenyl)pyrrolidine; N-(1-fluorophenyl)pyrrolidine; N-(2,3-difluorophenyl)pyrrolidine; N-(2,4-difluorophenyl)pyrrolidine; N-(2,5-difluorophenyl)pyrrolidine; N-(2-methyl-6-perfluoromethyl-perfluorobiphenyl)pyrrolidine; N-(2-perfluoromethyl-6-perfluoroethyl-perfluorobiphenyl)pyrrolidine; N-(3-methyl-perfluorophenyl)pyrrolidine; N-(3-perfluoroethyl-trifluorophenyl)pyrrolidine; N-(3-perfluoromethyl-trifluorophenyl)pyrrolidine; N-(biphenyl)pyrrolidine; N-(hexafluorobiphenyl)pyrrolidine; N-(octafluorobiphenyl)pyrrolidine; N-(perfluorobiphenyl)pyrrolidine; N-(perfluorophenyl)pyrrolidine; N-(phenyl)pyrrolidine; N-(tetrafluorophenyl)pyrrolidine;

Exemplary Noncoordinating Anions Suitable for Olefin Polymerization tetrakis(pentafluoronaphthyl)borate; tetrakis(2-methyl-5-propyl-heptyl)aluminate; tetrakis(2-methyl-5-propyl-heptyl)borate; tetrakis(2-methylpentyl)aluminate; tetrakis(2-methylpentyl)borate; tetrakis(3-ethylheptyl)aluminate; tetrakis(3-ethylheptyl)borate; tetrabutyl aluminate; tetrabutyl borate; tetrakis(ethylhexafluoronaphthyl)aluminate; tetrakis(ethylhexafluoronaphthyl)borate; tetrakis(heptafluorofluorenyl)aluminate; tetrakis(heptafluorofluorenyl)borate; tetraheptyl aluminate; tetraheptyl borate; tetrakis(hexafluoroindenyl)aluminate; tetrakis(hexafluoroindenyl)borate; tetrakis(hexafluoronapthyl)aluminate; tetrakis(hexafluoronapthyl)borate; tetrakis(hexafluorononyl)aluminate; tetrakis(hexafluorononyl)borate; tetrahextyl aluminate; tetrahextyl borate; tetrakis(methyloctafluorobiphenyl)aluminate; tetrakis(methyloctafluorobiphenyl)borate; tetrakis(methylperfluoronaphthyl)aluminate; tetrakis(methylperfluoronaphthyl)borate; tetranonyl aluminate; tetranonyl borate; tetrakis(octafluorobiphenyl)aluminate; tetrakis(octafluorobiphenyl)borate; tetraoctyl aluminate; tetraoctyl borate; tetrakis(pentafluoroindenyl)aluminate; tetrakis(pentafluoroindenyl)borate; tetrakis(pentafluoronaphthyl)aluminate; tetrakis(pentafluoronaphthyl)borate; tetrapentyl aluminate; tetrapentyl borate; tetraperfluoroanthracenyl aluminate; tetraperfluoroanthracenyl borate; tetrakis(perfluorobiphenyl)aluminate; tetrakis(perfluorobiphenyl)borate; tetrakis(perfluoroethylperfluorobiphenyl)aluminate; tetrakis(perfluoroethylperfluorobiphenyl)borate; tetraperfluorofluorenyl aluminate; tetraperfluorofluorenyl borate; tetrakis(perfluorohexylperfluorophenyl)aluminate; tetrakis(perfluorohexylperfluorophenyl)borate; tetraperfluoroindenyl aluminate; tetraperfluoroindenyl borate; tetrakis(perfluoromethylperfluoronaphthyl)aluminate; tetrakis(perfluoromethylperfluoronaphthyl)borate; tetrakis(perfluoronaphthyl)aluminate; tetrakis(perfluoronaphthyl)borate; tetrakis(perfluoropentylperfluorobiphenyl)aluminate; tetrakis(perfluoropentylperfluorobiphenyl)borate; tetraperfluorophenanthryl aluminate; tetraperfluorophenanthryl borate; tetraperfluorophenyl aluminate; tetraperfluorophenyl borate; tetrakis(perfluoropyrenyl)aluminate; tetrakis(perfluoropyrenyl)borate.

Exemplary Invention Group-13 Cocatalyst Complexes

[(2,4-difluorophenyl)(fluoromethyl)(ethyl)ammonium][tetraheptylaluminate]; [(3-perfluoroethyl-trifluorophenyl)(dihexyl)phosphonium][tetrakis(hexafluorononyl)borate]; [(2,3-difluorophenyl)(propyl)(methyl)ammonium][tetrakis(perfluorohexylperfluorophenyl)borate]; [(biphenyl)(methyl)(hexafluorononyl)ammonium][tetraperfluorophenylaluminate]; [(3-methyl-perfluorophenyl)(nonyl)(propyl)ammonium][tetrakis(hexafluoroindenyl)aluminate]; [(biphenyl)(perfluoroethyl)(propyl)ammonium][tetrakis(hexafluorononyl)aluminate]; [(octafluorobiphenyl)(diethyl)ammonium][tetraperfluorofluorenylborate]; [(2,3-difluorophenyl)(ethyl)(hexafluorononyl)phosphonium][tetrakis(perfluoronaphthyl)borate]; [(phenyl)(hexyl)(perfluoroethyl)ammonium][tetrakis(octafluorobiphenyl)aluminate]; [(perfluorophenyl)(hexyl)(2-methylpentyl)ammonium][tetrakis(hexafluoroindenyl)borate]; [(2-perfluoromethyl-6-perfluoroethyl-perfluorobiphenyl)(ethyl)(hexafluorononyl)phosphonium][tetraheptylborate]; [(2,5-difluorophenyl)(3-ethylheptyl)(propyl)phosphonium][tetrapentylborate]; [(2,5-difluorophenyl)(propyl)(2-methyl-5-propyl-heptyl)ammonium][tetrabutylaluminate]; [N-(2,5-difluorophenyl)pyrrolium][tetrakis(methyloctafluorbiphenyl)borate]; [(3-methyl-perfluorophenyl)(perfluoroethyl)(2-methyl-5-propyl-heptyl)phosphonium][tetraperfluorophenanthrylborate]; [(2-perfluoromethyl-6-perfluoroethylperfluorobiphenyl)(butyl)(2-methylpentyl)ammonium][tetrakis(ethylhexafluoronaphthyl)borate]; [N-(3-perfluoromethyl-trifluorophenyl)isoindolinium][tetrakis(perfluoromethylperfluoronaphthyl)borate]; [(1-fluorobiphenyl)(butyl)(ethyl)phosphonium][tetraheptylborate]; [N-(2,4-difluorophenyl)phosphindolium][tetraoctylborate]; [(2,4-difluorophenyl)(2-methylpentyl)(hexafluorononyl)ammonium][tetrakis(hexafluorononyl)borate]; [(perfluorophenyl)(hexyl)(nonyl)ammonium][tetraperfluoroanthracenylaluminate]; [(perfluorobiphenyl)(nonyl)(hexyl)ammonium][tetraperfluoroindenylborate]; [(biphenyl)(propyl)(fluoromethyl)phosphonium][tetraperfluorophenanthrylborate]; [N-(2,3-difluorophenyl)phosphindolium][tetraperfluorofluorenylaluminate]; [(2-methyl-6-perfluoromethyl-perfluorobiphenyl)(fluoromethyl)(ethyl)phosphonium][tetranonylborate]; [(1-fluorobiphenyl)(hexafluorononyl)(2-methyl-5-propyl-heptyl)ammonium][tetrakis(hexafluoroindenyl)borate]; [(2,3-difluorophenyl)(perfluoroethyl)(fluoromethyl)phosphonium][tetraperfluorophenanthrylborate]; [(2,5-difluorophenyl)(3-ethylheptyl)(propyl)phosphonium][tetrakis(2-methyl-5-propyl-heptyl)borate]; [(1- fluorobiphenyl)(hexyl)(2-methylpentyl)ammonium][tetrakis(hexafluorononyl)aluminate]; [(perfluorobiphenyl)(2-methyl-5-propyl-heptyl)(methyl)ammonium][tetrakis(perfluoronaphthyl)borate]; [(2-perfluoromethyl-6-perfluoroethyl-perfluorobiphenyl)(propyl)(methyl)ammonium][tetraperfluorophenanthrylaluminate]; [(2-methyl-6-perfluoromethyl-perfluorobiphenyl)(hexyl)(3-ethylheptyl)ammonium][tetrakis(ethylhexafluoronaphthyl)borate]; [(perfluorophenyl)(hexafluorononyl)(butyl)ammonium][tetrakis(heptafluorofluorenyl)aluminate]; [(tetrafluorophenyl)(hexafluorononyl)(2-methylpentyl)phosphonium][tetrakis(heptafluorofluorenyl)aluminate]; [(octafluorobiphenyl)(dihexyl)ammonium][tetrakis(perfluoronaphthyl)aluminate]; [(2,4-difluorophenyl)(ethyl)(2-methyl-5-propyl-heptyl)phosphonium][tetrakis(3-ethylheptyl)aluminate]; [(3-perfluoromethyltrifluorophenyl)(nonyl)(ethyl)ammonium][tetraperfluorofluorenylborate]; [(3-perfluoroethyl-trifluorophenyl)(2-methyl-5-propyl-heptyl)(perfluoroethyl)phosphonium][tetraperfluorophenylborate]; [(2-methyl-6-perfluoromethylperfluorobiphenyl)(3-ethylheptyl)(ethyl)phosphonium][tetrakis(heptafluorofluorenyl)aluminate]; [(2-methyl-6-perfluoromethyl-perfluorobiphenyl)(butyl)(hexyl)phosphonium][tetrakis(2-methyl-5-propyl-heptyl)aluminate]; [(perfluorobiphenyl)(2-methyl-5-propyl-heptyl)(3-ethylheptyl)ammonium][tetraoctylaluminate]; [(2,5-difluorophenyl)(propyl)(perfluoroethyl)ammonium][tetrakis(hexafluorononyl)borate]; [(2,4-difluorophenyl)(fluoromethyl)(ethyl)ammonium][tetrakis(methylperfluoronaphthyl)aluminate]; [(perfluorophenyl)(fluoromethyl)(nonyl)ammonium][tetrakis(2-methylpentyl)aluminate]; [(perfluorophenyl)(methyl)(propyl)phosphonium][tetrakis(octafluorobiphenyl)aluminate]; [N-(biphenyl)phosphindolium][tetrabutylborate]; [(octafluorobiphenyl)(methyl)(ethyl)ammonium][tetrakis(pentafluoronaphthyl)borate]; [(3-perfluoroethyl-trifluorophenyl)(3-ethyiheptyl)(perfluoroethyl)ammonium][tetraheptylaluminate]; [(2,5-difluorophenyl)(methyl)(3-ethylheptyl)phosphonium][tetranonylborate]; [(2-methyl-6-perfluoromethylperfluorobiphenyl)(propyl)(2-methyl-5-propyl-heptyl)ammonium][tetrakis(perfluoropentylperfluorobiphenyl)borate]; [(1-fluorobiphenyl)(ethyl)(3-ethylheptyl)ammonium][tetrakis(perfluoroethylperfluorobiphenyl)borate]; [(1-fluorophenyl)(dinonyl)phosphonium][tetrabutylaluminate]; [(3-methyl-perfluorophenyl)(2-methylpentyl)(methyl)ammonium][tetrakis(perfluorohexylperfluorophenyl)borate]; [(perfluorobiphenyl)(2-methylpentyl)(3-ethylheptyl)ammonium][tetrakis(perfluoronaphthyl)aluminate]; [(2,5-difluorophenyl)(3-ethylheptyl)(hexyl)ammonium][tetrakis(perfluorobiphenyl)aluminate]; [(2-methyl-6-perfluoromethyl-perfluorobiphenyl)(ethyl)(nonyl)phosphonium][tetrakis(perfluoroethylperfluorobiphenyl)aluminate]; [N-(1-fluorophenyl)indolium][tetrakis(methyloctafluorbiphenyl)borate]; [(2,5-difluorophenyl)(hexyl)(methyl)ammonium][tetraperfluoroindenylaluminate]; [(1-fluorobiphenyl)(2-methylpentyl)(nonyl)phosphonium][tetrapentylborate]; [(2,3-difluorophenyl)(hexyl)(fluoromethyl)ammonium][tetrakis(hexafluorononyl)aluminate]; [(tetrafluorophenyl)(hexyl)(methyl)ammonium][tetrakis(2-methylpentyl)aluminate]; [(3-perfluoromethyl-trifluorophenyl)(butyl)(hexyl)ammonium][tetraperfluorofluorenylborate]; [(1-fluorobiphenyl)(nonyl)(propyl)ammonium][tetrakis(hexafluoronapthyl)borate]; [(2-perfluoromethyl-6-perfluoroethyl-perfluorobiphenyl)(2-methyl-5-propyl-heptyl)(methyl)phosphonium][tetrakis(perfluoroethylperfluorobiphenyl)aluminate]; [(hexafluorobiphenyl)(ethyl)(hexyl)ammonium][tetraperfluorophenanthrylaluminate]; [(3-perfluoroethyl-trifluorophenyl)(ethyl)(3-ethylheptyl)ammonium][tetraperfluorophenylborate]; [(3-perfluoromethyl-trifluorophenyl)(2-methylpentyl)(perfluoroethyl)ammonium][tetrakis(hexafluoronapthyl)borate]; [N-(perfluorophenyl)isoindolinium][tetraperfluorophenylborate]; [(1-fluorobiphenyl)(ethyl)(2-methylpentyl)ammonium][tetrakis(pentafluoroindenyl)borate]; [(2,3-difluorophenyl)(nonyl)(butyl)ammonium][tetraheptylaluminate]; [(2,5-difluorophenyl)(butyl)(hexyl)ammonium][tetraheptylborate]; [(1-fluorophenyl)(methyl)(hexafluorononyl)phosphonium][tetrakis(hexafluoroindenyl)borate]; [(3-perfluoromethyl-trifluorophenyl)(hexafluorononyl)(nonyl)ammonium][tetrakis(perfluoronaphthyl)borate]; [(hexafluorobiphenyl)(propyl)(nonyl)phosphonium][tetrakis(perfluoromethylperfluoronaphthyl)aluminate]; [(2,3-difluorophenyl)(propyl)(hexyl)phosphonium][tetrabutylborate]; [(2,4-difluorophenyl)(3-ethylheptyl)(nonyl)ammonium][tetrakis(2-methyl-5-propyl-heptyl)aluminate]; [(2,4-difluorophenyl)(fluoromethyl)(hexyl)ammonium][tetrakis(methyloctafluorbiphenyl)borate]; [(octafluorobiphenyl)(ethyl)(propyl)ammonium][tetrakis(perfluorobiphenyl)borate]; [(2,3-difluorophenyl)(2-methyl-5-propyl-heptyl)(butyl)ammonium][tetraperfluorophenylborate]; [(hexafluorobiphenyl)(dipropyl)phosphonium][tetraperfluorophenylborate]; [(2,4-difluorophenyl)(nonyl)(ethyl)phosphonium][tetrakis(methylperfluoronaphthyl)aluminate]; [(2,3-difluorophenyl)(propyl)(perfluoroethyl)phosphonium][tetranonylborate]; [(perfluorobiphenyl)(2-methyl-5-propyl-heptyl)(methyl)ammonium][tetrakis(perfluorohexylperfluorophenyl)aluminate]; [(2-perfluoromethyl-6-perfluoroethyl-perfluorobiphenyl)(nonyl)(propyl)ammonium][tetrakis(pentafluoroindenyl)aluminate]; [(tetrafluorophenyl)(3-ethylheptyl)(2-methylpentyl)ammonium][tetrakis(methylperfluoronaphthyl)borate]; [(2-methyl-6-perfluoromethylperfluorobiphenyl)(methyl)(3-ethylheptyl)phosphonium][tetrakis(pentafluoronaphthyl)borate]; [(perfluorophenyl)(dibutyl)ammonium][tetrakis(perfluoroethylperfluorobiphenyl)aluminate]; [(1-fluorophenyl)(fluoromethyl)(hexyl)ammonium][tetrakis(pentafluoronaphthyl)aluminate]; [(3-perfluoroethyl-trifluorophenyl)(2-methyl-5-propyl-heptyl)(hexyl)phosphonium][tetraperfluorophenylborate]; [(2,4-difluorophenyl)(ethyl)(methyl)ammonium][tetrakis(3-ethylheptyl)borate]; [(octafluorobiphenyl)(hexafluorononyl)(2-methylpentyl)ammonium][tetraheptylborate]; [(2,3-difluorophenyl)(dihexyl)phosphonium][tetrakis(2-methylpentyl)aluminate]; [(biphenyl)(3-ethylheptyl)(2-methylpentyl)phosphonium][tetrakis(methylperfluoronaphthyl)aluminate]; [(tetrafluorophenyl)(ethyl)(2-methyl-5-propyl-heptyl)ammonium][tetraoctylborate]; [(octafluorobiphenyl)(2-methylpentyl)(nonyl)ammonium][tetrakis(perfluorohexylperfluorophenyl)aluminate]; [(octafluorobiphenyl)(hexafluorononyl)(methyl)ammonium][tetraperfluorofluorenylaluminate]; [(2-methyl-6-perfluoromethyl-perfluorobiphenyl)(nonyl)(hexafluorononyl)ammonium][tetrabutylaluminate]; [(2,4-difluorophenyl)(propyl)(fluoromethyl)ammonium][tetrakis(perfluoronaphthyl)borate]; [N-(1-fluorobiphenyl)phosphindolinium][tetrakis(hexafluoroindenyl)borate]; [(2,3-difluorophenyl)(nonyl)(methyl)ammonium][tetrakis(heptafluorofluorenyl)borate]; [(2-methyl-6- perfluoromethyl-perfluorobiphenyl)(hexafluorononyl)
(ethyl)ammonium][tetraoctylborate]; [(3-perfluoromethyl-
trifluorophenyl)(3-ethylheptyl)(methyl)ammonium][tetrakis
(perfluoropyrenyl)borate]; [(perfluorophenyl)(3-
ethylheptyl)(propyl)phosphonium][tetrakis
(ethylhexafluoronaphthyl)borate]; [(hexafluorobiphenyl)
(hexafluorononyl)(butyl)ammonium][tetraoctylborate]; [(2,
3-difluorophenyl)(methyl)(nonyl)phosphonium][tetrakis
(pentafluoroindenyl)aluminate]; [(3-perfluoromethyl-
trifluorophenyl)(ethyl)(nonyl)phosphonium][tetrakis
(perfluorobiphenyl)aluminate]; [(1-fluorophenyl)(butyl)
(hexyl)ammonium][tetrakis(ethyihexafluoronaphthyl)
aluminate]; [(perfluorophenyl)(methyl)(3-ethylheptyl)
ammonium][tetraperfluorophenanthrylborate]; [(3-
perfluoroethyl-trifluorophenyl)(butyl)(2-methylpentyl)
phosphonium][tetrakis(octafluorobiphenyl)borate]; [(2-
perfluoromethyl-6-perfluoroethyl-perfluorobiphenyl)(3-
ethylheptyl)(2-methylpentyl)phosphonium][tetrakis
(pentafluoronaphthyl)borate]- [(2,3-difluorophenyl)(hexyl)
(2-methyl-5-propyl-heptyl)ammonium][tetrakis
(perfluoromethylperfluoronaphthyl)aluminate]; [(2,4-
difluorophenyl)(2-methylpentyl)(methyl)phosphonium]
[tetrakis(pentafluoronaphthyl)borate]; [(2,4-difluorophenyl)
(methyl)(propyl)ammonium][tetrakis(heptafluorofluorenyl)
borate]; [(perfluorophenyl)(propyl)(methyl)ammonium]
[tetrakis(3-ethylheptyl)borate]; [(hexafluorobiphenyl)
(ethyl)(nonyl)ammonium][tetrahextylborate]; [(3-
perfluoromethyl-trifluorophenyl)(ethyl)(2-methyl-5-propyl-
heptyl)ammonium][tetrahextylborate]; [(perfluorophenyl)
(ethyl)(2-methylpentyl)ammonium][tetrakis
(perfluoropyrenyl)aluminate]; [N-(octafluorobiphenyl)
phosphapyrrolidinium][tetranonylaluminate]; [(2,3-
difluorophenyl)(2-methyl-5-propyl-heptyl)(ethyl)
phosphonium][tetrabutylaluminate]; [N-(2,3-
difluorophenyl)pyrrolidinium][tetrakis
(methyloctafluorbiphenyl)borate]; [(3-perfluoromethyl-
trifluorophenyl)(3-ethylheptyl)(2-methylpentyl)
phosphonium][tetrakis(ethylhexafluoronaphthyl)
aluminate]; [N-(tetrafluorophenyl)pyrrolonium]
[tetraperfluorophenylborate]; [(2-perfluoromethyl-6-
perfluoroethyl-perfluorobiphenyl)(methyl)
(hexafluorononyl)ammonium][tetrakis(3-ethylheptyl)
aluminate]; [N-(3-perfluoroethyl-trifluorophenyl)indolium]
[tetraperfluorophenylborate]; [N-(2-perfluoromethyl-6-
perfluoroethyl-perfluorobiphenyl)phosphapyrrolidinium]
[tetrapentylborate]; [(1-fluorophenyl)(hexyl)(2-
methylpentyl)phosphonium][tetrakis(perfluorobiphenyl)
aluminate]; [(3-methylperfluorophenyl)(ethyl)(propyl)
ammonium][tetraoctylborate]; [(3-
perfluoroethyltrifluorophenyl)(hexyl)(3-ethylheptyl)
ammonium][tetrakis(perfluoronaphthyl)aluminate]; [(2,3-
difluorophenyl)(2-methylpentyl)(3-ethylheptyl)ammonium]
[tetrabutylborate]; [(perfluorophenyl)(perfluoroethyl)
(fluoromethyl)ammonium][tetrakis(pentafluoronaphthyl)
aluminate]; [(2-methyl-6-perfluoromethyl-
perfluorobiphenyl)(methyl)(fluoromethyl)phosphonium]
[tetraperfluorophenylborate]; [(3-perfluoroethyl-
trifluorophenyl)(hexyl)(3-ethylheptyl)ammonium][tetrakis
(3-ethylheptyl)aluminate]; [(2-perfluoromethyl-6-
perfluoroethyl-perfluorobiphenyl)(methyl)(2-methylpentyl)
phosphonium][tetrabutylaluminate]; [(2-perfluoromethyl-6-
perfluoroethyl-perfluorobiphenyl)(propyl)(2-methyl-5-
propyl-heptyl)ammonium][tetrakis(perfluoromethyl-
perfluoronaphthyl)aluminate]; [(2,5-difluorophenyl)
(fluoromethyl)(hexafluorononyl)ammonium][tetrakis(2-
methylpentyl)aluminate]; [(2-perfluoromethyl-6-
perfluoroethyl-perfluorobiphenyl)(perfluoroethyl)(ethyl)
ammonium][tetranonylaluminate]; [(2-perfluoromethyl-6-
perfluoroethyl-perfluorobiphenyl)(ethyl)(butyl)
phosphonium][tetranonylaluminate]; [(1-fluorobiphenyl)
(propyl)(2-methylpentyl)phosphonium][tetrakis
(perfluoroethyl-perfluorobiphenyl)aluminate]; [(biphenyl)
(fluoromethyl)(propyl)phosphonium][tetrakis
(perfluorobiphenyl)aluminate]; [N-(perfluorophenyl)
isoindolinium][tetrakis(perfluoropyrenyl)aluminate]; [(3-
methyl-perfluorophenyl)(hexafluorononyl)(3-ethylheptyl)
ammonium][tetraperfluoroindenylaluminate]; [N-(phenyl)
phosphapyrrolidinium][tetraperfluoroanthracenylborate];
[(3-perfluoroethyl-trifluorophenyl)(fluoromethyl)(2-
methyl-5-propyl-heptyl)ammonium]
[tetraperfluorophenylborate]; [(2,3-difluorophenyl)(nonyl)
(hexafluorononyl)ammonium][tetrakis(perfluoropyrenyl)
borate]; [(3-perfluoromethyl-trifluorophenyl)(butyl)
(propyl)ammonium][tetrakis(2-methyl-5-propyl-heptyl)
borate]; [(1-fluorophenyl)(ethyl)(butyl)ammonium]
[tetraperfluorophenanthrylaluminate]; [(2,3-difluorophenyl)
(butyl)(2-methylpentyl)phosphonium][tetrakis
(perfluoropentylperfluorobl)phenyl)aluminate]; [(2,3-
difluorophenyl)(dipropyl)ammonium][tetrakis
(perfluorohexylperfluorophenyl)aluminate]; [(2-methyl-6-
perfluoromethyl-perfluorobiphenyl)(hexafluorononyl)
(butyl)ammonium][tetrahextylborate]; [(3-methyl-
perfluorophenyl)(3-ethylheptyl)(ethyl)ammonium][tetrakis
(pentafluoronaphthyl)borate]; [(3-perfluoroethyl-
trifluorophenyl)(perfluoroethyl)(hexyl)ammonium][tetrakis
(hexafluoronapthyl)borate]; [(perfluorobiphenyl)(2-methyl-
5-propyl-heptyl)(3-ethylheptyl)ammonium]
[tetrahextylborate]; [(3-methyl-perfluorophenyl)
(perfluoroethyl)(2-methylpentyl)phosphonium]
[tetrapentylborate]; [(3-methyl-perfluorophenyl)(propyl)
(fluoromethyl)ammonium][tetrakis
(ethylhexafluoronaphthyl)borate]; [(hexafluorobiphenyl)
(hexyl)(propyl)phosphonium][tetrakis
(methylperfluoronaphthyl)aluminate]; [(2-methyl-6-
perfluoromethylperfluorobiphenyl)(2-methyl-5-propyl-
heptyl)(methyl)phosphonium][tetrakis(2-methylpentyl)
aluminate]; [(2,4-difluorophenyl)(methyl)(perfluoroethyl)
phosphonium][tetranonylborate]; [(3-perfluoromethyl-
trifluorophenyl)(dihexafluorononyl)phosphonium][tetrakis
(methyloctafluorbiphenyl)aluminate]; [(1-fluorophenyl)(2-
methylpentyl)(hexafluorononyl)ammonium]
[tetrahextylaluminate]; [(perfluorophenyl)(perfluoroethyl)
(methyl)ammonium][tetraheptylborate]; [(1-fluorophenyl)
(nonyl)(butyl)ammonium][tetrakis(pentafluoronaphthyl)
borate]; [(biphenyl)(ethyl)(3-ethylheptyl)ammonium]
[tetrahextylaluminate]; [N-(tetrafluorophenyl)
phosphapyrrolidinium][tetrakis(methyloctafluorbiphenyl)
borate]; [(phenyl)(hexyl)(fluoromethyl)ammonium]
[tetraperfluoroindenylaluminate]; [(tetrafluorophenyl)
(perfluoroethyl)(ethyl)ammonium][tetraheptylaluminate];
[(perfluorophenyl)(dimethyl)ammonium][tetrakis
(perfluoropyrenyl)aluminate]; [(3-perfluoroethyl-
trifluorophenyl)(hexyl)(ethyl)phosphonium][tetrakis
(hexafluorononyl)borate]; [(perfluorophenyl)
(hexafluorononyl)(propyl)phosphonium][tetrakis
(hexafluoronapthyl)borate]; [(1-fluorobiphenyl)
(diperfluoroethyl)ammonium][tetrakis
(heptafluorofluorenyl)aluminate]; [(2-perfluoromethyl-6-
perfluoroethyl-perfluorobiphenyl)(propyl)(hexyl)
ammonium][tetrakis(perfluoropyrenyl)borate];
[(hexafluorobiphenyl)(3-ethylheptyl)(propyl)ammonium]
[tetraoctylalumnate]; [N-(1-fluorophenyl)pyrrolium]
[tetrakis(hexafluoroindenyl)aluminate]; [(2,3-
difluorophenyl)(di2-methylpentyl)phosphonium][tetrakis (2-methyl-5-propyl-heptyl)aluminate]; [(perfluorobiphenyl)(2-methylpentyl)(hexyl)ammonium][tetraperfluoroindenylaluminate]; [(2-perfluoromethyl-6-perfluoroethyl-perfluorobiphenyl)(propyl)(fluoromethyl)ammonium][tetraperfluoroanthracenylaluminate]; [(hexafluorobiphenyl)(dipropyl)phosphonium][tetrakis(ethylhexafluoronaphthyl)borate]; [(3-perfluoromethyl-trifluorophenyl)(2-methyl-5-propyl-heptyl)(2-methylpentyl)ammonium][tetrakis(ethylhexafluoronaphthyl)borate]; [(biphenyl)(2-methyl-5-propyl-heptyl)(hexyl)ammonium][tetrakis(3-ethylheptyl)aluminate]; [(biphenyl)(fluoromethyl)(hexyl)ammonium][tetrakis(hexafluorononyl)aluminate]; [(biphenyl)(propyl)(nonyl)ammonium][tetraperfluorophenylborate]; [N-(tetrafluorophenyl)indolium][tetranonylaluminate]; [(2,4-difluorophenyl)(dimethyl)ammonium][tetranonylaluminate]; [(tetrafluorophenyl)(nonyl)(hexyl)ammonium][tetrakis(perfluoropyrenyl)aluminate]; [(3-methyl-perfluorophenyl)(perfluoroethyl)(fluoromethyl)ammonium][tetraperfluorophenylaluminate]; [(tetrafluorophenyl)(ethyl)(methyl)phosphonium][tetranonylaluminate]; [(octafluorobiphenyl)(3-ethylheptyl)(propyl)ammonium][tetraperfluorophenanthrylborate]; [(hexafluorobiphenyl)(dinonyl)ammonium][tetrakis(perfluoropyrenyl)borate]; [(perfluorophenyl)(propyl)(ethyl)ammonium][tetrakis(perfluorohexylperfluorophenyl)borate]; [(2-perfluoromethyl-6-perfluoroethyl-perfluorobiphenyl)(methyl)(propyl)phosphonium][tetrabutylaluminate]; [(3-perfluoroethyl-trifluorophenyl)(3-ethylheptyl)(propyl)ammonium][tetrakis(perfluoropyrenyl)borate]; [(tetrafluorophenyl)(butyl)(methyl)phosphonium][tetrakis(perfluoropyrenyl)borate]; [(3-perfluoroethyl-trifluorophenyl)(dipropyl)ammonium][tetrakis(ethylhexafluoronaphthyl)borate]; [(3-perfluoroethyl-trifluorophenyl)(perfluoroethyl)(butyl)ammonium][tetranonylaluminate]; [(octafluorobiphenyl)(fluoromethyl)(propyl)phosphonium][tetrakis(octafluorobiphenyl)borate]; [(3-perfluoromethyl-trifluorophenyl)(2-methylpentyl)(3-ethylheptyl)ammonium][tetraoctylborate]; [(2-perfluoromethyl-6-perfluoroethyl-perfluorobiphenyl)(ethyl)(2-methylpentyl)ammonium][tetrakis(2-methyl-5-propyl-heptyl)aluminate]; [(biphenyl)(propyl)(2-methyl-5-propyl-heptyl)ammonium][tetrakis(hexafluoroindenyl)aluminate]; [(1-fluorobiphenyl)(nonyl)(2-methyl-5-propyl-heptyl)phosphonium][tetraperfluorophenanthrylborate]; [N-(hexafluorobiphenyl)piperidinium][tetrakis(pentafluoroindenyl)borate]; [(biphenyl)(ethyl)(hexafluorononyl)phosphonium][tetrakis(perfluoroethylperfluorobiphenyl)aluminate]; [(3-perfluoroethyl-trifluorophenyl)(3-ethylheptyl)(2-methyl-5-propyl-heptyl)ammonium][tetrakis(perfluoroethyl-perfluorobiphenyl)aluminate]; [(3-perfluoroethyl-trifluorophenyl)(ethyl)(2m-ethylpentyl)ammonium][tetranonylborate]; [(octafluorobiphenyl)(nonyl)(2-methylpentyl)ammonium][tetrakis(3-ethylheptyl)aluminate]; [N-(3-perfluoroethyl-trifluorophenyl)indolinium][tetrakis(perfluoropyrenyl)aluminate]; [(tetrafluorophenyl)(hexafluorononyl)(butyl)phosphonium][tetrakis(heptafluorofluorenyl)borate]; [(perfluorophenyl)(nonyl)(propyl)ammonium][tetraoctylborate]; [(octafluorobiphenyl)(butyl)(nonyl)ammonium][tetraoctylaluminate]; [(2-perfluoromethyl-6-perfluoroethyl-perfluorobiphenyl)(perfluoroethyl)(hexafluorononyl)phosphonium][tetrakis(perfluoronaphthyl)aluminate]; [(2-methyl-6-perfluoromethyl-perfluorobiphenyl)(butyl)(hexyl)phosphonium][tetrakis(perfluoropyrenyl)aluminate]; [(tetrafluorophenyl)(2-methylpentyl)(hexyl)ammonium][tetrakis(hexafluorononyl)aluminate]; [(octafluorobiphenyl)(2-methylpentyl)(perfluoroethyl)ammonium][tetrakis(perfluoropyrenyl)borate]; [(hexafluorobiphenyl)(ethyl)(2-methyl-5-propyl-heptyl)ammonium][tetrakis(pentafluoronaphthyl)borate]; [(tetrafluorophenyl)(dihexyl)ammonium][tetrakis(perfluoropyrenyl)borate]; [(3-methyl-perfluorophenyl)(hexafluorononyl)(2-methyl-5-propyl-heptyl)phosphonium][tetraperfluorophenanthrylborate]; [(2-perfluoromethyl-6-perfluoroethyl-perfluorobiphenyl)(hexafluorononyl)(perfluoroethyl)phosphonium][tetrakis(hexafluoroindenyl)borate]; [(perfluorobiphenyl)(nonyl)(perfluoroethyl)ammonium][tetrakis(pentafluoroindenyl)aluminate]; [(octafluorobiphenyl)(butyl)(hexafluorononyl)ammonium][tetrakis(pentafluoronaphthyl)borate]; [(perfluorobiphenyl)(methyl)(butyl)ammonium][tetrakis(heptafluorofluorenyl)borate]; [(perfluorobiphenyl)(hexafluorononyl)(methyl)phosphonium][tetrakis(heptafluorofluorenyl)borate]; [(2-perfluoromethyl-6-perfluoroethylperfluorobiphenyl)(ethyl)(butyl)phosphonium][tetrakis(perfluoroethylperfluorobiphenyl)borate]; [(2,3-difluorophenyl)(hexyl)(fluoromethyl)ammonium][tetrakis(perfluorohexylperfluorophenyl)aluminate]; [(2-perfluoromethyl-6-perfluoroethyl-perfluorobiphenyl)(ethyl)(methyl)ammonium][tetrakis(hexafluorononyl)borate]; [(perfluorophenyl)(nonyl)(perfluoroethyl)phosphonium][tetrakis(hexafluorononyl)borate]; [(octafluorobiphenyl)(perfluoroethyl)(propyl)phosphonium][tetrakis(methyloctafluorbiphenyl)aluminate]; [(tetrafluorophenyl)(3-ethylheptyl)(butyl)ammonium][tetrakis(hexafluoronapthyl)borate]; [(3-methylperfluorophenyl)(fluoromethyl)(ethyl)ammonium][tetrakis(perfluoroaphthyl)aluminate]; [(octafluorobiphenyl)(diperfluoroethyl)ammonium][tetrabutylaluminate]; [(tetrafluorophenyl)(fluoromethyl)(nonyl)ammonium][tetraperfluoroanthracenylaluminate]; [(biphenyl)(propyl)(butyl)ammonium][tetrakis(perfluorobiphenyl)borate]; [(octafluorobiphenyl)(dipropyl)phosphonium][tetrakis(octafluorobiphenyl)borate]; [(2-perfluoromethyl-6-perfluoroethylperfluorobiphenyl)(2-methyl-5-propyl-heptyl)(perfluoroethyl)ammonium][tetraperfluorophenanthrylborate]; [(2,3-difluorophenyl)(hexyl)(perfluoroethyl)phosphonium][tetrakis(3-ethylheptyl)borate]; [(phenyl)(3-ethylheptyl)(nonyl)ammonium][tetrakis(pentafluoroindenyl)borate]; [(3-methylperfluorophenyl)(propyl)(hexyl)ammonium][tetrakis(perfluoronaphthyl)aluminate]; [(1-fluorobiphenyl)(dibutyl)phosphonium][tetraperfluorofluorenylborate]; [(3-methyl-perfluorophenyl)(nonyl)(fluoromethyl)ammonium][tetrabutylborate]; [(perfluorobiphenyl)(2-methylpentyl)(ethyl)ammonium][tetraperfluorophenylaluminate]; [(3-perfluoroethyl-trifluorophenyl)(butyl)(2-methylpentyl)phosphonium][tetrakis(pentafluoroindenyl)aluminate]; [(biphenyl)(methyl)(ethyl)ammonium][tetrakis(pentafluoronaphthyl)aluminate]; [N-(hexafluorobiphenyl)piperidinium][tetrakis(hexafluorononyl)borate]; [(2,3-difluorophenyl)(ethyl)(hexyl)phosphonium][tetrakis(perfluoropentylperfluorobiphenyl)aluminate]; [(1-fluorobiphenyl)(2-methyl-5-propyl-heptyl)(ethyl)ammonium][tetrakis(hexafluorononyl)borate]; [(3-perfluoroethyltrifluorophenyl)(perfluoroethyl)(fluoromethyl)ammonium][tetrakis(octafluorobiphenyl)borate]; [(1-fluorophenyl)(ethyl)(fluoromethyl)phosphonium][tetrakis(hexafluorononyl)aluminate]; [(perfluorobiphenyl)(methyl)(butyl)ammonium][tetraperfluorofluorenylborate]; [(perfluorophenyl)(hexafluorononyl)(butyl)ammonium]

[tetraperfluorophenanthrylborate]; [(1-fluorobiphenyl)(propyl)(nonyl)phosphonium][tetrakis(hexafluorononyl)borate]; [(2-perfluoromethyl-6-perfluoroethyl-perfluorobiphenyl)(hexafluorononyl)(2-methylpentyl)ammonium][tetrakis(perfluoroethylperfluorobiphenyl)borate]; [N-(hexafluorobiphenyl)phosphapyrrolidinium][tetrakis(perfluoroethylperfluorobiphenyl)aluminate]; [(phenyl)(perfluoroethyl)(methyl)ammonium][tetrakis(3-ethylheptyl)borate]; [(2-perfluoromethyl-6-perfluoroethyl-perfluorobiphenyl)(diethyl)ammonium][tetrakis(perfluorobiphenyl)aluminate]; [(1-fluorobiphenyl)(methyl)(fluoromethyl)ammonium][tetrabutylaluminate]; [(octafluorobiphenyl)(ethyl)(propyl)phosphonium][tetranonylborate]; [(perfluorophenyl)(ethyl)(methyl)phosphonium][tetrakis(perfluoronaphthyl)borate]; [(biphenyl)(hexafluorononyl)(hexyl)phosphonium][tetrakis(hexafluoroindenyl)borate]; [(biphenyl)(methyl)(hexyl)phosphonium][tetrakis(perfluoropentylperfluorobiphenyl)borate]; [(2-methyl-6-perfluoromethyl-perfluorobiphenyl)(perfluoroethyl)(3-ethylheptyl)ammonium][tetrakis(hexafluoroindenyl)aluminate]; [(phenyl)(perfluoroethyl)(hexafluorononyl)phosphonium][tetrakis(perfluorobiphenyl)borate]; [(tetrafluorophenyl)(2-methylpentyl)(2-methyl-5-propyl-heptyl)phosphonium][tetrakis(perfluoronaphthyl)borate]; [(1-fluorobiphenyl)(hexyl)(ethyl)ammonium][tetraperfluorofluorenylaluminate]; [(octafluorobiphenyl)(hexafluorononyl)(hexyl)ammonium][tetrakis(3-ethylheptyl)borate]; [(3-perfluoroethyl-trifluorophenyl)(hexafluorononyl)(ethyl)ammonium][tetrakis(heptafluorofluorenyl)borate]; [(3-perfluoroethyl-trifluorophenyl)(3-ethylheptyl)(methyl)ammonium][tetrakis(2-methylpentyl)aluminate]; [(3-methyl-perfluorophenyl)(3-ethylheptyl)(ethyl)ammonium][tetrakis(perfluoronaphthyl)borate]; [(biphenyl)(2-methylpentyl)(hexyl)ammonium][tetrapentylborate]; [(octafluorobiphenyl)(3-ethylheptyl)(fluoromethyl)ammonium][tetrakis(perfluorohexylperfluorophenyl)aluminate]; [(octafluorobiphenyl)(2-methylpentyl)(fluoromethyl)ammonium][tetrakis(methyloctafluorbiphenyl)borate]; [(phenyl)(ethyl)(2-methylpentyl)ammonium][tetraheptylborate]; [(biphenyl)(3-ethylheptyl)(fluoromethyl)ammonium][tetrakis(methylperfluoronaphthyl)borate]; [(2,3-difluorophenyl)(3-ethylheptyl)(hexyl)phosphonium][tetrakis(penfluoroethylperfluorobiphenyl)aluminate]; [(3-perfluoromethyl-trifluorophenyl)(2-methylpentyl)(nonyl)ammonium][tetrakis(3-ethylheptyl)borate]; [N-(tetrafluorophenyl)indolinium][tetrakis(3-ethylheptyl)aluminate]; [(3-methyl-perfluorophenyl)(butyl)(ethyl)phosphonium][tetrakis(octafluorobiphenyl)borate]; [(biphenyl)(3-ethylheptyl)(butyl)ammonium][tetrabutylborate]; [N-(2,4-difluorophenyl)indolium][tetraperfluorophenylaluminate]; [(biphenyl)(2-methyl-5-propyl-heptyl)(butyl)ammonium][tetrakis(hexafluoronapthyl)aluminate]; [(biphenyl)(nonyl)(perfluoroethyl)ammonium][tetrakis(pentafluoroindenyl)borate]; [(2-methyl-6-perfluoromethyl-perfluorobiphenyl)(3-ethylheptyl)(nonyl)ammonium][tetrapentylaluminate]; [(3-perfluoromethyltrifluorophenyl)(3-ethylheptyl)(2-methyl-5-propyl-heptyl)ammonium][tetrakis(heptafluorofluorenyl)aluminate]; [N-(2,5-difluorophenyl)phosphapyrrolidinium][tetrakis(perfluoroethylperfluorobiphenyl)borate]; [(hexafluorobiphenyl)(2-methyl-5-propyl-heptyl)(ethyl)ammonium][tetraperfluorophenanthrylborate]; [(3-perfluoroethyl-trifluorophenyl)(methyl)(2-methylpentyl)ammonium][tetrakis(perfluoronaphthyl)aluminate]; [(tetrafluorophenyl)(butyl)(2-methyl-5-propyl-heptyl)ammonium][tetrakis(perfluoromethylperfluoronaphthyl)aluminate]; [(3-perfluoromethyl-trifluorophenyl)(diperfluoroethyl)ammonium][tetrakis(octafluorobiphenyl)aluminate]; [(phenyl)(hexyl)(fluoromethyl)ammonium][tetrakis(hexafluoronapthyl)aluminate]; [(3-perfluoroethyl-trifluorophenyl)(nonyl)(ethyl)ammonium][tetrakis(methylperfluoronaphthyl)borate]; [(perfluorobiphenyl)(propyl)(hexafluorononyl)ammonium][tetrakis(perfluoropyrenyl)borate]; [(3-perfluoroethyl-trifluorophenyl)(perfluoroethyl)(methyl)ammonium][tetrakis(perfluoropyrenyl)borate]; [(octafluorobiphenyl)(2-methylpentyl)(perfluoroethyl)ammonium][tetrakis(pentafluoroindenyl)aluminate]; [(octafluorobiphenyl)(2-methylpentyl)(perfluoroethyl)ammonium][tetrahexylaluminate]; [(biphenyl)(methyl)(hexyl)phosphonium][tetrabutylaluminate]; [(2,4-difluorophenyl)(butyl)(3-ethylheptyl)phosphonium][tetrakis(hexafluoroindenyl)aluminate]; [(2-methyl-6-perfluoromethyl-perfluorobiphenyl)(2-methyl-5-propyl-heptyl)(hexyl)ammonium][tetrakis(3-ethylheptyl)aluminate]; [(1-fluorobiphenyl)(nonyl)(perfluoroethyl)ammonium][tetrakis(hexafluorononyl)borate]; [(1-fluorobiphenyl)(2-methyl-5-propyl-heptyl)(3-ethylheptyl)ammonium][tetrakis(octafluorobiphenyl)borate]; [(phenyl)(perfluoroethyl)(nonyl)phosphonium][tetraperfluoroindenylborate]; [(2,4-difluorophenyl)(diethyl)ammonium][tetraoctylaluminate]; [(2,3-difluorophenyl)(propyl)(ethyl)ammonium][tetrabutylaluminate]; [(2,3-difluorophenyl)(hexafluorononyl)(2-methylpentyl)phosphonium][tetrakis(hexafluoronapthyl)aluminate]; [(phenyl)(3-ethylheptyl)(nonyl)ammonium][tetrakis(hexafluoroindenyl)aluminate]-[(3-perfluoromethyl-trifluorophenyl)(2-methylpentyl)(perfluoroethyl)phosphonium][tetrakis(hexafluorononyl)aluminate]; [(3-methyl-perfluorophenyl)(dibutyl)phosphonium][tetrapentylborate]; [(octafluorobiphenyl)(propyl)(butyl)ammonium][tetrabutylaluminate]; [(tetrafluorophenyl)(methyl)(propyl)ammonium][tetrakis(2-methylpentyl)aluminate]; [(biphenyl)(methyl)(2-methyl-5-propyl-heptyl)phosphonium][tetrakis(perfluorobiphenyl)aluminate]; [(hexafluorobiphenyl)(3-ethylheptyl)(propyl)phosphonium][tetrakis(2-methyl-5-propyl-heptyl)aluminate]; [(3-perfluoroethyl-trifluorophenyl)(dipropyl)ammonium][tetraperfluorophenylaluminate]; [(2,3-difluorophenyl)(hexyl)(fluoromethyl)ammonium][tetraperfluorofluorenylborate]; [N-(3-perfluoromethyltrifluorophenyl)phosphapyrrolidinium][tetrakis(perfluoropyrenyl)borate]; [(1-fluorophenyl)(methyl)(3-ethylheptyl)phosphonium][tetrahextylaluminate]; [(hexafluorobiphenyl)(fluoromethyl)(nonyl)ammonium][tetrakis(3-ethylheptyl)borate]; [(biphenyl)(butyl)(perfluoroethyl)phosphonium][tetrakis(perfluoropyrenyl)borate]; [(biphenyl)(fluoromethyl)(hexyl)phosphonium][tetrakis(octafluorobiphenyl)borate]; [(2-perfluoromethyl-6-perfluoroethyl-perfluorobiphenyl)(2-methyl-5-propyl-heptyl)(propyl)ammonium][tetranonylborate]; [(2,5-difluorophenyl)(perfluoroethyl)(hexyl)ammonium][tetrakis(perfluoronaphthyl)borate]; [N-(3-perfluoromethyl-trifluorophenyl)phosphindolinium][tetraperfluorophenylaluminate]; [(3-methyl-perfluorophenyl)(propyl)(ethyl)phosphonium][tetrakis(pentafluoroindenyl)aluminate]; [(perfluorobiphenyl)(3-ethylheptyl)(2-methyl-5-propyl-heptyl)ammonium][tetraperfluoroanthracenylborate]; [(2-perfluoromethyl-6- perfluoroethyl-perfluorobiphenyl)(hexyl)(ethyl) phosphonium][tetraperfluorofluorenylaluminate]; [(phenyl)(propyl)(2-methylpentyl)phosphonium][tetrakis(perfluoroethylperfluorobiphenyl)borate]; [(3-perfluoroethyl-trifluorophenyl)(methyl)(butyl)phosphonium][tetrakis(hexafluoronapthyl)borate]; [(3-perfluoromethyl-trifluorophenyl)(perfluoroethyl)(nonyl)phosphonium][tetrakis(perfluoromethylperfluoronaphthyl)aluminate]; [(2-methyl-6-perfluoromethyl-perfluorobiphenyl)(hexafluorononyl)(3-ethylheptyl)ammonium][tetraperfluorophenylborate]; [(biphenyl)(propyl)(2-methyl-5-propyl-heptyl)ammonium][tetrakis(perfluoroethylperfluorobiphenyl)borate]; [(hexafluorobiphenyl)(dipropyl)phosphonium][tetrakis(perfluorohexylperfluorophenyl)borate]; [(3-perfluoroethyl-trifluorophenyl)(methyl)(butyl)ammonium][tetrakis(3-ethylheptyl)borate]; [(3-perfluoroethyl-trifluorophenyl)(methyl)(butyl)ammonium][tetrakis(heptafluorofluorenyl)borate]; [(2-perfluoromethyl-6-perfluoroethyl-perfluorobiphenyl)(methyl)(2-methylpentyl)phosphonium][tetrakis(octafluorobiphenyl)aluminate]; [N-(1-fluorobiphenyl)pyrrolonium][tetraperfluorofluorenylborate]; [(perfluorobiphenyl)(diperfluoroethyl)phosphonium][tetrakis(pentafluoroindenyl)aluminate]; [(3-perfluoroethyl-trifluorophenyl)(2-methyl-5-propyl-heptyl)(methyl)phosphonium][tetrakis(2-methylpentyl)aluminate]; [(hexafluorobiphenyl)(fluoromethyl)(butyl)phosphonium][tetrakis(perfluoromethylperfluoronaphthyl)aluminate]; [(perfluorophenyl)(propyl)(ethyl)ammonium][tetrakis(hexafluorononyl)borate]; [N-(2,5-difluorophenyl)indolium][tetrakis(3-ethylheptyl)borate]; [(1-fluorobiphenyl)(methyl)(butyl)phosphonium][tetrakis(2-methylpentyl)borate]; [(octafluorobiphenyl)(hexyl)(fluoromethyl)phosphonium][tetraperfluoroanthracenylaluminate]; [(hexafluorobiphenyl)(2-methyl-5-propyl-heptyl)(ethyl)ammonium][tetrakis(octafluorobiphenyl)borate]; [(octafluorobiphenyl)(perfluoroethyl)(propyl)phosphonium][tetraperfluorophenylaluminate]; [(2,3-difluorophenyl)(hexafluorononyl)(ethyl)ammonium][tetraperfluorophenylaluminate]; [(1-fluorobiphenyl)(hexafluorononyl)(propyl)ammonium][tetrakis(perfluoropyrenyl)aluminate]; [(1-fluorobiphenyl)(3-ethylheptyl)(fluoromethyl)phosphonium][tetrakis(3-ethylheptyl)aluminate]; [(2,5-difluorophenyl)(propyl)(fluoromethyl)ammonium][tetrakis(ethylhexafluoronaphthyl)borate]; [(2-perfluoromethyl-6-perfluoroethyl-perfluorobiphenyl)(propyl)(2-methyl-5-propyl-heptyl)ammonium][tetrakis(ethylhexafluoronaphthyl)borate]; [(perfluorobiphenyl)(ethyl)(butyl)ammonium][tetraperfluoroanthracenylborate]; [(3-perfluoromethyl-trifluorophenyl)(butyl)(methyl)phosphonium][tetrakis(perfluoroethylperfluorobiphenyl)aluminate]; [(biphenyl)(butyl)(perfluoroethyl)ammonium][tetrahextylaluminate]; [(2-perfluoromethyl-6-perfluoroethyl-perfluorobiphenyl)(hexafluorononyl)(3-ethylheptyl)phosphonium][tetrakis(3-ethylheptyl)aluminate]; [(3-methylperfluorophenyl)(nonyl)(2-methyl-5-propyl-heptyl)ammonium][tetrakis(2-methylpentyl)aluminate]; [(2-perfluoromethyl-6-perfluoroethyl-perfluorobiphenyl)(nonyl)(2-methyl-5-propyl-heptyl)ammonium][tetraperfluorophenanthrylborate]; [(3-perfluorom ethyl-trifluorophenyl)(diethyl)ammonium][tetrakis(hexafluorononyl)borate]; [(2-methyl-6-perfluoromethyl-perfluorobiphenyl)(ethyl)(fluoromethyl)phosphonium][tetrakis(hexafluoronapthyl)borate]; [(hexafluorobiphenyl)(perfluoroethyl)(2-methyl-5-propyl-heptyl)ammonium][tetraperfluorophenylborate]; [(2-methyl-6-perfluoromethyl-perfluorobiphenyl)(2-methylpentyl)(ethyl)ammonium][tetrakis(3-ethylheptyl)aluminate]; [(2-methyl-6-perfluoromethyl-perfluorobiphenyl)(perfluoroethyl)(hexyl)phosphonium]-[tetrakis(pentafluoroindenyl)aluminate]; [(1-fluorobiphenyl)(2-methyl-5-propyl-heptyl)(methyl)ammonium][tetrakis(hexafluorononyl)aluminate]; [(biphenyl)(fluoromethyl)(methyl)phosphonium][tetrakis(perfluoropentylperfluorobiphenyl)borate]; [(3-methyl-perfluorophenyl)(2-methyl-5-propyl-heptyl)(propyl)phosphonium][tetrabutylaluminate]; [(perfluorobiphenyl)(2-methyl-5-propyl-heptyl)(3-ethylheptyl)ammonium][tetrakis(perfluoropyrenyl)borate]; [(2,4-difluorophenyl)(hexafluorononyl)(nonyl)ammonium][tetrakis(perfluoropyrenyl)aluminate]; [(2-perfluoromethyl-6-perfluoroethyl-perfluorobiphenyl)(2-methylpentyl)(perfluoroethyl)ammonium][tetrakis(heptafluorofluorenyl)aluminate]; [(3-perfluoromethyl-trifluorophenyl)(propyl)(2-methylpentyl)ammonium][tetrakis(perfluoropyrenyl)aluminate]; [(phenyl)(hexafluorononyl)(2-methyl-5-propyl-heptyl)ammonium][tetrakis(perfluoroethylperfluorobiphenyl)aluminate]; [(perfluorobiphenyl)(2-methylpentyl)(methyl)phosphonium][tetrabutylaluminate]; [(3-perfluoroethyl-trifluorophenyl)(2-methyl-5-propyl-heptyl)(3-ethylheptyl)ammonium][tetrakis(perfluoromethylperfluoronaphthyl)aluminate]; [(2,4-difluorophenyl)(methyl)(2-methyl-5-propyl-heptyl)ammonium][tetrakis(perfluoropentylperfluorobiphenyl)borate]; [(2,5-difluorophenyl)(hexyl)(perfluoroethyl)phosphonium][tetraperfluorophenylborate]; [N-(1-fluorobiphenyl)phosphapyrrolidinium][tetrakis(hexafluorononyl)borate]; [(2,3-difluorophenyl)(hexafluorononyl)(2-methylpentyl)phosphonium][tetrakis(hexafluorononyl)aluminate]; [(phenyl)(2-methyl-5-propyl-heptyl)(hexafluorononyl)ammonium][tetraperfluorophenylaluminate]; [(2,4-difluorophenyl)(butyl)(2-methylpentyl)ammonium][tetrakis(octafluorobiphenyl)borate]; [(2-methyl-6-perfluoromethyl-perfluorobiphenyl)(butyl)(perfluoroethyl)phosphonium][tetrakis(perfluoropentylperfluorobiphenyl)aluminate]; [(2,5-difluorophenyl)(butyl)(hexyl)ammonium][tetrakis(perfluoropyrenyl)borate]; [(phenyl)(perfluoroethyl)(fluoromethyl)ammonium][tetrakis(perfluoroethylperfluorobiphenyl)borate]; [(2,3-difluorophenyl)(3-ethylheptyl)(perfluoroethyl)ammonium][tetrahextylborate]; [(1-fluorobiphenyl)(fluoromethyl)(ethyl)ammonium][tetrakis(perfluorohexylperfluorophenyl)aluminate]; [(2,5-difluorophenyl)(hexafluorononyl)(methyl)ammonium][tetraperfluorophenylaluminate]; [(2,5-difluorophenyl)(dimethyl)ammonium][tetrakis(hexafluoroindenyl)borate]- [(3-perfluoromethyl-trifluorophenyl)(dihexyl)ammonium][tetrakis(ethylhexafluoronaphthyl)aluminate]; [(hexafluorobiphenyl)(3-ethylheptyl)(hexafluorononyl)phosphonium][tetraperfluorophenylborate]; [(2-methyl-6-perfluoromethylperfluorobiphenyl)(fluoromethyl)(perfluoroethyl)phosphonium][tetrakis(perfluorobiphenyl)aluminate]; [(2-perfluoromethyl-6-perfluoroethylperfluorobiphenyl)(2-methyl-5-propyl-heptyl)(hexafluorononyl)ammonium][tetrakis(perfluoropentylperfluorobiphenyl)aluminate]; [(hexafluorobiphenyl)(hexafluorononyl)(methyl)ammonium][tetrakis(methylperfluoronaphthyl)borate]; [(2-perfluoromethyl-6-perfluoroethyl-perfluorobiphenyl)(hexafluorononyl)(2-methyl-5-propyl-heptyl)ammonium]

[tetrakis(2-methyl-5-propyl-heptyl)aluminate]; [(3-perfluoroethyl-trifluorophenyl)(2-methyl-5-propyl-heptyl)(3-ethylheptyl)ammonium][tetrakis(heptafluorofluorenyl)borate]; [(tetrafluorophenyl)(hexafluorononyl)(2-methylpentyl)phosphonium][tetrakis(perfluorohexylperfluorophenyl)borate]; [(2-perfluoromethyl-6-perfluoroethyl-perfluorobiphenyl)(hexafluorononyl)(2-methylpentyl)ammonium][tetranonylborate]; [(hexafluorobiphenyl)(3-ethylheptyl)(2-methylpentyl)ammonium][tetrakis(pentafluoronaphthyl)borate]; [(2,4-difluorophenyl)(diethyl)ammonium][tetrakis(methylperfluoronaphthyl)aluminate]; [(3-perfluoroethyl-trifluorophenyl)(hexafluorononyl)(propyl)ammonium][tetranonylborate]; [(tetrafluorophenyl)(3-ethylheptyl)(hexafluorononyl)ammonium][tetrakis(hexafluoronapthyl)borate]; [(3-methyl-perfluorophenyl)(3-ethylheptyl)(methyl)ammonium][tetrakis(hexafluoroindenyl)aluminate]; [(3-methyl-perfluorophenyl)(hexafluorononyl)(3-ethylheptyl)ammonium][tetranonylborate]; [(tetrafluorophenyl)(fluoromethyl)(2-methyl-5-propyl-heptyl)ammonium][tetraperfluorophenylaluminate]; [N-(2,5-difluorophenyl)pyrrolium][tetraheptylborate]; [(perfluorophenyl)(butyl)(nonyl)ammonium][tetrahextylborate]; [(perfluorophenyl)(perfluoroethyl)(hexafluorononyl)phosphonium][tetranonylborate]; [(hexafluorobiphenyl)(3-ethylheptyl)(butyl)phosphonium][tetrakis(2-methylpentyl)aluminate]; [(3-perfluoromethyl-trifluorophenyl)(dihexyl)ammonium][tetrakis(pentafluoroindenyl)borate]; [(perfluorobiphenyl)(di2-methyl-5-propyl-heptyl)phosphonium][tetraheptylborate]; [(perfluorobiphenyl)(2-methylpentyl)(ethyl)ammonium][tetrakis(ethylhexafluoronaphthyl)aluminate]; [(2,4-difluorophenyl)(hexyl)(nonyl)ammonium][tetrakis(2-methyl-5-propyl-heptyl)borate]; [(phenyl)(dimethyl)ammonium][tetrapentylaluminate]; [(1-fluorophenyl)(ethyl)(nonyl)ammonium][tetrakis(octafluorobiphenyl)borate]; [N-(2-methyl-6-perfluoromethyl-perfluorobiphenyl)phosphindolinium][tetraperfluorophenylborate]; [(3-perfluoroethyl-trifluorophenyl)(dihexyl)ammonium][tetrakis(hexafluoroindenyl)aluminate]; [(2,3-difluorophenyl)(nonyl)(2-methyl-5-propyl-heptyl)phosphonium][tetrakis(perfluoropyrenyl)borate]; [(3-perfluoroethyl-trifluorophenyl)(hexyl)(methyl)ammonium][tetraperfluorophenanthrylborate]; [(2-methyl-6-perfluoromethyl-perfluorobiphenyl)(2-methylpentyl)(hexyl)ammonium][tetrabutylborate]; [(3-methyl-perfluoro-5-phenyl)(2-methylpentyl)(nonyl)ammonium][tetrakis(perfluoropyrenyl)aluminate]; [(2-methyl-6-perfluoromethyl-perfluorobiphenyl)(diperfluoroethyl)ammonium][tetrabutylborate]; [(3-methyl-perfluorophenyl)(nonyl)(3-ethylheptyl)ammonium][tetrakis(perfluoroethylperfluorobiphenyl)borate]; [(1-fluorophenyl)(methyl)(3-ethylheptyl)ammonium][tetraperfluoroanthracenylborate]; [(octafluorobiphenyl)(2-methylpentyl)(butyl)ammonium][tetranonylborate]; [(2-methyl-6-perfluoromethyl-perfluorobiphenyl)(2-methyl-5-propyl-heptyl)(2-methylpentyl)ammonium][tetrabutylaluminate]; [(octafluorobiphenyl)(ethyl)(propyl)ammonium][tetrakis(methylperfluoronaphthyl)borate]; [(3-methyl-perfluorophenyl)(2-methyl-5-propyl-heptyl)(fluoromethyl)ammonium][tetraperfluorophenanthrylborate]; [(phenyl)(2-methylpentyl)(butyl)ammonium][tetraperfluorophenylborate]; [N-(phenyl)pyrrolonium][tetraheptylborate]; [(1-fluorophenyl)(ethyl)(2-methylpentyl)ammonium][tetrakis(octafluorobiphenyl)aluminate]; [(biphenyl)(perfluoroethyl)(propyl)ammonium][tetraperfluorophenanthrylaluminate]; [(3-perfluoromethyl-trifluorophenyl)(2-methyl-5-propyl-heptyl)(2-methylpentyl)ammonium][tetrakis(perfluorohexylperfluorophenyl)aluminate]; [(2,3-difluorophenyl)(hexyl)(methyl)ammonium][tetrakis(pentafluoroindenyl)borate]; [(biphenyl)(propyl)(butyl)ammonium][tetrapentylborate]; [(2-perfluoromethyl-6-perfluoroethyl-perfluorobiphenyl)(hexafluorononyl)(fluoromethyl)ammonium][tetrahextylaluminate]; [(3-methyl-perfluorophenyl)(dimethyl)ammonium][tetrakis(2-methylpentyl)borate]; [(2,3-difluorophenyl)(propyl)(methyl)ammonium][tetraperfluorophenylaluminate]; [(2-perfluoromethyl-6-perfluoroethyl-perfluorobiphenyl)(propyl)(2-methyl-5-propyl-heptyl)ammonium][tetrakis(hexafluorononyl)aluminate]; [(perfluorophenyl)(hexyl)(2-methyl-5-propyl-heptyl)ammonium][tetrakis(hexafluoronapthyl)borate]; [(1-fluorobiphenyl)(methyl)(2-methyl-5-propyl-heptyl)ammonium][tetrakis(hexafluorononyl)borate]; [(biphenyl)(2-methylpentyl)(2-methyl-5-propyl-heptyl)ammonium][tetraperfluorofluorenylaluminate]; [(perfluorophenyl)(propyl)(nonyl)ammonium][tetranonylaluminate]; [(biphenyl)(hexafluorononyl)(perfluoroethyl)ammonium][tetrakis(perfluoroethylperfluorobiphenyl)aluminate]; [(2-methyl-6-perfluoromethyl-perfluorobiphenyl)(hexafluorononyl)(ethyl)phosphonium][tetrakis(perfluoronaphthyl)borate]; [(2,3-difluorophenyl)(nonyl)(hexafluorononyl)ammonium][tetrakis(perfluoropentylperfluorobiphenyl)borate]; [(2,5-difluorophenyl)(propyl)(hexyl)ammonium][tetrapentylaluminate]; [N-(octafluorobiphenyl)piperidinium][tetraheptylaluminate]; [(phenyl)(3-ethylheptyl)(2-methylpentyl)ammonium][tetrakis(heptafluorofluorenyl)aluminate]; [(biphenyl)(hexafluorononyl)(methyl)ammonium][tetraperfluoroanthracenylborate]; [(2,5-difluorophenyl)(propyl)(nonyl)phosphonium][tetraperfluoroindenylborate]; [N-(3perfluoromethyl-trifluorophenyl)phosphapyrrolidinium][tetrakis(perfluoromethylperfluoronaphthyl)borate]; [(1-fluorobiphenyl)(diperfluoroethyl)phosphonium][tetrakis(hexafluoronapthyl)aluminate]; [(3-methyl-perfluorophenyl)(nonyl)(2-methyl-5-propyl-heptyl)ammonium][tetrakis(pentafluoroindenyl)aluminate]; [N-(3-methyl-perfluorophenyl)pyrrolium][tetrakis(2-methylpentyl)borate]; [(perfluorophenyl)(methyl)(3-ethylheptyl)ammonium][tetrabutylaluminate]; [(tetrafluorophenyl)(propyl)(2-methyl-5-propyl-heptyl)ammonium][tetrakis(methyloctafluorbiphenyl)aluminate]; [(2-perfluoromethyl-6-perfluoroethyl-perfluorobiphenyl)(perfluoroethyl)(hexafluorononyl)ammonium][tetrakis(2-methylpentyl)borate]; [(2,3-difluorophenyl)(ethyl)(2-methylpentyl)ammonium][tetrakis(hexafluoronapthyl)borate]; [(1-fluorobiphenyl)(2-methyl-5-propyl-heptyl)(3-ethylheptyl)ammonium][tetraperfluoroanthracenylaluminate]; [N-(2,5-difluorophenyl)piperidinium][tetraperfluorofluorenylaluminate]; [(perfluorobiphenyl)(2-methyl-5-propyl-heptyl)(hexyl)ammonium][tetrakis(perfluorohexylperfluorophenyl)aluminate]; [(octafluorobiphenyl)(dihexyl)phosphonium][tetrakis(ethylhexafluoronaphthyl)aluminate][(biphenyl)(fluoromethyl)(2-methyl-5-propyl-heptyl)ammonium][tetrabutylaluminate]; [(3-perfluoroethyl-trifluorophenyl)(methyl)(hexafluorononyl)phosphonium][tetrakis(octafluorobiphenyl)aluminate]; [(perfluorophenyl)(methyl)(hexyl)phosphonium][tetrakis(hexafluorononyl)borate]; [(3- perfluoromethyl-trifluorophenyl)(perfluoroethyl)(hexafluorononyl)ammonium][tetraoctylborate]; [(2,4-difluorophenyl)(hexafluorononyl)(ethyl)phosphonium][tetrakis(perfluorohexylperfluorophenyl)aluminate]; [(tetrafluorophenyl)(ethyl)(methyl)ammonium][tetraperfluorophenanthrylaluminate]; [(3-methyl-perfluorophenyl)(hexyl)(2-methyl-5-propyl-heptyl)ammonium][tetrakis(perfluorobiphenyl)aluminate]; [N-(perfluorobiphenyl)indolinium][tetrakis(heptafluorofluorenyl)aluminate]; [(biphenyl)(methyl)(butyl)ammonium][tetrakis(perfluorobiphenyl)borate]; [(perfluorobiphenyl)(2-methylpentyl)(methyl)ammonium][tetrakis(ethylhexafluoronaphthyl)aluminate]; [(phenyl)(hexafluorononyl)(3-ethylheptyl)ammonium][tetrakis(methylperfluoronaphthyl)aluminate]; [(2,4-difluorophenyl)(butyl)(propyl)ammonium][tetrakis(methyloctafluorbiphenyl)aluminate]; [(3-perfluoroethyl-trifluorophenyl)(fluoromethyl)(perfluoroethyl)ammonium][tetrakis(3-ethylheptyl)aluminate]; [(biphenyl)(methyl)(hexafluorononyl)ammonium][tetrakis(pentafluoroindenyl)borate]; [(2-perfluoromethyl-6-perfluoroethylperfluorobiphenyl)(propyl)(ethyl)ammonium][tetrakis(heptafluorofluorenyl)borate]; [(tetrafluorophenyl)(2-methylpentyl)(perfluoroethyl)phosphonium][tetrakis(ethylhexafluoronaphthyl)borate]; [(2-perfluoromethyl-6-perfluoroethyl-perfluorobiphenyl)(fluoromethyl)(ethyl)phosphonium][tetrakis(3-ethylheptyl)aluminate]; [(2-methyl-6-perfluoromethyl-perfluorobiphenyl)(nonyl)(hexafluorononyl)ammonium][tetraheptylaluminate]; [(2-perfluoromethyl-6-perfluoroethyl-perfluorobiphenyl)(perfluoroethyl)(methyl)ammonium][tetraperfluoroanthracenylborate]; [(2,3-difluorophenyl)(2-methylpentyl)(fluoromethyl)phosphonium][tetraheptylborate]; [(perfluorophenyl)(nonyl)(2-methylpentyl)phosphonium][tetrahextylborate]; [(3-perfluoroethyl-trifluorophenyl)(methyl)(propyl)phosphonium][tetrakis(hexafluorononyl)borate]; [(2,5-difluorophenyl)(2-methylpentyl)(2-methyl-5-propyl-heptyl)phosphonium][tetrakis(perfluoroethylperfluorobiphenyl)aluminate]; [(1-fluorophenyl)(nonyl)(butyl)ammonium][tetrakis(perfluorobiphenyl)aluminate]; [(3-perfluoromethyl-trifluorophenyl)(2-methyl-5-propyl-heptyl)(2-methylpentyl)phosphonium][tetraperfluorophenylaluminate]; [(2,5-difluorophenyl)(propyl)(2-methylpentyl)phosphonium][tetrakis(pentafluoroindenyl)aluminate]; [(2,5-difluorophenyl)(butyl)(methyl)phosphonium][tetrakis(perfluoromethylperfluoronaphthyl)borate]; [(2,4-difluorophenyl)(2-methylpentyl)(hexafluorononyl)ammonium][tetrakis(perfluoromethylperfluoronaphthyl)aluminate]; [(3-methyl-perfluorophenyl)(2-methylpentyl)(fluoromethyl)ammonium][tetrabutylaluminate]; [(perfluorophenyl)(dihexafluorononyl)phosphonium][tetraperfluoroanthracenylborate]; [(tetrafluorophenyl)(butyl)(perfluoroethyl)ammonium][tetrakis(perfluoropyrenyl)borate]; [(phenyl)(3-ethylheptyl)(2-methylpentyl)ammonium][tetraheptylaluminate]; [(biphenyl)(hexyl)(ethyl)phosphonium][tetraheptylaluminate]; [N-(2,3-difluorophenyl)phosphindolinium][tetrakis(2-methylpentyl)aluminate]; [(2-methyl-6-perfluoromethyl-perfluorobiphenyl)(methyl)(butyl)ammonium][tetraperfluorophenylaluminate]; [(2,3-difluorophenyl)(hexyl)(fluoromethyl)ammonium][tetrahextylborate]; [N-(3-methyl-perfluorophenyl)indolium][tetrakis(octafluorobiphenyl)aluminate]; [(perfluorobiphenyl)(2-methylpentyl)(3-ethylheptyl)ammonium][tetrakis(methylperfluoronaphthyl)aluminate]; [(2,3-difluorophenyl)(2-methylpentyl)(hexafluorononyl)phosphonium][tetraoctylborate]; [(2-methyl-6-perfluoromethyl-perfluorobiphenyl)(ethyl)(2-methylpentyl)ammonium][tetrakis(hexafluorononyl)aluminate]; [(2-perfluoromethyl-6-perfluoroethyl-perfluorobiphenyl)(3-ethylheptyl)(hexafluorononyl)ammonium][tetraperfluoroindenylaluminate]; [(2-perfluoromethyl-6-perfluoroethyl-perfluorobiphenyl)(perfluoroethyl)(hexyl)phosphonium][tetrakis(2-methyl-5-propyl-heptyl)borate]; [(biphenyl)(perfluoroethyl)(propyl)ammonium][tetraperfluoroindenylborate]; [(2-methyl-6-perfluoromethyl-perfluorobiphenyl)(di3-ethylheptyl)ammonium][tetraperfluoroanthracenylborate]; [(1-fluorophenyl)(di2-methylpentyl)ammonium][tetrakis(perfluoromethylperfluoronaphthyl)aluminate]; [(octafluorobiphenyl)(2-methylpentyl)(propyl)phosphonium][tetraoctylborate]; [(3-perfluoromethyltrifluorophenyl)(2-methyl-5-propyl-heptyl)(nonyl)phosphonium][tetraperfluoroindenylaluminate]; [(biphenyl)(methyl)(nonyl)ammonium][tetrakis(octafluorobiphenyl)borate]; [(hexafluorobiphenyl)(di2-methylpentyl)ammonium][tetrakis(2-methylpentyl)aluminate]; [(perfluorobiphenyl)(propyl)(butyl)phosphonium][tetraperfluorophenanthrylaluminate]; [(2,4-difluorophenyl)(hexyl)(methyl)phosphonium][tetraheptylborate]; [(2-methyl-6-perfluoromethyl-perfluorobiphenyl)(ethyl)(hexyl)ammonium][tetrakis(3-ethylheptyl)borate]; [(3-methyl-perfluorophenyl)(nonyl)(methyl)ammonium][tetrakis(hexafluoroindenyl)borate]; [(2-perfluoromethyl-6-perfluoroethyl-perfluorobiphenyl)(hexafluorononyl)(3-ethylheptyl)ammonium][tetrakis(perfluoronaphthyl)aluminate]; [N-(1-fluorophenyl)pyrrolium][tetrabutylborate]; [(biphenyl)(2-methyl-5-propyl-heptyl)(methyl)phosphonium][tetrabutylaluminate]; [(perfluorophenyl)(methyl)(hexafluorononyl)phosphonium][tetrakis(hexafluoronapthyl)aluminate]; [(tetrafluorophenyl)(butyl)(ethyl)phosphonium][tetraperfluorophenylborate]; [N-(2,4-difluorophenyl)pyrrolidinium][tetrakis(perfluoromethylperfluoronaphthyl)borate]; [(3-methyl-perfluorophenyl)(difluoromethyl)ammonium][tetrakis(perfluoronaphthyl)aluminate]; [(perfluorobiphenyl)(propyl)(hexafluorononyl)ammonium][tetrakis(methylperfluoronaphthyl)aluminate]; [(1-fluorophenyl)(hexafluorononyl)(butyl)phosphonium][tetrakis(heptafluorofluorenyl)borate]; [(2-methyl-6-perfluoromethyl-perfluorobiphenyl)(3-ethylheptyl)(ethyl)phosphonium][tetrakis(perfluoropentylperfluorobiphenyl)aluminate]; [(tetrafluorophenyl)(diethyl)phosphonium][tetraoctylaluminate]; [(2-methyl-6-perfluoromethyl-perfluorobiphenyl)(2-methyl-5-propyl-heptyl)(butyl)phosphonium][tetrakis(methyloctafluorbiphenyl)aluminate]; [(hexafluorobiphenyl)(perfluoroethyl)(hexafluorononyl)phosphonium][tetrakis(pentafluoroindenyl)borate]; [(hexafluorobiphenyl)(methyl)(butyl)phosphonium][tetrapentylborate]; [(2,5-difluorophenyl)(perfluoroethyl)(fluoromethyl)ammonium][tetraperfluoroindenylaluminate]; [(1-fluorophenyl)(ethyl)(butyl)phosphonium][tetrakis(pentafluoroindenyl)aluminate]; [(biphenyl)(3-ethylheptyl)(propyl)ammonium][tetrakis(heptafluorofluorenyl)aluminate]; [(hexafluorobiphenyl)(dipropyl)ammonium][tetrakis(methyloctafluorbiphenyl)borate]; [(1-fluorobiphenyl)(methyl)(butyl)phosphonium][tetrakis(2-methylpentyl)aluminate]; [(biphenyl)(propyl)(2-methyl-5-propyl-heptyl)phosphonium][tetraheptylborate]; [(tetrafluorophenyl)(2-methyl-5-propyl-heptyl)(2-methylpentyl)phosphonium][tetrakis(perfluorohexylperfluorophenyl)aluminate];

[(tetrafluorophenyl)(hexafluorononyl)(ethyl)phosphonium][tetrakis(perfluoroethylperfluorobiphenyl)borate]; [(2,3-difluorophenyl)(dibutyl)ammonium][tetrakis(perfluorohexylperfluorophenyl)borate]; [(3-perfluoroethyl-trifluorophenyl)(methyl)(ethyl)ammonium][tetraoctylaluminate]; [(2,3-difluorophenyl)(fluoromethyl)(nonyl)phosphonium][tetraperfluoroanthracenylborate]; [(phenyl)(hexafluorononyl)(hexyl)phosphonium][tetrakis(3-ethylheptyl)aluminate]; [(octafluorobiphenyl)(hexyl)(3-ethylheptyl)ammonium][tetrakis(heptafluorofluorenyl)borate]; [(2,5-difluorophenyl)(3-ethylheptyl)(hexyl)ammonium][tetrakis(perfluorohexylperfluorophenyl)borate]; [N-(3-perfluoroethyl-trifluorophenyl)pyrrolium][tetraperfluoroanthracenylborate]; [(1-fluorophenyl)(fluoromethyl)(nonyl)phosphonium][tetrakis(perfluorobiphenyl)aluminate]; [(3-methyl-perfluorophenyl)(2-methylpentyl)(hexyl)ammonium][tetrakis(3-ethylheptyl)borate]; [(perfluorobiphenyl)(hexyl)(ethyl)phosphonium][tetrakis(heptafluorofluorenyl)borate]; [(1-fluorobiphenyl)(2-methylpentyl)(hexyl)ammonium][tetrakis(perfluoroethylperfluorobiphenyl)borate]; [(3-perfluoroethyl-trifluorophenyl)(hexyl)(ethyl)ammonium][tetrakis(perfluoronaphthyl)aluminate]; [(3-perfluoromethyl-trifluorophenyl)(hexyl)(propyl)ammonium][tetrakis(perfluoronaphthyl)borate]; [(biphenyl)(methyl)(hexyl)phosphonium][tetrakis(2-methyl-5-propyl-heptyl)aluminate]; [(perfluorobiphenyl)(2-methylpentyl)(3-ethylheptyl)ammonium][tetraperfluorophenanthrylaluminate]; [(3-perfluoroethyltrifluorophenyl)(dimethyl)ammonium][tetrakis(heptafluorofluorenyl)aluminate]; [(3-methyl-perfluorophenyl)(hexafluorononyl)(2-methyl-5-propyl-heptyl)phosphonium][tetraheptylborate]; [(1-fluorobiphenyl)(2-methylpentyl)(hexyl)phosphonium][tetrakis(perfluoroethylperfluorobiphenyl)aluminate]; [(phenyl)(hexafluorononyl)(propyl)ammonium][tetrakis(perfluorobiphenyl)aluminate]; [(tetrafluorophenyl)(2-methylpentyl)(perfluoroethyl)phosphonium][tetrakis(hexafluoroindenyl)borate]; [(2,5-difluorophenyl)(fluoromethyl)(hexyl)ammonium]-[tetrakis(perfluoropentylperfluorobiphenyl)borate]; [(1-fluorophenyl)(dinonyl)phosphonium][tetrakis(hexafluoronapthyl)aluminate]; [(hexafluorobiphenyl)(dibutyl)phosphonium][tetraheptylaluminate]; [(1-fluorophenyl)(propyl)(perfluoroethyl)ammonium][tetraperfluorophenanthrylaluminate]; [(hexafluorobiphenyl)(methyl)(2-methyl-5-propyl-heptyl)ammonium][tetrakis(methyloctafluorbiphenyl)aluminate]; [(3-perfluoromethyl-trifluorophenyl)(perfluoroethyl)(butyl)phosphonium][tetrakis(perfluoroethylperfluorobiphenyl)aluminate]; [(biphenyl)(fluoromethyl)(2-methyl-5-propyl-heptyl)ammonium][tetrakis(heptafluorofluorenyl)borate]; [N-(phenyl)indolium][tetraperfluorophenanthrylaluminate]; [(tetrafluorophenyl)(dipropyl)phosphonium][tetraperfluorophenylborate]; [(2,3-difluorophenyl)(3-ethylheptyl)(perfluoroethyl)ammonium][tetraperfluorofluorenylborate]; [(2-perfluoromethyl-6-perfluoroethyl-perfluorobiphenyl)(hexafluorononyl)(perfluoroethyl)phosphonium][tetrakis(methyloctafluorbiphenyl)aluminate]; [N-(phenyl)pyrrolium][tetrakis(methyloctafluorbiphenyl)aluminate]; [N-(2-methyl-6-perfluoromethylperfluorobiphenyl)phosphindolium][tetranonylaluminate]; [(3-perfluoroethyltrifluorophenyl)(dipropyl)phosphonium][tetrakis(heptafluorofluorenyl)aluminate]; [(1-fluorobiphenyl)(perfluoroethyl)(nonyl)phosphonium][tetraheptylborate]; [(3-methyl-perfluorophenyl)(nonyl)(fluoromethyl)ammonium][tetraperfluorophenylaluminate]; [(3-perfluoroethyl-trifluorophenyl)(hexyl)(fluoromethyl)ammonium][tetrakis(ethylhexafluoronaphthyl)borate]; [(2,3-difluorophenyl)(di2-methylpentyl)phosphonium][tetrakis(ethylhexafluoronaphthyl)borate]; [(phenyl)(hexyl)(2-methylpentyl)phosphonium][tetraoctylborate]; [(octafluorobiphenyl)(dibutyl)ammonium][tetraperfluorophenanthrylborate]; [(octafluorobiphenyl)(nonyl)(propyl)ammonium][tetranonylborate]; [(1-fluorobiphenyl)(3-ethylheptyl)(hexyl)phosphonium][tetrakis(perfluoromethylperfluoronaphthyl)aluminate]; [(tetrafluorophenyl)(ethyl)(methyl)ammonium][tetrakis(methylperfluoronaphthyl)borate]; [(2-perfluoromethyl-6-perfluoroethylperfluorobiphenyl)(perfluoroethyl)(butyl)ammonium][tetrakis(2-methyl-5-propyl-heptyl)borate]; [(2-methyl-6-perfluoromethyl-perfluorobiphenyl)(dipropyl)ammonium][tetrakis(pentafluoronaphthyl)aluminate]; [(3-methyl-perfluorophenyl)(ethyl)(3-ethylheptyl)ammonium][tetrakis(octafluorobiphenyl)aluminate]; [(2-perfluoromethyl-6-perfluoroethyl-perfluorobiphenyl)(butyl)(2-methyl-5-propyl-heptyl)ammonium][tetrakis(perfluoropyrenyl)borate]; [(1-fluorobiphenyl)(3-ethylheptyl)(hexyl)phosphonium][tetrakis(2-methyl-5-propyl-heptyl)borate]; [(2,4-difluorophenyl)(hexafluorononyl)(3-ethylheptyl)phosphonium][tetrakis(octafluorobiphenyl)aluminate]; [N-(biphenyl)pyrrolium][tetraoctylborate]; [(2,3-difluorophenyl)(propyl)(2-methyl-5-propyl-heptyl)phosphonium][tetrakis(2-methylpentyl)aluminate]; [(perfluorobiphenyl)(dihexyl)ammonium][tetrakis(perfluorobiphenyl)aluminate]; [(2,4-difluorophenyl)(ethyl)(hexyl)ammonium][tetrakis(perfluoroethylperfluorobiphenyl)borate]; [(2-methyl-6-perfluoromethyl-perfluorobiphenyl)(ethyl)(2-methylpentyl)phosphonium][tetrakis(2-methyl-5-propyl-heptyl)aluminate]; [N-(perfluorophenyl)pyrrolonium][tetraperfluorofluorenylborate]; [(1-fluorobiphenyl)(butyl)(nonyl)ammonium][tetrakis(pentafluoroindenyl)aluminate]; [(2,3-difluorophenyl)(ethyl)(butyl)phosphonium][tetrakis(perfluoroethylperfluorobiphenyl)borate]; [(2,4-difluorophenyl)(butyl)(3-ethylheptyl)phosphonium][tetraperfluoroanthracenylaluminate]; [(octafluorobiphenyl)(fluoromethyl)(perfluoroethyl)phosphonium][tetrabutylborate]; [(2,4-difluorophenyl)(fluoromethyl)(hexyl)ammonium][tetraperfluorofluorenylborate]; [(2,5-difluorophenyl)(hexafluorononyl)(ethyl)ammonium][tetrakis(perfluoroethylperfluorobiphenyl)borate]; [(2-methyl-6-perfluoromethyl-perfluorobiphenyl)(propyl)(perfluoroethyl)ammonium][tetraperfluoroanthracenylborate]; [(2-perfluoromethyl-6-perfluoroethyl-perfluorobiphenyl)(diperfluoroethyl)ammonium][tetraoctylborate]; [(2-methyl-6-perfluoromethyl-perfluorobiphenyl)(2-methylpentyl)(2-methyl-5-propyl-heptyl)ammonium][tetrakis(octafluorobiphenyl)aluminate]; [(perfluorophenyl)(hexyl)(2-methyl-5-propyl-heptyl)ammonium][tetraperfluorophenylborate]; [(biphenyl)(propyl)(butyl)ammonium][tetrakis(hexafluorononyl)aluminate]; [(phenyl)(butyl)(2-methyl-5-propyl-heptyl)ammonium][tetrakis(methylperfluoronaphthyl)borate]; [(perfluorobiphenyl)(propyl)(fluoromethyl)phosphonium][tetrakis(2-methyl-5-propyl-heptyl)aluminate]; [(2,3-difluorophenyl)(hexyl)(3-ethylheptyl)phosphonium][tetrakis(hexafluoroindenyl)borate]; [(2-methyl-6-perfluoromethyl-perfluorobiphenyl)(nonyl)(perfluoroethyl)phosphonium][tetrakis(2-methyl-5-propyl-heptyl)aluminate]; [(octafluorobiphenyl)(methyl)(2-methylpentyl)ammonium][tetrahexylborate]; [(biphenyl)(dihexyl)ammonium][tetraheptylborate];

[(tetrafluorophenyl)(methyl)(2-methyl-5-propyl-heptyl) ammonium][tetrakis(hexafluorononyl)borate]; [(1-fluorobiphenyl)(nonyl)(propyl)ammonium] [tetraperfluorofluorenylaluminate]; [(hexafluorobiphenyl) (nonyl)(hexyl)ammonium][tetrakis (perfluoropentylperfluorobiphenyl)borate]; [N-(2,4-difluorophenyl)indolium][tetranonylaluminate]; [(2-perfluoromethyl-6-perfluoroethyl-perfluorobiphenyl) (propyl)(hexyl)ammonium] [tetraperfluorofluorenylaluminate]; [(1-fluorophenyl)(2-methyl-5-propyl-heptyl)(methyl)phosphonium][tetrakis (hexafluorononyl)borate]; [(octafluorobiphenyl)(propyl)(3-ethylheptyl)ammonium][tetrakis(3-ethylheptyl)borate]; [(biphenyl)(nonyl)(ethyl)ammonium] [tetrapentylaluminate]; [(2,5-difluorophenyl)(propyl)(ethyl) ammonium][tetrahextylborate]; [N-(3-perfluoroethyltrifluorophenyl)pyrrolidinium] [tetranonylaluminate]; [(1-fluorophenyl)(2-methylpentyl) (nonyl)ammonium][tetraperfluorophenylborate]; [(2,3-difluorophenyl)(2-methylpentyl)(hexafluorononyl) ammonium][tetrakis(2-methyl-5-propyl-heptyl)aluminate]; [(2-perfluoromethyl-6-perfluoroethyl-perfluorobiphenyl) (hexafluorononyl)(2-methyl-5-propyl-heptyl)ammonium] [tetrakis(perfluoropentylperfluorobiphenyl)borate]; [(perfluorobiphenyl)(ethyl)(perfluoroethyl)ammonium] [tetrakis(hexafluoronapthyl)borate]; [(2,5-difluorophenyl) (dibutyl)ammonium][tetraperfluoroindenylborate]; [(2-methyl-6-perfluoromethyl-perfluorobiphenyl) (fluoromethyl)(2-methyl-5-propyl-heptyl)phosphonium] [tetrakis(heptafluorofluorenyl)aluminate]; [(tetrafluorophenyl)(nonyl)(butyl)phosphonium][tetrakis(2-methylpentyl)borate]; [(hexafluorobiphenyl) (hexafluorononyl)(propyl)ammonium][tetrakis (pentafluoronaphthyl)borate]; [(phenyl)(hexafluorononyl) (2-methyl-5-propyl-heptyl)ammonium] [tetraperfluorophenylborate]; [(tetrafluorophenyl)(hexyl) (fluoromethyl)phosphonium][tetrakis (methyloctafluorbiphenyl)aluminate]; [(perfluorobiphenyl) (3-ethylheptyl)(butyl)ammonium][tetrakis (perfluorohexylperfluorophenyl)borate]; [(2,3-difluorophenyl)(fluoromethyl)(3-ethylheptyl)ammonium] [tetranonylborate]; [(tetrafluorophenyl)(3-ethylheptyl)(2-methyl-5-propyl-heptyl)phosphonium][tetrakis (perfluoromethylperfluoronaphthyl)aluminate]; [N-(perfluorobiphenyl)pyrrolidinium][tetrakis (perfluoronaphthyl)aluminate]; [(3-methylperfluorophenyl) (nonyl)(3-ethylheptyl)ammonium][tetrakis (hexafluoroindenyl)aluminate]; [(hexafluorobiphenyl)(2-methylpentyl)(fluoromethyl)phosphonium][tetrakis (perfluoropyrenyl)aluminate]; [(octafluorobiphenyl)(hexyl) (perfluoroethyl)ammonium][tetrakis(perfluoropyrenyl) aluminate]; [N-(2,5-difluorophenyl)pyrrolonium] [tetraperfluoroanthracenylaluminate]; [(2-perfluoromethyl-6-perfluoroethyl-perfluorobiphenyl)(perfluoroethyl)(butyl) ammonium][tetrakis(methylperfluoronaphthyl)aluminate]; [(tetrafluorophenyl)(2-methyl-5-propyl-heptyl) (perfluoroethyl)ammonium][tetrakis (perfluoromethylperfluoronaphthyl)aluminate]; difluorophenyl)(fluoromethyl)(hexafluorononyl) ammonium][tetraperfluorophenanthrylborate]; [N-(phenyl) pyrrolonium][tetrakis(2-methyl-5-propyl-heptyl)borate]; [(1-fluorophenyl)(fluoromethyl)(perfluoroethyl) phosphonium][tetrakis(perfluoronaphthyl)aluminate]; [(2,3-difluorophenyl)(butyl)(2-methylpentyl)phosphonium] [tetrakis(perfluoropentylperfluorobiphenyl)borate]; [(2,5-difluorophenyl)(hexafluorononyl)(methyl)ammonium] [tetraperfluorofluorenylaluminate]; [(1-fluorobiphenyl)(2-methyl-5-propyl-heptyl)(fluoromethyl)phosphonium] [tetrakis(perfluorohexylperfluorophenyl)borate]; [(3-methyl-perfluorophenyl)(fluoromethyl)(propyl)ammonium] [tetraoctylborate]; [(3-methyl-perfluorophenyl)(methyl) (nonyl)ammonium][tetrakis(2-methylpentyl)aluminate]; [(1-fluorobiphenyl)(2-methyl-5-propyl-heptyl)(ethyl) ammonium][tetrakis(perfluoropentylperfluorobiphenyl) borate]; [(1-fluorobiphenyl)(propyl)(methyl)ammonium] [tetrakis(2-methyl-5-propyl-heptyl)borate]; [(phenyl)(3-ethylheptyl)(nonyl)ammonium][tetrakis (ethylhexafluoronaphthyl)borate]; [(2-methyl-6-perfluoromethylperfluorobiphenyl)(nonyl)(perfluoroethyl) phosphonium][tetrabutylaluminate]; [(tetrafluorophenyl) (methyl)(hexafluorononyl)ammonium][tetrakis (heptafluorofluorenyl)borate]; [(1-fluorophenyl)methyl) (hexyl)phosphonium][tetrakis(perfluoropyrenyl)borate]; [(2,4-difluorophenyl)(fluoromethyl)(ethyl)ammonium] [tetrakis(hexafluorononyl)borate]; [(3-methylperfluorophenyl)(2-methylpentyl)(fluoromethyl) ammonium][tetraperfluorofluorenylborate]; [(octafluorobiphenyl)(hexyl)(2-methyl-5-propyl-heptyl) ammonium][tetrakis(hexafluoroindenyl)borate]; [(perfluorobiphenyl)(nonyl)(butyl)ammonium][tetrakis (hexafluorononyl)borate]; [(phenyl)(methyl)(fluoromethyl) ammonium][tetrabutylborate]; [(biphenyl) (hexafluorononyl)(propyl)ammonium] [tetrahextylaluminate]; [(3-perfluoromethyl-trifluorophenyl)(hexyl)(2-methylpentyl)ammonium] [tetrakis(perfluoropyrenyl)borate]; [(1-fluorophenyl) (perfluoroethyl)(nonyl)ammonium][tetrakis (perfluorobiphenyl)aluminate]; [(1-fluorobiphenyl)(hexyl) (perfluoroethyl)ammonium][tetrahextylborate]; [(perfluorophenyl)(2-methylpentyl)(ethyl)phosphonium] [tetrakis(perfluorohexylperfluorophenyl)aluminate]; [(tetrafluorophenyl)(hexafluorononyl)(ethyl)phosphonium] [tetrapentylborate]; [(2-perfluoromethyl-6-perfluoroethyl-perfluorobiphenyl)(hexyl)(2-methyl-5-propyl-heptyl) ammonium][tetrakis(perfluoropyrenyl)aluminate]; [(2-perfluoromethyl-6-perfluoroethyl-perfluorobiphenyl) (perfluoroethyl)(hexafluorononyl)phosphonium][tetrakis (methyloctafluorbiphenyl)aluminate]; [(phenyl)(dinonyl) ammonium][tetraperfluoroanthracenylborate]; [(3-perfluoroethyl-trifluorophenyl)(methyl)(butyl)ammonium] [tetrakis(hexafluorononyl)borate]; [N-(3-perfluoroethyl-trifluorophenyl)indolinium] [tetraperfluoroindenylaluminate]; [N-(octafluorobiphenyl) indolinium][tetraoctylborate]; [(3-perfluoromethyl-trifluorophenyl)(2-methyl-5-propyl-heptyl)(methyl) ammonium][tetrakis(perfluoromethylperfluoronaphthyl) aluminate]; [N-(3-perfluoroethyl-trifluorophenyl) phosphindolium][tetrakis(perfluorohexylperfluorophenyl) aluminate]; [(3-methyl-perfluorophenyl)(hexafluorononyl) (methyl)ammonium][tetraperfluorophenylaluminate]; [(2,4-difluorophenyl)(butyl)(ethyl)phosphonium] [tetraperfluorophenanthrylaluminate]; [(perfluorobiphenyl) (hexyl)(fluoromethyl)ammonium] [tetraperfluorophenylborate]; [(3-methyl-perfluorophenyl) (hexafluorononyl)(hexyl)ammonium]; [tetrakis(2-methyl-5-propyl-heptyl)aluminate]; [N-(2-perfluoromethyl-6-perfluoroethyl-perfluorobiphenyl)piperidinium][tetrakis (hexafluorononyl)aluminate]; [(2-methyl-6-perfluoromethyl-perfluorobiphenyl)(propyl) (perfluoroethyl)ammonium][tetrahextylborate]; [N-(2-perfluoromethyl-6-perfluoroethyl-perfluorobiphenyl) indolinium][tetraperfluorophenylborate]; [(3-methyl-perfluorophenyl)(ethyl)(hexyl)phosphonium][tetrakis (perfluoroethylperfluorobiphenyl)aluminate]; [(2,3- difluorophenyl)(ethyl)(butyl)phosphonium]
[tetraperfluoroanthracenylaluminate]; [N-(2-methyl-6-perfluoromethyl-perfluorobiphenyl)pyrrolonium]
[tetraperfluorophenylaluminate]; [N-(perfluorobiphenyl)
isoindolinium][tetrakis(hexafluorononyl)borate]; [(2,5-difluorophenyl)(dipropyl)ammonium][tetrakis
(methyloctafluorbiphenyl)aluminate]; [(2,3-difluorophenyl)
(ethyl)(hexafluorononyl)ammonium][tetrakis
(methyloctafluorbiphenyl)aluminate]; [(perfluorobiphenyl)
(hexafluorononyl)(propyl)ammonium][tetrakis
(perfluoropentylperfluorobiphenyl)aluminate];
[(octafluorobiphenyl)(2-methylpentyl)(2-methyl-5-propyl-heptyl)phosphonium][tetrakis(3-ethylheptyl)borate]; [(3-methyl-perfluorophenyl)(2-methylpentyl)(fluoromethyl)
ammonium][tetraperfluorofluorenylborate]; [(3-perfluoroethyl-trifluorophenyl)(butyl)(3-ethylheptyl)
ammonium][tetraperfluorophenanthrylborate]; [(3-perfluoroethyl-trifluorophenyl)(propyl)(methyl)
phosphonium][tetrakis(heptafluorofluorenyl)borate]; [N-(hexafluorobiphenyl)phosphindolium][tetrakis(2-methylpentyl)borate]; [(1-fluorophenyl)(hexyl)(methyl)
ammonium][tetrakis(2-methyl-5-propyl-heptyl)aluminate];
[N-(2,5-difluorophenyl)pyrrolium][tetrabutylborate];
[(biphenyl)(butyl)(fluoromethyl)ammonium][tetrakis
(perfluoropentylperfluorobiphenyl)aluminate]; [(2-methyl-6-perfluoromethyl-perfluorobiphenyl)(3-ethylheptyl)
(nonyl)ammonium][tetrakis(2-methyl-5-propyl-heptyl)
aluminate]; [(hexafluorobiphenyl)(fluoromethyl)(ethyl)
ammonium][tetrakis(methylperfluoronaphthyl)aluminate];
[(1-fluorophenyl)(3-ethylheptyl)(perfluoroethyl)
phosphonium][tetrakis(octafluorobiphenyl)borate]; [(1-fluorobiphenyl)(methyl)(butyl)phosphonium]
[tetrabutylborate]; [(2,5-difluorophenyl)(hexafluorononyl)
(perfluoroethyl)phosphonium][tetrabutylborate];
[(perfluorobiphenyl)(nonyl)(2-methylpentyl)ammonium]
[tetraperfluorophenanthrylborate]; [(2,3-difluorophenyl)
(dipropyl)ammonium][tetrakis(perfluoropyrenyl)borate];
[(2,3-difluorophenyl)(dihexyl)phosphonium][tetrakis
(perfluoropyrenyl)aluminate]; [(1-fluorophenyl)
(perfluoroethyl)(methyl)phosphonium][tetrakis
(perfluoropentylperfluorobiphenyl)borate]; [(phenyl)(hexyl)
(propyl)ammonium][tetrakis(pentafluoroindenyl)
aluminate]; [(phenyl)(hexyl)(butyl)ammonium][tetrakis
(perfluoromethylperfluoronaphthyl)borate]; [(phenyl)
(perfluoroethyl)(hexafluorononyl)phosphonium]
[tetraperfluorophenanthrylborate]; [(octafluorobiphenyl)
(ethyl)(3-ethylheptyl)ammonium][tetrakis
(hexafluoroindenyl)borate]; [(2,3-difluorophenyl)
(perfluoroethyl)(butyl)ammonium][tetrakis
(perfluoropyrenyl)borate]; [(phenyl)(2-methylpentyl)
(fluoromethyl)ammonium][tetrakis(perfluoropyrenyl)
aluminate]; [(2-methyl-6-perfluoromethyl-perfluorobiphenyl)(2-methylpentyl)(hexyl)ammonium]
[tetrakis(hexafluoroindenyl)borate]; [(3-methylperfluorophenyl)(3-ethylheptyl)(butyl)ammonium]
[tetraperfluorophenanthrylborate]; [(perfluorophenyl)(2-methylpentyl)(ethyl)ammonium][tetrapentylaluminate];
[(phenyl)(2-methyl-5-propyl-heptyl)(hexafluorononyl)
phosphonium][tetraperfluorophenylborate];
[(octafluorobiphenyl)(methyl)(ethyl)ammonium][tetrakis
(perfluoromethylperfluoronaphthyl)aluminate]; [(2,4-difluorophenyl)(3-ethylheptyl)(propyl)phosphonium]
[tetrakis(methyloctafluorbiphenyl)borate]; [(3-perfluoromethyl-trifluorophenyl)(2-methyl-5-propyl-heptyl)(hexafluorononyl)ammonium]
[tetraperfluorophenanthrylaluminate]; [(1-fluorophenyl)
(fluoromethyl)(ethyl)phosphonium]
[tetraperfluoroindenylborate]; [(2,3-difluorophenyl)(2-methylpentyl)(methyl)ammonium][tetraoctylaluminate];
[(biphenyl)(hexyl)(methyl)phosphonium][tetrakis
(perfluorohexylperfluorophenyl)borate]; [(perfluorophenyl)
(ethyl)(methyl)ammonium]
[tetraperfluorofluorenylaluminate]; [(1-fluorobiphenyl)
(perfluoroethyl)(2-methylpentyl)ammonium]
[tetrabutylborate]; [(octafluorobiphenyl)(2-methyl-5-propyl-heptyl)(hexafluorononyl)phosphonium]
[tetrapentylborate]; [(2,4-difluorophenyl)(dipropyl)
phosphonium][tetrapentylaluminate]; [(octafluorobiphenyl)
(propyl)(methyl)ammonium][tetrakis(pentafluoronaphthyl)
aluminate]; [(2-perfluoromethyl-6-perfluoroethyl-perfluorobiphenyl)(2-methyl-5-propyl-heptyl)
(perfluoroethyl)ammonium]
[tetraperfluorophenanthrylaluminate]; [(perfluorobiphenyl)
(butyl)(2-methylpentyl)ammonium][tetrakis
(octafluorobiphenyl)borate]; [(tetrafluorophenyl)(ethyl)
(fluoromethyl)ammonium][tetraoctylborate]; [N-(perfluorophenyl)pyrrolium][tetrakis(perfluorobiphenyl)
aluminate]; [(2,4-difluorophenyl)(hexafluorononyl)(methyl)
ammonium][tetrakis(3-ethylheptyl)aluminate]; [N-(2-perfluoromethyl-6-perfluoroethylperfluorobiphenyl)
isoindolinium][tetrakis(2-methylpentyl)borate]; [(2,4-difluorophenyl)(hexafluorononyl)(hexyl)ammonium]
[tetrakis(perfluorobiphenyl)aluminate]; [(1-fluorophenyl)
(ethyl)(hexyl)phosphonium][tetrakis
(methyloctafluorbiphenyl)aluminate]; [N-(perfluorophenyl)
pyrrolium][tetranonylborate]; [(1-fluorobiphenyl)(ethyl)(2-methyl-5-propyl-heptyl)ammonium][tetraheptylborate];
[(phenyl)(dinonyl)ammonium][tetrakis(perfluoropyrenyl)
aluminate]; [(biphenyl)(2-methylpentyl)(propyl)
phosphonium][tetrakis(ethylhexafluoronaphthyl)
aluminate]; [(3-perfluoroethyl-trifluorophenyl)(ethyl)
(propyl)ammonium][tetraperfluoroanthracenylaluminate];
[(2-perfluoromethyl-6-perfluoroethyl-perfluorobiphenyl)(3-ethylheptyl)(hexafluorononyl)ammonium]
[tetraoctylborate]; [(3-perfluoroethyl-trifluorophenyl)
(fluoromethyl)(hexafluorononyl)ammonium][tetrakis
(ethylhexafluoronaphthyl)borate]; [(2,5-difluorophenyl)(3-ethylheptyl)(2-methyl-5-propyl-heptyl)ammonium]
[tetraperfluorofluorenylborate]; [(3-perfluoromethyl-trifluorophenyl)(methyl)(3-ethylheptyl)ammonium][tetrakis
(perfluorohexylperfluorophenyl)aluminate]; [(biphenyl)
(fluoromethyl)(propyl)phosphonium][tetrakis
(hexafluoroindenyl)borate]; [(3-perfluoromethyl-trifluorophenyl)(ethyl)(methyl)ammonium]
[tetrahextylborate]; [(perfluorophenyl)(2-methyl-5-propyl-heptyl)(butyl)phosphonium][tetrabutylaluminate]; [(phenyl)
(pefluoroethyl)(nonyl)ammonium][tetrakis
(hexafluoronapthyl)aluminate]; [(3-perfluoromethyl-trifluorophenyl)(ethyl)(2-methyl-5-propyl-heptyl)
ammonium][tetrakis(perfluoronaphthyl)borate]; [(2-methyl-6-perfluoromethyl-perfluorobiphenyl)(perfluoroethyl)(3-ethylheptyl)ammonium][tetrakis(perfluoronaphthyl)
aluminate]; [(hexafluorobiphenyl)(perfluoroethyl)
(hexafluorononyl)phosphonium][tetrakis
(pentafluoronaphthyl)borate]; [(2,3-difluorophenyl)(propyl)
(ethyl)phosphonium][tetraheptylaluminate]; [(3-perfluoroethyltrifluorophenyl)(hexyl)(perfluoroethyl)
ammonium][tetrakis(pentafluoronaphthyl)borate];
[(biphenyl)(2-methylpentyl)(nonyl)phosphonium][tetrakis
(perfluorohexylperfluorophenyl)borate];
[(octafluorobiphenyl)(fluoromethyl)(nonyl)ammonium]
[tetrakis(methylperfluoronaphthyl)aluminate]; [(3-perfluoroethyl-trifluorophenyl)(perfluoroethyl)(2-methylpentyl)ammonium][tetrakis(perfluorobiphenyl)

borate]; [(2-methyl-6-perfluoromethyl-perfluorobiphenyl)(2-methyl-5-propyl-heptyl)(methyl)phosphonium][tetrakis(methyloctafluorbiphenyl)aluminate]; [(2-methyl-6-perfluoromethylperfluorobiphenyl)(ethyl)(2-methylpentyl)phosphonium][tetrakis(methylperfluoronaphthyl)aluminate]; [(3-perfluoromethyl-trifluorophenyl)(hexafluorononyl)(methyl)phosphonium][tetrahexylborate]; [(biphenyl)(butyl)(fluoromethyl)ammonium][tetrakis(perfluoropentylperfluorobiphenyl)aluminate]; [(2,5-difluorophenyl)(propyl)(hexyl)ammonium][tetrakis(pentafluoroindenyl)borate]; [(phenyl)(hexafluorononyl)(propyl)ammonium][tetrapentylborate]; [(hexafluorobiphenyl)(fluoromethyl)(butyl)phosphonium][tetrakis(octafluorobiphenyl)aluminate]; [(1-fluorobiphenyl)(methyl)(fluoromethyl)ammonium][tetrakis(pentafluoronaphthyl)borate]; [(phenyl)(2-methyl-5-propyl-heptyl)(nonyl)phosphonium][tetrakis(heptafluorofluorenyl)aluminate]; [(tetrafluorophenyl)(propyl)(ethyl)phosphonium][tetrapentylaluminate]; [(2,5-difluorophenyl)(3-ethylheptyl)(propyl)ammonium][tetrahextylaluminate]; [(tetrafluorophenyl)(ethyl)(perfluoroethyl)ammonium][tetrakis(hexafluoronapthyl)borate]; [(octafluorobiphenyl)(dibutyl)ammonium][tetrakis(perfluoronaphthyl)aluminate]; [(2,4-difluorophenyl)(nonyl)(methyl)ammonium][tetrakis(hexafluorononyl)aluminate]; [N-(3-perfluoromethyl-trifluorophenyl)piperidinium][tetrakis(methyloctafluorbiphenyl)aluminate]; [(perfluorophenyl)(fluoromethyl)(perfluoroethyl)ammonium][tetrakis(perfluoromethylperfluoronaphthyl)borate]; [(octafluorobiphenyl)(hexyl)(perfluoroethyl)ammonium][tetrakis(pentafluoronaphthyl)aluminate]; [(hexafluorobiphenyl)(dinonyl)ammonium][tetrabutylborate]; [(2,4-difluorophenyl)(2-methyl-5-propyl-heptyl)(butyl)ammonium][tetrapentylborate]; [(perfluorophenyl)(butyl)(hexafluorononyl)ammonium][tetrakis(heptafluorofluorenyl)borate]; [(octafluorobiphenyl)(2-methylpentyl)(fluoromethyl)ammonium][tetrakis(octafluorobiphenyl)borate]; [(hexafluorobiphenyl)(propyl)(ethyl)ammonium][tetrakis(3-ethylheptyl)aluminate]; [N-(hexafluorobiphenyl)phosphindolinium][tetrakis(2-methyl-5-propyl-heptyl)aluminate]; [(tetrafluorophenyl)(dipropyl)phosphonium][tetrakis(perfluoropentylperfluorobiphenyl)borate]; [(perfluorophenyl)(di2-methyl-5-propyl-heptyl)ammonium][tetrakis(perfluorobiphenyl)aluminate]; [(phenyl)(3-ethylheptyl)(2-methylpentyl)ammonium][tetrakis(perfluorobiphenyl)aluminate]; [N-(perfluorophenyl)phosphindolium][tetrakis(pentafluoroindenyl)aluminate]; [(3-methyl-perfluorophenyl)(2-methyl-5-propyl-heptyl)(fluoromethyl)ammonium][tetrakis(perfluoroethylperfluorobiphenyl)borate]; [(1-fluorophenyl)(difluoromethyl)ammonium][tetrakis(perfluoropyrenyl)borate]; [(phenyl)(2-methyl-5-propyl-heptyl)(nonyl)ammonium][tetraheptylborate]; [(3-perfluoroethyl-trifluorophenyl)(dimethyl)ammonium][tetrakis(perfluoromethylperfluoronaphthyl)borate]; [(2,4-difluorophenyl)(2-methyl-5-propyl-heptyl)(butyl)ammonium][tetrakis(2-methyl-5-propyl-heptyl)aluminate]; [(perfluorobiphenyl)(nonyl)(hexyl)ammonium][tetraperfluorofluorenylaluminate]; [(biphenyl)(methyl)(hexafluorononyl)ammonium][tetrakis(hexafluorononyl)aluminate]; [(3-methyl-perfluorophenyl)(dipropyl)ammonium][tetrakis(perfluorobiphenyl)borate]; [(1-fluorobiphenyl)(3-ethylheptyl)(nonyl)ammonium][tetrakis(perfluoromethylperfluoronaphthyl)aluminate]; [(1-fluorobiphenyl)(3-ethylheptyl)(ethyl)ammonium][tetraperfluorofluorenylborate]; [N-(2,5-difluorophenyl)pyrrolonium][tetrakis(perfluoropyrenyl)borate]; [(perfluorophenyl)(perfluoroethyl)(hexafluorononyl)phosphonium][tetrakis(perfluoropyrenyl)aluminate]; [(1-fluorobiphenyl)(ethyl)(nonyl)phosphonium][tetrakis(perfluoronaphthyl)borate]; [(3-perfluoroethyl-trifluorophenyl)(nonyl)(propyl)ammonium][tetrapentylborate]; [(3-perfluoromethyl-trifluorophenyl)(2-methylpentyl)(3-ethylheptyl)ammonium][tetrakis(3-ethylheptyl)aluminate]; [(3-perfluoromethyl-trifluorophenyl)(2-methyl-5-propyl-heptyl)(nonyl)phosphonium][tetraperfluoroindenylaluminate]; [(biphenyl)(2-methyl-5-propyl-heptyl)(propyl)phosphonium][tetraoctylborate]; [N-(2,4-difluorophenyl)phosphindolinium][tetrakis(hexafluoroindenyl)aluminate]; [(2-perfluoromethyl-6-perfluoroethyl-perfluorobiphenyl)(methyl)(butyl)ammonium][tetrakis(perfluoropyrenyl)borate]; [(3-perfluoroethyl-trifluorophenyl)(ethyl)(3-ethylheptyl)ammonium][tetrakis(3-ethylheptyl)borate]; [(1-fluorobiphenyl)(perfluoroethyl)(methyl)phosphonium][tetranonylaluminate]; [(1-fluorophenyl)(fluoromethyl)(perfluoroethyl)phosphonium][tetrakis(3-ethylheptyl)aluminate]; [(perfluorophenyl)(nonyl)(2-methylpentyl)ammonium][tetrakis(perfluoromethylperfluoronaphthyl)borate]; [(biphenyl)(propyl)(2-methyl-5-propyl-heptyl)phosphonium][tetraheptylborate]; [N-(phenyl)phosphindolium][tetrakis(heptafluorofluorenyl)aluminate]; [(3-perfluoromethyl-trifluorophenyl)(propyl)(hexafluorononyl)ammonium][tetrakis(hexafluoroindenyl)aluminate]; [(tetrafluorophenyl)(perfluoroethyl)(ethyl)ammonium][tetrakis(perfluorobiphenyl)aluminate]; [(perfluorophenyl)(2-methylpentyl)(nonyl)ammonium][tetrakis(heptafluorofluorenyl)borate]; [(octafluorobiphenyl)(fluoromethyl)(propyl)ammonium][tetraperfluoroanthracenylborate]; [(octafluorobiphenyl)(2-methylpentyl)(propyl)phosphonium][tetrakis(2-methylpentyl)aluminate]; [N-(2,3-difluorophenyl)pyrrolium][tetraoctylaluminate]; [(biphenyl)(ethyl)(nonyl)ammonium][tetrakis(octafluorobiphenyl)borate]; [(1-fluorobiphenyl)(2-methyl-5-propyl-heptyl)(fluoromethyl)phosphonium][tetraperfluoroindenylborate]; [(3-perfluoromethyl-trifluorophenyl)(propyl)(3-ethylheptyl)ammonium][tetraoctylborate]; [(hexafluorobiphenyl)(2-methyl-5-propyl-heptyl)(3-ethylheptyl)ammonium][tetrakis(pentafluoroindenyl)borate]; [(2,3-difluorophenyl)(hexafluorononyl)(ethyl)ammonium][tetraperfluorophenanthrylaluminate]; [(2,4-difluorophenyl)(3-ethylheptyl)(butyl)phosphonium][tetraperfluoroindenylborate]; [(phenyl)(2-methyl-5-propyl-heptyl)(hexyl)ammonium][tetrakis(hexafluorononyl)aluminate]; [(3-perfluoroethyl-trifluorophenyl)(hexafluorononyl)(propyl)ammonium][tetrakis(ethylhexafluoronaphthyl)borate]; [(1-fluorobiphenyl)(2-methyl-5-propyl-heptyl)(ethyl)ammonium][tetrakis(2-methylpentyl)borate]; [(perfluorobiphenyl)(3-ethylheptyl)(propyl)ammonium][tetraperfluoroindenylborate]; [(perfluorophenyl)(propyl)(perfluoroethyl)ammonium][tetrakis(3-ethylheptyl)aluminate]; [(2-methyl-6-perfluoromethyl-perfluorobiphenyl)(dipropyl)ammonium][tetraheptylaluminate]; [(2-perfluoromethyl-6-perfluoroethyl-perfluorobiphenyl)(hexyl)(nonyl)ammonium][tetrakis(2-methylpentyl)aluminate]; [(1-fluorobiphenyl)(2-methyl-5-propyl-heptyl)(ethyl)ammonium][tetrakis(perfluorohexylperfluorophenyl)aluminate]; [(2,4-difluorophenyl)(ethyl)(propyl)ammonium][tetrakis(heptafluorofluorenyl)borate]; [(3-perfluoromethyl-trifluorophenyl)(nonyl)(ethyl)ammonium][tetrahextylborate]; [(1-fluorobiphenyl)(perfluoroethyl)

(hexafluorononyl)ammonium][tetraoctylaluminate]; [(2,3-difluorophenyl)(butyl)(fluoromethyl)ammonium][tetrakis(2-methylpentyl)borate]; [(2-perfluoromethyl-6-perfluoroethyl-perfluorobiphenyl)(perfluoroethyl)(hexyl)ammonium][tetraperfluorophenylaluminate]; [(2,3-difluorophenyl)(hexafluorononyl)(butyl)ammonium][tetrabutylborate]; [(hexafluorobiphenyl)(ethyl)(2-methyl-5-propyl-heptyl)ammonium][tetrabutylaluminate]; [(2,3-difluorophenyl)(3-ethylheptyl)(hexyl)phosphonium][tetrakis(perfluoropentylperfluorobiphenyl)aluminate]; [(3-perfluoroethyl-trifluorophenyl)(hexafluorononyl)(propyl)ammonium][tetrakis(hexafluoronapthyl)borate]; [N-(perfluorophenyl)piperidinium][tetraoctylborate]; [(perfluorophenyl)(2-methylpentyl)(ethyl)ammonium][tetrakis(octafluorobiphenyl)borate]; [(3-perfluoroethyl-trifluorophenyl)(butyl)(2-methylpentyl)phosphonium][tetrakis(methyloctafluorbiphenyl)aluminate]; [(2,4-difluorophenyl)(2-methyl-5-propyl-heptyl)(propyl)ammonium][tetrakis(perfluoropyrenyl)aluminate]; [(2,3-difluorophenyl)(ethyl)(3-ethylheptyl)ammonium][tetrakis(hexafluoroindenyl)aluminate]; [(perfluorophenyl)(di2-methyl-5-propyl-heptyl)ammonium][tetrakis(hexafluoronapthyl)aluminate]; [(3-methyl-perfluorophenyl)(di3-ethylheptyl)ammonium][tetrakis(hexafluorononyl)aluminate]; [N-(perfluorophenyl)indolium][tetrakis(hexafluorononyl)aluminate]; [(octafluorobiphenyl)(hexafluorononyl)(3-ethylheptyl)phosphonium][tetrakis(3-ethylheptyl)borate]; [(perfluorophenyl)(diethyl)phosphonium][tetranonylborate]; [N-(1-fluorobiphenyl)pyrrolonium][tetrakis(perfluoronaphthyl)borate]; [(2,4-difluorophenyl)(3-ethylheptyl)(2-methyl-5-propyl-heptyl)ammonium][tetrakis(perfluorohexylperfluorophenyl)borate]; [(hexafluorobiphenyl)(methyl)(fluoromethyl)ammonium][tetrakis(hexafluoroindenyl)aluminate]; [(2,5-difluorophenyl)(fluoromethyl)(2-methyl-5-propyl-heptyl)phosphonium][tetranonylborate]; [(2-perfluoromethyl-6-perfluoroethylperfluorobiphenyl)hexyl)(2-methylpentyl)ammonium][tetraoctylaluminate]; [(perfluorophenyl)(3-ethylheptyl)(fluoromethyl)phosphonium][tetranonylborate]; [(tetrafluorophenyl)(ethyl)(hexyl)ammonium][tetraperfluorophenylborate]; [(2,3-difluorophenyl)(difluoromethyl)ammonium][tetrakis(pentafluoronaphthyl)borate]; [(1-fluorophenyl)(propyl)(hexyl)ammonium][tetrakis(perfluoropentylperfluorobiphenyl)borate]; [(3-perfluoroethyl-trifluorophenyl)(2-methyl-5-propyl-heptyl)(hexafluorononyl)phosphonium][tetrakis(octafluorobiphenyl)aluminate]; [(2-perfluoromethyl-6-perfluoroethylperfluorobiphenyl)(fluoromethyl)(perfluoroethyl)ammonium][tetrakis(pentafluoronaphthyl)aluminate]; [(3-methyl-perfluorophenyl)(hexafluorononyl)(perfluoroethyl)phosphonium][tetraperfluoroindenylaluminate]; [(2,4-difluorophenyl)(propyl)(butyl)ammonium][tetrakis(pentafluoroindenyl)aluminate]; [N-(3-perfluoroethyl-trifluorophenyl)pyrrolidinium][tetraoctylaluminate]; [(2-methyl-6-perfluoromethylperfluorobiphenyl)(dihexyl)phosphonium][tetrakis(perfluoromethylperfluoronaphthyl)borate]; [(3-perfluoromethyl-trifluorophenyl)(2-methyl-5-propyl-heptyl)(butyl)phosphonium][tetrakis(perfluoropentylperfluorobiphenyl)borate]; [(2-perfluoromethyl-6-perfluoroethyl-perfluorobiphenyl)(ethyl)(hexafluorononyl)phosphonium][tetraperfluoroanthracenylaluminate]; [(1-fluorophenyl)(difluoromethyl)ammonium][tetraperfluoroindenylaluminate]; [(biphenyl)(3-ethylheptyl)(fluoromethyl)ammonium][tetrakis(perfluoropentylperfluorobiphenyl)borate]; [(phenyl)(methyl)(perfluoroethyl)ammonium][tetraperfluorophenanthrylborate]; [(2,5-difluorophenyl)(hexyl)(nonyl)phosphonium][tetrakis(methyloctafluorbiphenyl)aluminate]; [N-(1-fluorobiphenyl)pyrrolium][tetraoctylborate]; [(perfluorophenyl)(hexyl)(propyl)ammonium][tetraheptylaluminate]; [(biphenyl)(hexyl)(2-methyl-5-propyl-heptyl)ammonium][tetraoctylaluminate]; [(2,5-difluorophenyl)(perfluoroethyl)(2-methylpentyl)phosphonium][tetrakis(2-methyl-5-propyl-heptyl)aluminate]; [(3-methyl-perfluorophenyl)(2-methylpentyl)(methyl)ammonium][tetrakis(perfluoroethylperfluorobiphenyl)aluminate]; [(biphenyl)(methyl)(nonyl)ammonium][tetrakis(perfluoronaphthyl)aluminate]; [(octafluorobiphenyl)(methyl)(hexafluorononyl)ammonium][tetraoctylaluminate]; [(tetrafluorophenyl)(nonyl)(butyl)ammonium][tetrakis(methylperfluoronaphthyl)aluminate]; [(perfluorophenyl)(hexyl)(nonyl)ammonium][tetrakis(2-methylpentyl)borate]; [(3-perfluoromethyl-trifluorophenyl)(2-methyl-5-propyl-heptyl)(butyl)phosphonium][tetraoctylborate]; [(2-methyl-6-perfluoromethylperfluorobiphenyl)(2-methylpentyl)(propyl)phosphonium][tetrakis(perfluoromethylperfluoronaphthyl)borate]; [(biphenyl)(2-methyl-5-propyl-heptyl)(2-methylpentyl)ammonium][tetrakis(perfluoronaphthyl)aluminate]; [(2,5-difluorophenyl)(dimethyl)ammonium][tetrakis(perfluoropyrenyl)aluminate]; [(2-perfluoromethyl-6-perfluoroethyl-perfluorobiphenyl)(perfluoroethyl)(ethyl)phosphonium][tetrakis(2-methyl-5-propyl-heptyl)aluminate]; [(2-perfluoromethyl-6-perfluoroethyl-perfluorobiphenyl)(methyl)(2-methyl-5-propyl-heptyl)ammonium][tetrakis(hexafluorononyl)borate]; [N-(octafluorobiphenyl)pyrrolonium][tetrahextylaluminate]; [N-(biphenyl)pyrrolidinium][tetrakis(perfluoroethylperfluorobiphenyl)aluminate]; [(1-fluorophenyl)(methyl)(ethyl)phosphonium][tetraoctylaluminate]; [(2,3-difluorophenyl)(propyl)(hexyl)phosphonium][tetrakis(pentafluoroindenyl)aluminate]; [N-(1-fluorobiphenyl)isoindolinium][tetrakis(perfluoromethylperfluoronaphthyl)borate]; [(perfluorobiphenyl)(ethyl)(butyl)ammonium][tetrabutylborate]; [(perfluorobiphenyl)(2-methylpentyl)(nonyl)phosphonium][tetrakis(methyloctafluorbiphenyl)aluminate]; [(3-methyl-perfluorophenyl)(dinonyl)ammonium][tetrakis(methylperfluoronaphthyl)aluminate]; [(1-fluorobiphenyl)(hexafluorononyl)(perfluoroethyl)ammonium][tetraoctylaluminate]; [(hexafluorobiphenyl)(ethyl)(2-methyl-5-propyl-heptyl)ammonium][tetraperfluorophenanthrylborate]; [(perfluorophenyl)(3-ethylheptyl)(nonyl)ammonium][tetraperfluoroanthracenylaluminate]; [N-(2,5-difluorophenyl)indolinium][tetrakis(methylperfluoronaphthyl)aluminate]; [(hexafluorobiphenyl)(3-ethylheptyl)(hexyl)phosphonium][tetrapentylaluminate]; [(3-perfluoroethyl-trifluorophenyl)(2-methyl-5-propyl-heptyl)(methyl)phosphonium][tetrakis(pentafluoroindenyl)borate]; [(phenyl)(ethyl)(2-methyl-5-propyl-heptyl)phosphonium][tetrakis(2-methyl-5-propyl-heptyl)borate]; [(perfluorophenyl)(perfluoroethyl)(fluoromethyl)ammonium][tetrakis(pentafluoroindenyl)aluminate]; [(2-methyl-6-perfluoromethyl-perfluorobiphenyl)(fluoromethyl)(2-methylpentyl)ammonium][tetraperfluorophenanthrylborate]; [(hexafluorobiphenyl)(dihexafluorononyl)ammonium][tetrakis(perfluoromethylperfluoronaphthyl)aluminate]; [N-

(2-perfluoromethyl-6-perfluoroethyl-perfluorobiphenyl) pyrrolium][tetraperfluorophenanthrylaluminate]; [(2,5-difluorophenyl)(perfluoroethyl)(fluoromethyl)ammonium] [tetrakis(methyloctafluorbiphenyl)borate]; [(2,4-difluorophenyl)(perfluoroethyl)(ethyl)phosphonium] [tetraperfluorofluorenylborate]; [(tetrafluorophenyl) (hexafluorononyl)(butyl)phosphonium] [tetraperfluorophenanthrylaluminate]; [(tetrafluorophenyl) (2-methylpentyl)(hexyl)ammonium][tetrakis(3-ethylheptyl) borate]; [(biphenyl)(nonyl)(propyl)ammonium][tetrakis (pentafluoronaphthyl)borate]; [(3-perfluoromethyl-trifluorophenyl)(3-ethylheptyl)(2-methylpentyl) ammonium][tetrapentylborate]; [(tetrafluorophenyl)(3-ethylheptyl)(2-methyl-5-propyl-heptyl)ammonium][tetrakis (perfluoromethylperfluoronaphthyl)borate]; [(2-methyl-6-perfluoromethyl-perfluorobiphenyl)(methyl)(hexyl) ammonium][tetrakis(perfluorobiphenyl)borate]; [(tetrafluorophenyl)(hexyl)(fluoromethyl)phosphonium] [tetraperfluoroindenylborate]; [N-(2-perfluoromethyl-6-perfluoroethyl-perfluorobiphenyl)phosphapyrrolidinium] [tetrakis(3-ethylheptyl)borate]; [(phenyl)(ethyl)(2-methylpentyl)phosphonium] [tetraperfluorofluorenylaluminate]; [(phenyl) (perfluoroethyl)(methyl)ammonium][tetrakis(2-methyl-5-propyl-heptyl)borate]; [N-(3-perfluoromethyl-trifluorophenyl)phosphindolinium][tetrakis(2-methyl-5-propyl-heptyl)borate]; [(2,3-difluorophenyl)(di2-methylpentyl)ammonium][tetrakis (ethylhexafluoronaphthyl)borate]; [(2,3-difluorophenyl) (fluoromethyl)(butyl)ammonium][tetrakis (perfluorobiphenyl)aluminate]; [(2,5-difluorophenyl)(3-ethylheptyl)(hexyl)ammonium]; [tetrakis (perfluorobiphenyl)aluminate]; [(hexafluorobiphenyl) (hexyl)(nonyl)phosphonium] [tetraperfluoroanthracenylaluminate]; [(2-perfluoromethyl-6-perfluoroethyl-perfluorobiphenyl)(perfluoroethyl) (propyl)ammonium][tetrakis(ethylhexafluoronaphthyl) borate]; [(3-methyl-perfluorophenyl)(propyl)(fluoromethyl) ammonium][tetrakis(methyloctafluorbiphenyl)borate]; [(2-methyl-6-perfluoromethylperfluorobiphenyl) (hexafluorononyl)(3-ethylheptyl)ammonium] [tetrabutylaluminate]; [(1-fluorobiphenyl)(3-ethylheptyl) (hexafluorononyl)phosphonium][tetrabutylborate]; [(2,4-difluorophenyl)(butyl)(3-ethylheptyl)phosphonium] [tetranonylborate]; [(2,4-difluorophenyl)(diperfluoroethyl) phosphonium][tetrakis(pentafluoroindenyl)borate]; [(1-fluorobiphenyl)(nonyl)(2-methylpentyl)ammonium] [tetrakis(pentafluoronaphthyl)aluminate]; [(perfluorophenyl)(fluoromethyl)(perfluoroethyl) ammonium][tetrakis(ethylhexafluoronaphthyl)borate]; [(1-fluorobiphenyl)(fluoromethyl)(2-methylpentyl) phosphonium][tetrakis(pentafluoroindenyl)aluminate]; [(perfluorophenyl)(propyl)(2-methyl-5-propyl-heptyl) ammonium][tetrakis(pentafluoroindenyl)aluminate]; [(2,3-difluorophenyl)(2-methyl-5-propyl-heptyl)(ethyl) ammonium][tetraperfluorophenylaluminate]; [(2,5-difluorophenyl)(fluoromethyl)(ethyl)ammonium][tetrakis (perfluoroethylperfluorobiphenyl)borate]; [(3-perfluoroethyl-trifluorophenyl)(nonyl)(2-methylpentyl) phosphonium][tetrakis(hexafluoroindenyl)borate]; [N-(1-fluorophenyl)pyrrolonium][tetraoctylaluminate]; [(1-fluorophenyl)(nonyl)(perfluoroethyl)phosphonium][tetrakis (perfluoromethylperfluoronaphthyl)aluminate]; [(3-perfluoroethyl-trifluorophenyl)(fluoromethyl)(ethyl) ammonium][tetrakis(perfluoropentylperfluorobiphenyl) aluminate]; [(perfluorobiphenyl)(hexafluorononyl) (perfluoroethyl)ammonium]

[tetraperfluoroanthracenylborate]; [(hexafluorobiphenyl) (propyl)(fluoromethyl)ammonium][tetrakis (pentafluoroindenyl)aluminate]; [(1-fluorophenyl) (dihexafluorononyl)ammonium][tetrakis (pentafluoronaphthyl)aluminate]; [(3-perfluoromethyl-trifluorophenyl)(3-ethylheptyl)(2-methylpentyl) ammonium][tetrakis(perfluorobiphenyl)aluminate]; [(2,3-difluorophenyl)(fluoromethyl)(2-methyl-5-propyl-heptyl) ammonium][tetrakis(perfluoronaphthyl)borate]; [(1-fluorophenyl)(2-methylpentyl)(propyl)phosphonium] [tetraperfluorofluorenylborate]; [(1-fluorobiphenyl)(2-methyl-5-propyl-heptyl)(ethyl)ammonium] [tetraperfluorofluorenylborate]; [(1-fluorobiphenyl)(hexyl) (ethyl)phosphonium][tetraperfluorofluorenylborate]; [(perfluorophenyl)(propyl)(nonyl)ammonium][tetrakis (perfluorobiphenyl)aluminate]; [(1-fluorophenyl)(nonyl) (hexafluorononyl)phosphonium] [tetraperfluorofluorenylaluminate]; [(1-fluorophenyl) (hexafluorononyl)ammonium][tetrakis (heptafluorofluorenyl)alumorate]; [(penfluorobiphenyl) (butyl)(perfluoroethyl)ammonium][tetrakis (pentafluoronaphthyl)borate]; [(2,5-difluorophenyl)(2-methyl-5-propyl-heptyl)(2-methylpentyl)phosphonium] [tetraperfluoroanthracenylaluminate]; [(2-methyl-6-perfluoromethyl-perfluorobiphenyl)(hexafluorononyl) (butyl)ammonium][tetraoctylaluminate]; [(3-perfluoroethyl-trifluorophenyl)(ethyl)(hexafluorononyl) ammonium][tetrakis(pentafluoronaphthyl)aluminate]; [(1-fluorophenyl)(methyl)(hexyl)phosphonium] [tetraperfluoroindenylaluminate]; [(1-fluorobiphenyl) (nonyl)(2-methyl-5-propyl-heptyl)phosphonium][tetrakis (heptafluorofluorenyl)borate]; [(3-perfluoromethyl-trifluorophenyl)(ethyl)(3-ethylheptyl)ammonium] [tetraheptylborate]; [(perfluorophenyl)(propyl)(hexyl) phosphonium][tetrakis(pentafluoronaphthyl)borate]; [(3-methyl-perfluorophenyl)(2-methylpentyl)(fluoromethyl) ammonium][tetrakis(perfluoroethylperfluorobiphenyl) aluminate]; [(octafluorobiphenyl)(3-ethylheptyl) (perfluoroethyl)phosphonium][tetrakis (perfluoroethylperfluorobiphenyl)borate]; [(2-perfluoromethyl-6-perfluoroethyl-perfluorobiphenyl) (nonyl)(propyl)phosphonium][tetrakis (perfluoroethylperfluorobiphenyl)borate]; [N-(1-fluorobiphenyl)pyrrolium][tetranonylborate]; [(hexafluorobiphenyl)(hexafluorononyl)(nonyl) phosphonium][tetraheptylborate]; [(hexafluorobiphenyl) (di2-methylpentyl)phosphonium] [tetraperfluorophenylaluminate]; [(phenyl)(difluoromethyl) phosphonium][tetrakis(perfluoromethylperfluoronaphthyl) borate]; [(3-methyl-perfluorophenyl)(3-ethylheptyl) (methyl)ammonium][tetraheptylborate]; [(perfluorobiphenyl)(fluoromethyl)(hexafluorononyl) ammonium][tetrapentylborate]; [(3-perfluoroethyltrifluorophenyl)(3-ethylheptyl)(methyl) ammonium][tetrakis(perfluoronaphthyl)borate]; [N-(perfluorobiphenyl)pyrrolidinium] [tetraperfluorofluorenylborate]; [(octafluorobiphenyl) (butyl)(ethyl)ammonium][tetrabutylborate]; [(3-methyl-perfluorophenyl)(butyl)(methyl)ammonium] [tetrapentylborate]; [(3-perfluoromethyl-trifluorophenyl) (ethyl)(methyl)ammonium][tetrakis(2-methyl-5-propyl-heptyl)borate]; [(2,5-difluorophenyl)(nonyl)(ethyl) ammonium][tetrakis(methyloctafluorbiphenyl)aluminate]; [(2-methyl-6-perfluoromethylperfluorobiphenyl) (hexafluorononyl)(fluoromethyl)ammonium] [tetraperfluorophenylaluminate]; [(2-methyl-6-perfluoromethyl-perfluorobiphenyl)(dibutyl)ammonium]

[tetrakis(perfluoroethylperfluorobiphenyl)borate]; [(3-perfluoromethyl-trifluorophenyl)(dihexyl)ammonium][tetrapentylaluminate]; [N-(2,3-difluorophenyl)phosphindolium][tetrakis(hexafluoroindenyl)aluminate]; [(phenyl)(3-ethylheptyl)(nonyl)phosphonium][tetraperfluorofluorenylborate]; [(1-fluorophenyl)(fluoromethyl)(hexafluorononyl)ammonium][tetrabutylaluminate]; [(3-perfluoroethyl-trifluorophenyl)(fluoromethyl)(nonyl)ammonium][tetrakis(perfluoronaphthyl)borate]; [(3-perfluoromethyl-trifluorophenyl)(fluoromethyl)(methyl)phosphonium][tetraheptylaluminate]; [(3-perfluoromethyltrifluorophenyl)(ethyl)(3-ethylheptyl)phosphonium][tetrakis(2-methyl-5-propyl-heptyl)borate]; [(2,3-difluorophenyl)(ethyl)(2-methylpentyl)ammonium][tetrakis(2-methyl-5-propyl-heptyl)aluminate]; [(2,4-difluorophenyl)(2-methyl-5-propyl-heptyl)(propyl)ammonium][tetrakis(methyloctafluorbiphenyl)borate]; [(1-fluorobiphenyl)(methyl)(butyl)ammonium][tetrakis(perfluorobiphenyl)aluminate]; [(biphenyl)(3-ethylheptyl)(hexyl)ammonium][tetraperfluorofluorenylaluminate]; [(1-fluorophenyl)(ethyl)(propyl)phosphonium][tetraoctylaluminate]; [(phenyl)(dinonyl)ammonium][tetrakis(3ethylheptyl)borate]; [(perfluorobiphenyl)(ethyl)(2-methyl-5-propyl-heptyl)phosphonium][tetrakis(perfluoropentylperfluorobiphenyl)borate]; [(biphenyl)(methyl)(hexafluorononyl)ammonium][tetrakis(2-methyl-5-propyl-heptyl)aluminate]; [(phenyl)(butyl)(2-methyl-5-propyl-heptyl)ammonium][tetrakis(perfluorohexylperfluorophenyl)borate]; [(biphenyl)(hexafluorononyl)(hexyl)phosphonium][tetraperfluoroindenylborate]; [(tetrafluorophenyl)(2-methyl-5-propyl-heptyl)(nonyl)phosphonium][tetraperfluoroindenylaluminate]; [(hexafluorobiphenyl)(perfluoroethyl)(nonyl)phosphonium][tetrakis(perfluoroethylperfluorobiphenyl)aluminate]; [(2,3-difluorophenyl)(dibutyl)ammonium][tetrakis(perfluoropyrenyl)borate]; [N-(1-fluorophenyl)pyrrolonium][tetrakis(perfluorobiphenyl)borate]; [(biphenyl)(hexafluorononyl)(hexyl)phosphonium][tetrakis(methyloctafluorbiphenyl)aluminate]; [N-(tetrafluorophenyl)pyrrolium][tetraperfluoroanthracenylborate]; [(2,3-difluorophenyl)(propyl)(hexyl)ammonium][tetrakis(pentafluoroindenyl)aluminate]; [N-(2-perfluoromethyl-6-perfluoroethyl-perfluorobiphenyl)pyrrolonium][tetranonylborate]; [(2,4-difluorophenyl)(butyl)(nonyl)phosphonium][tetraperfluoroanthracenylborate]; [(perfluorobiphenyl)(butyl)(methyl)ammonium][tetranonylborate]; [(tetrafluorophenyl)(hexyl)(methyl)ammonium][tetraoctylborate]; [(1-fluorophenyl)(2-methylpentyl)(perfluoroethyl)ammonium][tetraoctylaluminate]; [(1-fluorobiphenyl)(2-methyl-5-propyl-heptyl)(ethyl)ammonium][tetraheptylborate]; [(2-perfluoromethyl-6-perfluoroethyl-perfluorobiphenyl)(di3-ethylheptyl)ammonium][tetrakis(perfluorobiphenyl)aluminate]; [(2,5-difluorophenyl)(3-ethylheptyl)(hexyl)ammonium][tetrakis(hexafluorononyl)aluminate]; [(1-fluorobiphenyl)(butyl)(methyl)phosphonium][tetrakis(perfluoroethylperfluorobiphenyl)borate]; [(biphenyl)(hexafluorononyl)(butyl)ammonium][tetrakis(heptafluorofluorenyl)borate]; [(perfluorophenyl)(2-methyl-5-propyl-heptyl)(ethyl)ammonium][tetraheptylaluminate]; [(2,5-difluorophenyl)(fluoromethyl)(hexafluorononyl)ammonium][tetrakis(methylperfluoronaphthyl)aluminate]; [(octafluorobiphenyl)(butyl)(2-methylpentyl)ammonium][tetrakis(3-ethylheptyl)borate]; [(2-perfluoromethyl-6-perfluoroethyl-perfluorobiphenyl)(butyl)(fluoromethyl)phosphonium][tetrakis(perfluorobiphenyl)borate]; [(3-perfluoroethyl-trifluorophenyl)(2-methyl-5-propyl-heptyl)(hexyl)phosphonium][tetrakis(2-methyl-5-propyl-heptyl)borate]; [(2,5-difluorophenyl)(hexafluorononyl)(hexyl)ammonium][tetrakis(pentafluoronaphthyl)borate]; [(octafluorobiphenyl)(dibutyl)ammonium][tetrakis(perfluorohexylperfluorophenyl)borate]; [(hexafluorobiphenyl)(hexyl)(nonyl)phosphonium][tetrakis(2-methylpentyl)borate]; [(1-fluorophenyl)(methyl)(hexafluorononyl)phosphonium][tetrakis(perfluoropyrenyl)aluminate].

The following examples illustrate the foregoing discussion. All parts, proportions and percentages are by weight unless otherwise indicated. All examples were carried out in dry, oxygen-free environments and solvents. Although the examples cover certain embodiments of the present invention, they do not limit the invention in any specific respect.

EXAMPLES

All molecular weights are weight average molecular weight unless otherwise noted. Weight average molecular weight (Mw) and number average molecular weight (Mn) were measured by Gel Permeation Chromatography, unless otherwise noted, using a Waters 150 Gel Permeation Chromatograph equipped with differential refractive index (DRI) and low angle light scattering (LS) detectors and calibrated using polystyrene standards. Samples were run in 1,2,4-trichlorobenzene (135° C) using three Polymer Laboratories, PC Gel, mixed B columns in series. This general technique is discussed in "Liquid Chromatography of Polymers and Related Materials III" J. Cazes current regime Ed., Marcel Decker, 1981, page 207, which is incorporated by reference for purposes of U.S. patent practice. No corrections for column spreading were employed; however, data on generally accepted standards, e.g. National Bureau of Standards Polyethylene 1475, demonstrated a precision with 0.2 units for Mw/Mn that was calculated from elution times.

Example 1

Synthesis of $C_6F_5$—$N(CH_2CH_2)_2$: To a solution of hexafluorobenzene (30 g) in 100 ml dimethylsulfoxide was added pyrrolidine (10.9 g). The reaction was heated and stirred for 1 h. After quenching the reaction by pouring it into an aqueous solution of sodium bicarbonate, the product was extracted with chloroform (100 ml). The organic layer was separated and dried over magnesium sulfate. The magnesium sulfate was removed by filtration and the solvent was removed under reduced pressure. This left an orange oil. The clear, colorless liquid product was obtained by distillation (55–60° C.) at $10^{-3}$ torr: yield=19.19 g, 53%. $^1$H NMR (DMSO-$d_6$, 25° C.): δ3.44 (m, 4H), 1.85 (m, 4H). $^{19}$F NMR (CDCl$_3$, 25° C.): δ−155.4 (m, 2F), −165.5(t, 1F), −172.1 (m, 2F).

Example 2

Synthesis of $C_6F_5$—$N(CH_2CH_2)_2$.HCl: To a pentane (100 ml) solution of $C_6F_5$—$N(CH_2CH_2)_2$ (1.55 g) was added anhydrous HCl. The HCl was prepared in situ by adding concentrated sulfuric acid to sodium chloride and transferring the gas via cannula. The product precipitated immediately upon addition of the HCl. Once the addition of the HCl was completed, the suspension was placed back into the glovebox to collect the product by filtration. The product was dried under reduced pressure: yield=1.48 g, 82%. $^1$H NMR (CDCl$_3$, 25° C.): δ12.9 (s, 1H), 3.71 (m, 4H), 2.17 (m, 4H).

Example 3

Synthesis of [C$_6$F$_5$—N(CH$_2$CH$_2$)$_2$(H)][(C$_6$F$_5$)$_4$B]: A methylene chloride (100 ml) solution of [Li(diethyl ether)$_2$][(C$_6$F$_5$)$_4$B] (1.52 g) was treated with a methylene chloride solution of C$_6$F$_5$—N(CH$_2$CH$_2$)$_2$.HCl (0.5 g). A white precipitate formed immediately upon adding the ammonium salt. After the reactions were stirred for 1 h, the LiCl byproduct was removed by filtration. The filtrate volume was reduced by approximately 80%. Approximately 10 ml of pentane was added to the filtrate, and the mixture chilled for 15 h. The product was collected by filtration and washed with pentane. This left a white crystalline product: yield =1.480 g. $^1$H NMR (CD$_2$Cl$_2$, 25° C.): δ7.95 (bs, 1H), 4.32 (bt, 2H), 3.94 (bt, 2H), 2.68 (bt, 2H), 2.43 (bt, 2H), $^{19}$F NMR (CD$_2$Cl$_2$, 25° C.): 67 –133.8 (m, 8F), –145.2 (m, 1F), –145.5 (m, 2F), –155.3 (m, 2F), –163.9 (t, 4F), –168.0 (m, 8F).

Batch Polymerization Reactions

Propylene polymerization reactions were carried out in a well-stirred 0.5 L batch reactor equipped to perform coordination polymerization in the presence of an inert hydrocarbon solvent (hexanes) at pressures up to 500 psig and temperatures up to 150° C. In the vapor-liquid polymerization system, polymerization occurred in the liquid phase where propylene was fed into the reactor prior to the addition of the catalyst solutions. In all experiments, the reactor temperature was fixed at 60° C. by electronically controlling the amount of steam added to the reactor jacket. In a typical experiment, hexanes (125 ml) were fed into the dry reactor. A toluene solution (20 mL, 25% wt) of TIBAL was added to the reactor. Propylene (125 ml) was added to the reactor. The reactor was sealed and heated to 60° C. The catalyst solution (catalyst and activator dissolved in 40 mL toluene) was added to the reactor via a catalyst feed pump. Polymerization began immediately upon catalyst addition, and was allowed to continue under controlled temperature for the indicated time. After the indicated time, the reactor was allowed to reach room temperature and vented. The polymerization solution was poured into methanol to induce precipitation. The polymer was collected and dried under ambient condition for 16 h. The polymer was further dried under vacuum at 60° C.

Table 2 below illustrates comparative activities and polymer molecular weight characteristics for isotactic polypropylene products prepared with a chiral biscyclopentadienyl hafnocene activated with a prior art activator (A) and those prepared with the invention activator (B).

TABLE 2

Results of polymerization reactions with propylene

| Act$^a$ | Yield (g) | time (min) | Activity (g/mmol * min) | Mw | Mn | Mw/Mn |
|---|---|---|---|---|---|---|
| A (Comp) | 16.63 | 15 | 1288 | 191,751 | 112,002 | 1.77 |
| A (Comp) | 11.56 | 15 | 896 | 324,379 | 182802 | 1.77 |
| average | | | 1092 | | | |
| B | 24.58 | 10 | 2583 | 252,314 | 223,296 | 1.77 |
| B | 27.86 | 10 | 2940 | 223,296 | 123,895 | 1.80 |
| average | | | 2762 | | | |

$^1$Catalyst: dimethylsilyl(bis-indenyl)hafnium dimethyl
$^a$Activator:
A N,N'-dimethylanilinium tetrakis(pentafluorophenyl) borate
B N-pentafluorophenyl pyrrolidinium tetrakis(pentafluoro-phenyl) borate

I claim:

1. A composition of matter with the formula:

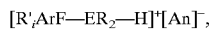

[R'$_i$ArF—ER$_2$—H]$^+$[An]$^-$, where (a) ArF is a fluoroaryl group;

(b) E is nitrogen or phosphorous;

(c) each R is independently a C$_1$–C$_{20}$ hydrocarbyl or hydrocarbylsilyl group, or the two Rs may connect to form an unsubstituted or substituted C$_2$–C$_{20}$ cycloaliphatic group;

(d) R' is a C$_1$–C$_{20}$ hydrocarbyl or halogenated hydrocarbyl;

(e) i is 0 , 1 or 2; and (f) [An]$^-$ is an anion of a strong Bronsted acid.

2. The composition of claim 1 wherein [An]$^-$ is a fluoride, bromide, chloride, or triflate anion.

3. The composition of claim 1 wherein ArF is a fluorinated or perfluorinated aryl group and is one of phenyl, biphenyl, substituted phenyl, substituted biphenyl, terphenyl or substituted terphenyl.

4. The composition of claim 1 wherein —R$_2$— is a substituted or unsubstituted C$_2$–C$_{20}$ cycloaliphatic group.

5. The composition of matter of any of the preceding claims wherein —E is nitrogen.

6. The composition of matter of claim 1 wherein i is 1, Ar is phenyl and R'— is at the para-position of Ar.

7. A composition of matter that is the reaction product of (a) a fluoroaryl-ligand-substituted amine or phosphine with the formula:

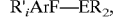

R'$_i$ArF—ER$_2$, where (i) ArF is a fluoroaryl group;

(ii) E is nitrogen or phosphorous;

(iii) each R is independently a C$_1$–C$_{20}$ hydrocarbyl or hydrocarbylsilyl group, or the two Rs may connect to form an unsubstituted or substituted C$_2$–C$_{20}$ cycloaliphatic group;

(iv) R' is a C$_1$–C$_{20}$ hydrocarbyl or halogenated hydrocarbyl;

(v) i is 0, 1 or 2; and (b) a strong Bronsted acid.

8. The composition of claim 7 wherein the acid is hydrofluoric, hydrochloric, hydrobromic, or triflic acid.

9. The composition of claim 7 wherein ArF is a fluorinated or perfluorinated aryl group and is one of phenyl, substituted phenyl, biphenyl, and substituted biphenyl.

10. The composition of claim 7 wherein —R$_2$— is an unsubstituted C$_2$–C$_{20}$ cycloaliphatic group.

11. The composition of matter of one of claims 6–10 wherein E is nitrogen.

12. The composition of matter of claim 1 wherein i is 1, Ar is phenyl and R' is in the para-position of Ar.

13. A compound with the formula:

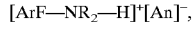

[ArF—NR$_2$—H]$^+$[An]$^-$, where (a) ArF is a fluoroaryl group;

(b) each R is independently a C$_1$–C$_{20}$ hydrocarbyl or hydrocarbylsilyl group, or the two Rs may connect to form an unsubstituted or substituted $C_2$–$C_{20}$ cycloaliphatic group; and (c) [An]⁻ is an anion of a strong Bronsted acid.

14. The composition of claim 13 wherein [An]⁻ is a fluoride, bromide, chloride, or triflate anion.

15. The composition of claim 13 wherein ArF is a fluorinated or perfluorinated aryl group and is one of phenyl, substituted phenyl, biphenyl, substituted biphenyl, terphenyl, or substituted terphenyl.

16. The composition of any of claims 13–15 wherein —$R_2$— is a $C_2$–$C_{20}$ cycloaliphatic group.

17. The composition of claim 16 wherein ArF—$NR_2$ is one of:

N-pentafluorophenylpyrrolidine,
N-para-nanofluorobiphenylpyrrolidine,
N-pentafluorophenypyrrole,
N-parananofluorobiphenylpyrrole,
N-pentafluorophenypiperidine,
N-parananofluorobiphenylpiperidine,
N-pentafluorophenyindoline,
N-paranano-fluorobiphenylindoline,
N-pentafluorophenyindole,
N-parananofluorobiphenylindole,
N-pentafluorophenyazetidine, and
N-parananofluorobiphenylazetidine.

18. The composition of claim 17 wherein ArF—$NR_2$ is N-pentafluorophenyl pyrrolidine.

* * * * *